United States Patent
Swett et al.

(10) Patent No.: US 10,376,845 B2
(45) Date of Patent: Aug. 13, 2019

(54) MEMBRANES WITH TUNABLE SELECTIVITY

(71) Applicant: Lockheed Martin Corporation, Bethesda, MD (US)

(72) Inventors: Jacob Louis Swett, Redwood City, CA (US); Sarah M. Simon, Baltimore, MD (US); Peter V. Bedworth, Los Gatos, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 359 days.

(21) Appl. No.: 15/099,289

(22) Filed: Apr. 14, 2016

(65) Prior Publication Data

US 2017/0296979 A1 Oct. 19, 2017

(51) Int. Cl.
*B01D 69/12* (2006.01)
*A61M 1/16* (2006.01)
(Continued)

(52) U.S. Cl.
CPC .......... *B01D 69/12* (2013.01); *A61M 1/1621* (2014.02); *A61M 1/34* (2013.01); *B01D 69/02* (2013.01); *B01D 71/021* (2013.01); *B32B 9/007* (2013.01); *B32B 38/0032* (2013.01); *C01B 32/194* (2017.08); *B01D 2313/14* (2013.01); *B01D 2313/19* (2013.01); *B01D 2325/02* (2013.01);
(Continued)

(58) Field of Classification Search
None
See application file for complete search history.

(56) References Cited

U.S. PATENT DOCUMENTS 2,187,417 A 1/1940 Doble
3,024,153 A 3/1962 Kennedy
(Continued)

FOREIGN PATENT DOCUMENTS

CA 2037988 9/1992
CA 2411935 12/2002
(Continued)

OTHER PUBLICATIONS

O'Hern, et al. "Selective ionic transport through tunable subnanometer pores in single-layer graphene membranes" Nano Lett. 2014, 14, 1234-1241 (Year: 2014).*
(Continued)

*Primary Examiner* — Ryan B Huang
(74) *Attorney, Agent, or Firm* — Foley & Lardner LLP

(57) ABSTRACT

Some embodiments comprise membranes comprising a first layer comprising a porous graphene-based material; a second layer comprising a porous graphene-based material; a channel positioned between the first layer and the second layer, wherein the channel has a tunable channel diameter; and at least one spacer substance positioned in the channel, wherein the spacer substance is responsive to the environmental stimulus. In some cases, the membranes have more than two layers of porous graphene-based material. Permeability of a membrane can be altered by exposing the membrane to an environmental stimulus. Membranes can be used in methods of water filtration, immune-isolation, timed drug release (e.g., sustained or delayed release), hemodialysis, or hemofiltration.

5 Claims, 8 Drawing Sheets

(51) Int. Cl.
| | |
|---|---|
| *B32B 37/14* | (2006.01) |
| *B32B 37/06* | (2006.01) |
| *B32B 38/00* | (2006.01) |
| *A61M 37/00* | (2006.01) |
| *A61K 47/02* | (2006.01) |
| *A61M 1/34* | (2006.01) |
| *B01D 71/02* | (2006.01) |
| *B01D 67/00* | (2006.01) |
| *B01D 65/00* | (2006.01) |
| *B01D 61/02* | (2006.01) |
| *C02F 1/44* | (2006.01) |
| *A61K 9/70* | (2006.01) |
| *B01D 69/02* | (2006.01) |
| *B32B 9/00* | (2006.01) |
| *C01B 32/194* | (2017.01) |
| *C02F 3/12* | (2006.01) |

(52) U.S. Cl.
CPC .... *B01D 2325/04* (2013.01); *B32B 2307/726* (2013.01); *B32B 2313/04* (2013.01); *C02F 1/44* (2013.01); *C02F 3/1268* (2013.01); *Y02W 10/15* (2015.05)

(56) References Cited

U.S. PATENT DOCUMENTS

| | | | |
|---|---|---|---|
| 3,303,085 A | 2/1967 | Price et al. |
| 3,501,831 A | 3/1970 | Gordon |
| 3,593,854 A | 7/1971 | Swank |
| 3,692,059 A | 9/1972 | Ice, Jr. |
| 3,701,433 A | 10/1972 | Krakauer et al. |
| 3,802,972 A | 4/1974 | Fleischer et al. |
| 4,043,331 A | 8/1977 | Martin et al. |
| 4,073,732 A | 2/1978 | Lauer et al. |
| 4,159,954 A | 7/1979 | Gangemi |
| 4,162,220 A | 7/1979 | Servas |
| 4,277,344 A | 7/1981 | Cadotte |
| 4,303,530 A | 12/1981 | Shah et al. |
| 4,743,371 A | 5/1988 | Servas et al. |
| 4,855,058 A | 8/1989 | Holland et al. |
| 4,880,440 A | 11/1989 | Perrin |
| 4,889,626 A | 12/1989 | Browne |
| 4,891,134 A | 1/1990 | Vcelka |
| 4,925,560 A | 5/1990 | Sorrick |
| 4,935,207 A | 6/1990 | Stanbro et al. |
| 4,976,858 A | 12/1990 | Kadoya |
| 5,052,444 A | 10/1991 | Messerly et al. |
| 5,080,770 A | 1/1992 | Culkin |
| 5,082,476 A | 1/1992 | Kahlbaugh et al. |
| 5,156,628 A | 10/1992 | Kranz |
| 5,182,111 A | 1/1993 | Aebischer et al. |
| 5,185,086 A | 2/1993 | Kaali et al. |
| 5,201,767 A | 4/1993 | Caldarise et al. |
| 5,244,981 A | 9/1993 | Seidner et al. |
| 5,314,492 A | 5/1994 | Hamilton et al. |
| 5,314,960 A | 5/1994 | Spinelli et al. |
| 5,314,961 A | 5/1994 | Anton et al. |
| 5,331,067 A | 7/1994 | Seidner et al. |
| 5,344,454 A | 9/1994 | Clarke et al. |
| 5,371,147 A | 12/1994 | Spinelli et al. |
| 5,425,858 A | 6/1995 | Farmer |
| 5,480,449 A | 1/1996 | Hamilton et al. |
| 5,514,181 A | 5/1996 | Light et al. |
| 5,516,522 A | 5/1996 | Peyman et al. |
| 5,549,697 A | 8/1996 | Caldarise |
| 5,562,944 A | 10/1996 | Kafrawy |
| 5,565,210 A | 10/1996 | Rosenthal et al. |
| 5,580,530 A | 12/1996 | Kowatsch et al. |
| 5,595,621 A | 1/1997 | Light et al. |
| 5,636,437 A | 6/1997 | Kaschmitter et al. |
| 5,639,275 A | 6/1997 | Baetge et al. |
| 5,641,323 A | 6/1997 | Caldarise |
| 5,658,334 A | 8/1997 | Caldarise et al. |
| 5,662,158 A | 9/1997 | Caldarise |
| 5,665,118 A | 9/1997 | Lasalle et al. |
| 5,671,897 A | 9/1997 | Ogg et al. |
| 5,679,232 A | 10/1997 | Fedor et al. |
| 5,679,249 A | 10/1997 | Fendya et al. |
| 5,687,788 A | 11/1997 | Caldarise et al. |
| 5,700,477 A | 12/1997 | Rosenthal et al. |
| 5,713,410 A | 2/1998 | Lasalle et al. |
| 5,716,412 A | 2/1998 | Decarlo et al. |
| 5,716,414 A | 2/1998 | Caldarise |
| 5,725,586 A | 3/1998 | Sommerich |
| 5,731,360 A | 3/1998 | Pekala et al. |
| 5,733,503 A | 3/1998 | Kowatsch et al. |
| 5,746,272 A | 5/1998 | Mastrorio et al. |
| 5,782,286 A | 7/1998 | Sommerich |
| 5,782,289 A | 7/1998 | Mastrorio et al. |
| 5,788,916 A | 8/1998 | Caldarise |
| 5,800,828 A | 9/1998 | Dionne et al. |
| 5,808,312 A | 9/1998 | Fukuda |
| 5,868,727 A | 2/1999 | Barr et al. |
| 5,897,592 A | 4/1999 | Caldarise et al. |
| 5,902,762 A | 5/1999 | Mercuri et al. |
| 5,906,234 A | 5/1999 | Mastrorio et al. |
| 5,910,172 A | 6/1999 | Penenberg |
| 5,910,173 A | 6/1999 | Decarlo et al. |
| 5,913,998 A | 6/1999 | Butler et al. |
| 5,922,304 A | 7/1999 | Unger |
| 5,925,247 A | 7/1999 | Huebbel |
| 5,932,185 A | 8/1999 | Pekala et al. |
| 5,935,084 A | 8/1999 | Southworth |
| 5,935,172 A | 8/1999 | Ochoa et al. |
| 5,954,937 A | 9/1999 | Farmer |
| 5,974,973 A | 11/1999 | Tittgemeyer |
| 5,976,555 A | 11/1999 | Liu et al. |
| 5,980,718 A | 11/1999 | Van Konynenburg et al. |
| 6,008,431 A | 12/1999 | Caldarise et al. |
| 6,013,080 A | 1/2000 | Khalili |
| 6,022,509 A | 2/2000 | Matthews et al. |
| 6,052,608 A | 4/2000 | Young et al. |
| 6,080,393 A | 6/2000 | Liu et al. |
| 6,093,209 A | 7/2000 | Sanders |
| 6,139,585 A | 10/2000 | Li |
| 6,152,882 A | 11/2000 | Prutchi |
| 6,156,323 A | 12/2000 | Verdicchio et al. |
| 6,193,956 B1 | 2/2001 | Liu et al. |
| 6,209,621 B1 | 4/2001 | Treacy |
| 6,213,124 B1 | 4/2001 | Butterworth |
| 6,228,123 B1 | 5/2001 | Dezzani |
| 6,264,699 B1 | 7/2001 | Noiles et al. |
| 6,292,704 B1 | 9/2001 | Malonek et al. |
| 6,309,532 B1 | 10/2001 | Tran et al. |
| 6,346,187 B1 | 2/2002 | Tran et al. |
| 6,375,014 B1 | 4/2002 | Garcera et al. |
| 6,426,214 B1 | 7/2002 | Butler et al. |
| 6,454,095 B1 | 9/2002 | Brisebois et al. |
| 6,455,115 B1 | 9/2002 | Demeyer |
| 6,461,622 B2 | 10/2002 | Liu et al. |
| 6,462,935 B1 | 10/2002 | Shiue et al. |
| 6,521,865 B1 | 2/2003 | Jones et al. |
| 6,532,386 B2 | 3/2003 | Sun et al. |
| 6,544,316 B2 | 4/2003 | Baker et al. |
| 6,580,598 B2 | 6/2003 | Shiue et al. |
| 6,654,229 B2 | 11/2003 | Yanagisawa et al. |
| 6,659,298 B2 | 12/2003 | Wong |
| 6,660,150 B2 | 12/2003 | Conlan et al. |
| 6,661,643 B2 | 12/2003 | Shiue et al. |
| 6,686,437 B2 | 2/2004 | Buchman et al. |
| 6,692,627 B1 | 2/2004 | Russell et al. |
| 6,695,880 B1 | 2/2004 | Roffman et al. |
| 6,699,684 B2 | 3/2004 | Ho et al. |
| 6,719,740 B2 | 4/2004 | Burnett et al. |
| 6,905,612 B2 | 6/2005 | Dorian et al. |
| 6,924,190 B2 | 8/2005 | Dennison |
| 7,014,829 B2 | 3/2006 | Yanagisawa et al. |
| 7,071,406 B2 | 7/2006 | Smalley et al. |
| 7,092,753 B2 | 8/2006 | Darvish et al. |
| 7,138,042 B2 | 11/2006 | Tran et al. |
| 7,171,263 B2 | 1/2007 | Darvish et al. |
| 7,175,783 B2 | 2/2007 | Curran |

(56) References Cited

U.S. PATENT DOCUMENTS

| | | |
|---|---|---|
| 7,179,419 B2 | 2/2007 | Lin et al. |
| 7,190,997 B1 | 3/2007 | Darvish et al. |
| 7,267,753 B2 | 9/2007 | Anex et al. |
| 7,306,768 B2 | 12/2007 | Chiga |
| 7,357,255 B2 | 4/2008 | Ginsberg et al. |
| 7,374,677 B2 | 5/2008 | McLaughlin et al. |
| 7,381,707 B2 | 6/2008 | Lin et al. |
| 7,382,601 B2 | 6/2008 | Yoshimitsu |
| 7,434,692 B2 | 10/2008 | Ginsberg et al. |
| 7,452,547 B2 | 11/2008 | Lambino et al. |
| 7,459,121 B2 | 12/2008 | Liang et al. |
| 7,460,907 B1 | 12/2008 | Darvish et al. |
| 7,476,222 B2 | 1/2009 | Sun et al. |
| 7,477,939 B2 | 1/2009 | Sun et al. |
| 7,477,940 B2 | 1/2009 | Sun et al. |
| 7,477,941 B2 | 1/2009 | Sun et al. |
| 7,479,133 B2 | 1/2009 | Sun et al. |
| 7,505,250 B2 | 3/2009 | Cho et al. |
| 7,531,094 B2 | 5/2009 | McLaughlin et al. |
| 7,600,567 B2 | 10/2009 | Christopher et al. |
| 7,631,764 B2 | 12/2009 | Ginsberg et al. |
| 7,650,805 B2 | 1/2010 | Nauseda et al. |
| 7,674,477 B1 | 3/2010 | Schmid et al. |
| 7,706,128 B2 | 4/2010 | Bourcier |
| 7,761,809 B2 | 7/2010 | Bukovec et al. |
| 7,786,086 B2 | 8/2010 | Reches et al. |
| 7,866,475 B2 | 1/2011 | Doskoczynski et al. |
| 7,875,293 B2 | 1/2011 | Shults et al. |
| 7,935,331 B2 | 5/2011 | Lin |
| 7,935,416 B2 | 5/2011 | Yang et al. |
| 7,943,167 B2 | 5/2011 | Kulkarni et al. |
| 7,960,708 B2 | 6/2011 | Wolfe et al. |
| 7,998,246 B2 | 8/2011 | Liu et al. |
| 8,109,893 B2 | 2/2012 | Lande |
| 8,147,599 B2 | 4/2012 | McAlister |
| 8,262,943 B2 | 9/2012 | Meng et al. |
| 8,278,106 B2 | 10/2012 | Martinson et al. |
| 8,308,702 B2 | 11/2012 | Batchvarova et al. |
| 8,316,865 B2 | 11/2012 | Ochs et al. |
| 8,329,476 B2 | 12/2012 | Pitkanen et al. |
| 8,354,296 B2 | 1/2013 | Dimitrakopoulos et al. |
| 8,361,321 B2 | 1/2013 | Stetson et al. |
| 8,449,504 B2 | 5/2013 | Carter et al. |
| 8,471,562 B2 | 6/2013 | Knizhnik |
| 8,475,689 B2 | 7/2013 | Sun et al. |
| 8,506,807 B2 | 8/2013 | Lee et al. |
| 8,512,669 B2 | 8/2013 | Hauck |
| 8,513,324 B2 | 8/2013 | Scales et al. |
| 8,535,726 B2 | 9/2013 | Dai et al. |
| 8,592,291 B2 | 11/2013 | Shi et al. |
| 8,617,411 B2 | 12/2013 | Singh |
| 8,666,471 B2 | 3/2014 | Rogers et al. |
| 8,686,249 B1 | 4/2014 | Whitaker et al. |
| 8,697,230 B2 | 4/2014 | Ago et al. |
| 8,698,481 B2 | 4/2014 | Lieber et al. |
| 8,715,329 B2 | 5/2014 | Robinson et al. |
| 8,721,074 B2 | 5/2014 | Pugh et al. |
| 8,734,421 B2 | 5/2014 | Sun et al. |
| 8,744,567 B2 | 6/2014 | Fassih et al. |
| 8,751,015 B2 | 6/2014 | Frewin et al. |
| 8,753,468 B2 | 6/2014 | Caldwell et al. |
| 8,759,153 B2 | 6/2014 | Elian et al. |
| 8,808,257 B2 | 8/2014 | Pugh et al. |
| 8,828,211 B2 | 9/2014 | Garaj et al. |
| 8,840,552 B2 | 9/2014 | Brauker et al. |
| 8,857,983 B2 | 10/2014 | Pugh et al. |
| 8,861,821 B2 | 10/2014 | Osumi |
| 8,894,201 B2 | 11/2014 | Pugh et al. |
| 8,940,552 B2 | 1/2015 | Pugh et al. |
| 8,950,862 B2 | 2/2015 | Pugh et al. |
| 8,974,055 B2 | 3/2015 | Pugh et al. |
| 8,975,121 B2 | 3/2015 | Pugh et al. |
| 8,979,978 B2 | 3/2015 | Miller et al. |
| 8,986,932 B2 | 3/2015 | Turner et al. |
| 8,993,234 B2 | 3/2015 | Turner et al. |
| 8,993,327 B2 | 3/2015 | McKnight et al. |
| 9,014,639 B2 | 4/2015 | Pugh et al. |
| 9,017,937 B1 | 4/2015 | Turner et al. |
| 9,023,220 B2 | 5/2015 | Zurutuza Elorza et al. |
| 9,028,663 B2 | 5/2015 | Stetson et al. |
| 9,035,282 B2 | 5/2015 | Dimitrakopoulos et al. |
| 9,045,847 B2 | 6/2015 | Batchvarova et al. |
| 9,050,452 B2 | 6/2015 | Sun et al. |
| 9,052,533 B2 | 6/2015 | Pugh et al. |
| 9,056,282 B2 | 6/2015 | Miller et al. |
| 9,062,180 B2 | 6/2015 | Scales et al. |
| 9,067,811 B1 | 6/2015 | Bennett et al. |
| 9,070,615 B2 | 6/2015 | Elian et al. |
| 9,075,009 B2 | 7/2015 | Kim et al. |
| 9,080,267 B2 | 7/2015 | Batchvarova et al. |
| 9,095,823 B2 | 8/2015 | Fleming |
| 9,096,050 B2 | 8/2015 | Bedell et al. |
| 9,096,437 B2 | 8/2015 | Tour et al. |
| 9,102,111 B2 | 8/2015 | Pugh et al. |
| 9,108,158 B2 | 8/2015 | Yu et al. |
| 9,110,310 B2 | 8/2015 | Pugh et al. |
| 9,125,715 B2 | 9/2015 | Pugh et al. |
| 9,134,546 B2 | 9/2015 | Pugh et al. |
| 9,156,700 B2 * | 10/2015 | Zhamu ............... C01B 31/0469 |
| 9,170,646 B2 | 10/2015 | Toner et al. |
| 9,185,486 B2 | 11/2015 | Pugh |
| 9,193,587 B2 | 11/2015 | Bennett |
| 9,195,075 B2 | 11/2015 | Pugh et al. |
| 9,225,375 B2 | 12/2015 | Pugh et al. |
| 9,388,048 B1 | 7/2016 | Zhou et al. |
| 9,425,709 B2 | 8/2016 | Hayashi et al. |
| 9,437,370 B2 | 9/2016 | Chen et al. |
| 9,463,421 B2 | 10/2016 | Fleming |
| 9,475,709 B2 | 10/2016 | Stetson et al. |
| 9,505,192 B2 | 11/2016 | Stoltenberg et al. |
| 9,545,600 B2 | 1/2017 | Miller et al. |
| 9,567,224 B2 | 2/2017 | Bedworth |
| 9,572,918 B2 | 2/2017 | Bachmann et al. |
| 9,592,475 B2 | 3/2017 | Stoltenberg et al. |
| 9,610,546 B2 | 4/2017 | Sinton et al. |
| 9,656,214 B2 | 5/2017 | Miller et al. |
| 9,708,640 B2 | 7/2017 | Wu et al. |
| 9,713,794 B2 | 7/2017 | Choi et al. |
| 9,742,001 B2 | 8/2017 | Zhamu et al. |
| 9,744,617 B2 | 8/2017 | Bedworth et al. |
| 9,870,895 B2 | 1/2018 | Bedworth |
| 10,017,852 B2 | 7/2018 | Heise |
| 2001/0036556 A1 | 11/2001 | Jen |
| 2001/0047157 A1 | 11/2001 | Burnett et al. |
| 2001/0055597 A1 | 12/2001 | Liu et al. |
| 2002/0079004 A1 | 6/2002 | Sato et al. |
| 2002/0079054 A1 | 6/2002 | Nakatani |
| 2002/0104435 A1 | 8/2002 | Baker et al. |
| 2002/0115957 A1 | 8/2002 | Sun et al. |
| 2002/0117659 A1 | 8/2002 | Lieber et al. |
| 2002/0183682 A1 | 12/2002 | Darvish et al. |
| 2002/0183686 A1 | 12/2002 | Darvish et al. |
| 2003/0052354 A1 | 3/2003 | Dennison |
| 2003/0134281 A1 | 7/2003 | Evans |
| 2003/0138777 A1 | 7/2003 | Evans |
| 2003/0159985 A1 | 8/2003 | Siwy et al. |
| 2004/0018583 A1 | 1/2004 | Ho et al. |
| 2004/0035787 A1 | 2/2004 | Tanga et al. |
| 2004/0061253 A1 | 4/2004 | Kleinmeyer et al. |
| 2004/0063097 A1 | 4/2004 | Evans |
| 2004/0099324 A1 | 5/2004 | Fraser et al. |
| 2004/0111968 A1 | 6/2004 | Day et al. |
| 2004/0112865 A1 | 6/2004 | McCullough et al. |
| 2004/0121488 A1 | 6/2004 | Chang et al. |
| 2004/0140041 A1 | 7/2004 | Glick |
| 2004/0142463 A1 | 7/2004 | Walker et al. |
| 2004/0185730 A1 | 9/2004 | Lambino et al. |
| 2004/0193043 A1 | 9/2004 | Duchon et al. |
| 2004/0199243 A1 | 10/2004 | Yodfat |
| 2004/0208796 A1 | 10/2004 | Chiga |
| 2004/0217036 A1 | 11/2004 | Ginsberg et al. |
| 2004/0241214 A1 | 12/2004 | Kirkwood et al. |
| 2004/0251136 A1 | 12/2004 | Lean et al. |
| 2005/0004508 A1 | 1/2005 | Sun et al. |

(56) References Cited

U.S. PATENT DOCUMENTS

| | | |
|---|---|---|
| 2005/0004509 A1 | 1/2005 | Sun et al. |
| 2005/0004550 A1 | 1/2005 | Sun et al. |
| 2005/0010161 A1 | 1/2005 | Sun et al. |
| 2005/0010192 A1 | 1/2005 | Sun et al. |
| 2005/0015042 A1 | 1/2005 | Sun et al. |
| 2005/0053563 A1 | 3/2005 | Manissier et al. |
| 2005/0112078 A1 | 5/2005 | Boddupalli et al. |
| 2005/0126966 A1 | 6/2005 | Tanida et al. |
| 2005/0129633 A1 | 6/2005 | Lin |
| 2005/0148996 A1 | 7/2005 | Sun et al. |
| 2005/0170089 A1 | 8/2005 | Lashmore et al. |
| 2005/0189673 A1 | 9/2005 | Klug et al. |
| 2005/0226834 A1 | 10/2005 | Lambino et al. |
| 2005/0238730 A1 | 10/2005 | Le Fur et al. |
| 2006/0005381 A1 | 1/2006 | Nishi et al. |
| 2006/0036332 A1 | 2/2006 | Jennings |
| 2006/0073370 A1 | 4/2006 | Krusic et al. |
| 2006/0093885 A1 | 5/2006 | Krusic et al. |
| 2006/0121279 A1 | 6/2006 | Petrik |
| 2006/0151382 A1 | 7/2006 | Petrik |
| 2006/0166347 A1 | 7/2006 | Faulstich et al. |
| 2006/0180604 A1 | 8/2006 | Ginsberg et al. |
| 2006/0222701 A1 | 10/2006 | Kulkarni et al. |
| 2006/0253078 A1 | 11/2006 | Wu et al. |
| 2007/0004640 A1 | 1/2007 | Lin et al. |
| 2007/0032054 A1 | 2/2007 | Ramaswamy et al. |
| 2007/0056894 A1 | 3/2007 | Connors, Jr. |
| 2007/0060862 A1 | 3/2007 | Sun et al. |
| 2007/0062856 A1 | 3/2007 | Pahl et al. |
| 2007/0099813 A1 | 5/2007 | Luizzi et al. |
| 2007/0131646 A1 | 6/2007 | Donnelly et al. |
| 2007/0284279 A1 | 12/2007 | Doskoczynski et al. |
| 2008/0017564 A1 | 1/2008 | Hammond |
| 2008/0035484 A1 | 2/2008 | Wu et al. |
| 2008/0035541 A1 | 2/2008 | Franzreb et al. |
| 2008/0045877 A1 | 2/2008 | Levin et al. |
| 2008/0061477 A1 | 3/2008 | Capizzo |
| 2008/0063585 A1 | 3/2008 | Smalley et al. |
| 2008/0081323 A1 | 4/2008 | Keeley et al. |
| 2008/0081362 A1 | 4/2008 | Keeley et al. |
| 2008/0149561 A1 | 6/2008 | Chu et al. |
| 2008/0156648 A1 | 7/2008 | Dudziak et al. |
| 2008/0170982 A1 | 7/2008 | Zhang et al. |
| 2008/0185293 A1 | 8/2008 | Klose et al. |
| 2008/0188836 A1 | 8/2008 | Weber et al. |
| 2008/0190508 A1 | 8/2008 | Booth et al. |
| 2008/0241085 A1 | 10/2008 | Lin et al. |
| 2008/0268016 A1 | 10/2008 | Fang et al. |
| 2008/0290020 A1 | 11/2008 | Marand et al. |
| 2008/0290111 A1 | 11/2008 | Ginsberg et al. |
| 2009/0023572 A1 | 1/2009 | Backes et al. |
| 2009/0032475 A1 | 2/2009 | Ferrer et al. |
| 2009/0039019 A1 | 2/2009 | Raman |
| 2009/0048685 A1 | 2/2009 | Frigstad et al. |
| 2009/0075371 A1 | 3/2009 | Keeley et al. |
| 2009/0078640 A1 | 3/2009 | Chu et al. |
| 2009/0087395 A1 | 4/2009 | Lin et al. |
| 2009/0117335 A1 | 5/2009 | Iyoda et al. |
| 2009/0148495 A1 | 6/2009 | Hammer et al. |
| 2009/0176159 A1 | 7/2009 | Zhamu et al. |
| 2009/0222072 A1 | 9/2009 | Robinson et al. |
| 2009/0236295 A1 | 9/2009 | Braun et al. |
| 2009/0241242 A1 | 10/2009 | Beatty et al. |
| 2009/0283475 A1 | 11/2009 | Hylton et al. |
| 2009/0291270 A1 | 11/2009 | Zettl et al. |
| 2009/0294300 A1 | 12/2009 | Kanzius et al. |
| 2009/0306364 A1 | 12/2009 | Beer et al. |
| 2010/0000754 A1 | 1/2010 | Mann et al. |
| 2010/0016778 A1 | 1/2010 | Chattopadhyay |
| 2010/0021708 A1 | 1/2010 | Kong et al. |
| 2010/0024722 A1 | 2/2010 | Ochs et al. |
| 2010/0024838 A1 | 2/2010 | Ochs et al. |
| 2010/0025330 A1 | 2/2010 | Ratto et al. |
| 2010/0055464 A1 | 3/2010 | Sung |
| 2010/0059378 A1 | 3/2010 | Elson et al. |
| 2010/0072643 A1 | 3/2010 | Pugh et al. |
| 2010/0076553 A1 | 3/2010 | Pugh et al. |
| 2010/0105834 A1 | 4/2010 | Tour et al. |
| 2010/0110372 A1 | 5/2010 | Pugh et al. |
| 2010/0124564 A1 | 5/2010 | Martinson et al. |
| 2010/0127312 A1 | 5/2010 | Grebel et al. |
| 2010/0161014 A1 | 6/2010 | Lynch et al. |
| 2010/0167551 A1 | 7/2010 | Dedontney |
| 2010/0196439 A1 | 8/2010 | Beck et al. |
| 2010/0209330 A1 | 8/2010 | Golzhauser et al. |
| 2010/0209515 A1 | 8/2010 | Chantalat et al. |
| 2010/0213079 A1 | 8/2010 | Willis |
| 2010/0224555 A1 | 9/2010 | Hoek et al. |
| 2010/0228204 A1 | 9/2010 | Beatty et al. |
| 2010/0233781 A1 | 9/2010 | Bangera et al. |
| 2010/0249273 A1 | 9/2010 | Scales et al. |
| 2010/0258111 A1 | 10/2010 | Shah et al. |
| 2010/0323177 A1 | 12/2010 | Ruoff et al. |
| 2010/0327847 A1 | 12/2010 | Leiber et al. |
| 2011/0014217 A1 | 1/2011 | Fahmy et al. |
| 2011/0037033 A1 | 2/2011 | Green et al. |
| 2011/0041519 A1 | 2/2011 | McAlister |
| 2011/0041687 A1 | 2/2011 | Diaz et al. |
| 2011/0045523 A1 | 2/2011 | Strano et al. |
| 2011/0054418 A1 | 3/2011 | Pugh et al. |
| 2011/0054576 A1 | 3/2011 | Robinson et al. |
| 2011/0056892 A1 | 3/2011 | Lancaster |
| 2011/0073563 A1 | 3/2011 | Chang et al. |
| 2011/0092054 A1 | 4/2011 | Seo et al. |
| 2011/0092949 A1 | 4/2011 | Wang |
| 2011/0100921 A1 | 5/2011 | Heinrich |
| 2011/0112484 A1 | 5/2011 | Carter et al. |
| 2011/0118655 A1 | 5/2011 | Fassih et al. |
| 2011/0120970 A1 | 5/2011 | Joo et al. |
| 2011/0124253 A1 | 5/2011 | Shah et al. |
| 2011/0132834 A1 | 6/2011 | Tomioka et al. |
| 2011/0139707 A1 | 6/2011 | Siwy et al. |
| 2011/0152795 A1 | 6/2011 | Aledo et al. |
| 2011/0189440 A1 | 8/2011 | Appleby et al. |
| 2011/0201201 A1 | 8/2011 | Arnold et al. |
| 2011/0202201 A1 | 8/2011 | Matsubara |
| 2011/0253630 A1 | 10/2011 | Bakajin et al. |
| 2011/0258791 A1 | 10/2011 | Batchvarova et al. |
| 2011/0258796 A1 | 10/2011 | Batchvarova et al. |
| 2011/0262645 A1 | 10/2011 | Batchvarova et al. |
| 2011/0263912 A1 | 10/2011 | Miller et al. |
| 2011/0269920 A1 | 11/2011 | Min et al. |
| 2012/0000845 A1 | 1/2012 | Park et al. |
| 2012/0031833 A1 | 2/2012 | Ho et al. |
| 2012/0048804 A1 | 3/2012 | Stetson et al. |
| 2012/0115243 A1 | 5/2012 | Pitkanen et al. |
| 2012/0116228 A1 | 5/2012 | Okubo |
| 2012/0145548 A1 | 6/2012 | Sivan et al. |
| 2012/0148633 A1 | 6/2012 | Sun et al. |
| 2012/0162600 A1 | 6/2012 | Pugh et al. |
| 2012/0183738 A1 | 7/2012 | Zettl et al. |
| 2012/0186850 A1 | 7/2012 | Sugiyama et al. |
| 2012/0211367 A1 | 8/2012 | Vecitis |
| 2012/0218508 A1 | 8/2012 | Pugh et al. |
| 2012/0219203 A1 | 8/2012 | Adachi |
| 2012/0220053 A1 | 8/2012 | Lee et al. |
| 2012/0234453 A1 | 9/2012 | Pugh et al. |
| 2012/0234679 A1 | 9/2012 | Garaj et al. |
| 2012/0235277 A1 | 9/2012 | Pugh et al. |
| 2012/0236254 A1 | 9/2012 | Pugh et al. |
| 2012/0236524 A1 | 9/2012 | Pugh et al. |
| 2012/0241371 A1 | 9/2012 | Revanur et al. |
| 2012/0242953 A1 | 9/2012 | Pugh et al. |
| 2012/0255899 A1 | 10/2012 | Choi et al. |
| 2012/0267337 A1 | 10/2012 | Striemer et al. |
| 2012/0292245 A1 | 11/2012 | Saito |
| 2012/0294793 A1* | 11/2012 | Chen ............... B82Y 30/00 423/448 |
| 2012/0298396 A1 | 11/2012 | Hong et al. |
| 2012/0301707 A1 | 11/2012 | Kinloch et al. |
| 2013/0015136 A1 | 1/2013 | Bennett |
| 2013/0034760 A1 | 2/2013 | Otts et al. |
| 2013/0045523 A1 | 2/2013 | Leach et al. |
| 2013/0056367 A1 | 3/2013 | Martinez et al. |

(56) References Cited

U.S. PATENT DOCUMENTS

| | | |
|---|---|---|
| 2013/0071941 A1 | 3/2013 | Miller |
| 2013/0096292 A1 | 4/2013 | Brahmasandra et al. |
| 2013/0100436 A1 | 4/2013 | Jackson et al. |
| 2013/0105417 A1 | 5/2013 | Stetson et al. |
| 2013/0108839 A1 | 5/2013 | Arnold et al. |
| 2013/0116541 A1 | 5/2013 | Gracias et al. |
| 2013/0131214 A1 | 5/2013 | Scales et al. |
| 2013/0135578 A1 | 5/2013 | Pugh et al. |
| 2013/0146221 A1 | 6/2013 | Kolmakov et al. |
| 2013/0146480 A1 | 6/2013 | Garaj et al. |
| 2013/0152386 A1 | 6/2013 | Pandojirao-S et al. |
| 2013/0174968 A1 | 7/2013 | Vlassiouk et al. |
| 2013/0174978 A1 | 7/2013 | Pugh et al. |
| 2013/0176030 A1 | 7/2013 | Simon |
| 2013/0190476 A1 | 7/2013 | Lancaster et al. |
| 2013/0192460 A1 | 8/2013 | Miller et al. |
| 2013/0192461 A1 | 8/2013 | Miller et al. |
| 2013/0194540 A1 | 8/2013 | Pugh et al. |
| 2013/0213568 A1 | 8/2013 | Pugh et al. |
| 2013/0215377 A1 | 8/2013 | Pugh et al. |
| 2013/0215378 A1 | 8/2013 | Pugh et al. |
| 2013/0215380 A1 | 8/2013 | Pugh et al. |
| 2013/0216581 A1 | 8/2013 | Fahmy et al. |
| 2013/0240355 A1 | 9/2013 | Ho et al. |
| 2013/0240437 A1 | 9/2013 | Rodrigues et al. |
| 2013/0248097 A1 | 9/2013 | Ploss, Jr. |
| 2013/0248367 A1 | 9/2013 | Stetson et al. |
| 2013/0249147 A1 | 9/2013 | Bedworth |
| 2013/0256118 A1 | 10/2013 | Meller et al. |
| 2013/0256139 A1 | 10/2013 | Peng |
| 2013/0256154 A1 | 10/2013 | Peng |
| 2013/0256210 A1 | 10/2013 | Fleming |
| 2013/0256211 A1 | 10/2013 | Fleming |
| 2013/0261568 A1 | 10/2013 | Martinson et al. |
| 2013/0269819 A1 | 10/2013 | Ruby et al. |
| 2013/0270188 A1 | 10/2013 | Karnik et al. |
| 2013/0273288 A1 | 10/2013 | Luo et al. |
| 2013/0277305 A1 | 10/2013 | Stetson et al. |
| 2013/0277573 A1 | 10/2013 | Miller et al. |
| 2013/0284665 A1 | 10/2013 | Lee et al. |
| 2013/0295150 A1 | 11/2013 | Chantalat et al. |
| 2013/0309776 A1 | 11/2013 | Drndic et al. |
| 2013/0317131 A1 | 11/2013 | Scales et al. |
| 2013/0317132 A1 | 11/2013 | Scales et al. |
| 2013/0317133 A1 | 11/2013 | Scales et al. |
| 2013/0323295 A1 | 12/2013 | Scales et al. |
| 2013/0335092 A1 | 12/2013 | Wu |
| 2013/0338611 A1 | 12/2013 | Pugh et al. |
| 2013/0338744 A1 | 12/2013 | Frewin et al. |
| 2014/0002788 A1 | 1/2014 | Otts et al. |
| 2014/0005514 A1 | 1/2014 | Pugh et al. |
| 2014/0015160 A1 | 1/2014 | Kung et al. |
| 2014/0017322 A1 | 1/2014 | Dai et al. |
| 2014/0030482 A1 | 1/2014 | Miller et al. |
| 2014/0048411 A1 | 2/2014 | Choi et al. |
| 2014/0066958 A1 | 3/2014 | Priewe |
| 2014/0079936 A1 | 3/2014 | Russo et al. |
| 2014/0093728 A1 | 4/2014 | Shah et al. |
| 2014/0128891 A1 | 5/2014 | Astani-Matthies et al. |
| 2014/0141521 A1 | 5/2014 | Peng et al. |
| 2014/0151288 A1 | 6/2014 | Miller et al. |
| 2014/0151631 A1 | 6/2014 | Duesberg et al. |
| 2014/0154464 A1 | 6/2014 | Miller et al. |
| 2014/0170195 A1 | 6/2014 | Fassih et al. |
| 2014/0171541 A1 | 6/2014 | Scales et al. |
| 2014/0174927 A1 | 6/2014 | Bashir et al. |
| 2014/0190004 A1 | 7/2014 | Riall et al. |
| 2014/0190550 A1 | 7/2014 | Loh et al. |
| 2014/0190676 A1 | 7/2014 | Zhamu et al. |
| 2014/0190833 A1 | 7/2014 | Lieber et al. |
| 2014/0192313 A1 | 7/2014 | Riall et al. |
| 2014/0192314 A1 | 7/2014 | Riall et al. |
| 2014/0199777 A2 | 7/2014 | Ruiz et al. |
| 2014/0209539 A1 | 7/2014 | El Badawi et al. |
| 2014/0212596 A1 | 7/2014 | Jahangiri-Famenini |
| 2014/0230653 A1 | 8/2014 | Yu et al. |
| 2014/0230733 A1 | 8/2014 | Miller |
| 2014/0231351 A1 | 8/2014 | Wickramasinghe et al. |
| 2014/0248621 A1 | 9/2014 | Collins |
| 2014/0253131 A1 | 9/2014 | Liu et al. |
| 2014/0257348 A1 | 9/2014 | Priewe et al. |
| 2014/0257515 A1 | 9/2014 | So et al. |
| 2014/0257517 A1 | 9/2014 | Deichmann et al. |
| 2014/0259657 A1 | 9/2014 | Riall et al. |
| 2014/0261999 A1 | 9/2014 | Stetson et al. |
| 2014/0263035 A1 | 9/2014 | Stoltenberg et al. |
| 2014/0263178 A1 | 9/2014 | Sinton et al. |
| 2014/0264977 A1 | 9/2014 | Pugh et al. |
| 2014/0268015 A1 | 9/2014 | Riall et al. |
| 2014/0268020 A1 | 9/2014 | Pugh et al. |
| 2014/0268021 A1 | 9/2014 | Pugh et al. |
| 2014/0268026 A1 | 9/2014 | Pugh et al. |
| 2014/0272286 A1 | 9/2014 | Stoltenberg et al. |
| 2014/0272522 A1 | 9/2014 | Pugh et al. |
| 2014/0273315 A1 | 9/2014 | Pugh et al. |
| 2014/0273316 A1 | 9/2014 | Pugh et al. |
| 2014/0276481 A1 | 9/2014 | Pugh et al. |
| 2014/0276999 A1 | 9/2014 | Harms et al. |
| 2014/0306361 A1 | 10/2014 | Pugh et al. |
| 2014/0308681 A1 | 10/2014 | Strano et al. |
| 2014/0311967 A1 | 10/2014 | Grossman et al. |
| 2014/0315213 A1 | 10/2014 | Nagrath et al. |
| 2014/0318373 A1 | 10/2014 | Wood et al. |
| 2014/0322518 A1 | 10/2014 | Addleman et al. |
| 2014/0333892 A1 | 11/2014 | Pugh et al. |
| 2014/0335661 A1 | 11/2014 | Pugh et al. |
| 2014/0343580 A1 | 11/2014 | Priewe |
| 2014/0346081 A1 | 11/2014 | Sowden et al. |
| 2014/0346631 A1 | 11/2014 | Karim et al. |
| 2014/0349892 A1 | 11/2014 | Van Der Zaag et al. |
| 2014/0350372 A1 | 11/2014 | Pugh et al. |
| 2014/0377651 A1 | 12/2014 | Kwon et al. |
| 2014/0377738 A1 | 12/2014 | Bachmann et al. |
| 2015/0015843 A1 | 1/2015 | Pugh et al. |
| 2015/0017918 A1 | 1/2015 | Pugh et al. |
| 2015/0053627 A1 | 2/2015 | Silin et al. |
| 2015/0057762 A1 | 2/2015 | Harms et al. |
| 2015/0061990 A1 | 3/2015 | Toner et al. |
| 2015/0062533 A1 | 3/2015 | Toner et al. |
| 2015/0063605 A1 | 3/2015 | Pugh |
| 2015/0066063 A1 | 3/2015 | Priewe |
| 2015/0075667 A1 | 3/2015 | McHugh et al. |
| 2015/0077658 A1 | 3/2015 | Pugh et al. |
| 2015/0077659 A1 | 3/2015 | Pugh et al. |
| 2015/0077660 A1 | 3/2015 | Pugh et al. |
| 2015/0077661 A1 | 3/2015 | Pugh et al. |
| 2015/0077662 A1 | 3/2015 | Pugh et al. |
| 2015/0077663 A1 | 3/2015 | Pugh et al. |
| 2015/0077699 A1 | 3/2015 | De Sio et al. |
| 2015/0077702 A9 | 3/2015 | Pugh et al. |
| 2015/0079683 A1 | 3/2015 | Yager et al. |
| 2015/0087249 A1 | 3/2015 | Pugh et al. |
| 2015/0096935 A1 | 4/2015 | Mitra et al. |
| 2015/0098910 A1 | 4/2015 | Mordas et al. |
| 2015/0101931 A1 | 4/2015 | Garaj et al. |
| 2015/0105686 A1 | 4/2015 | Vasan |
| 2015/0118318 A1 | 4/2015 | Fahmy et al. |
| 2015/0122727 A1 | 5/2015 | Karnik et al. |
| 2015/0137817 A1 | 5/2015 | Wilson et al. |
| 2015/0138454 A1 | 5/2015 | Pugh et al. |
| 2015/0142107 A1 | 5/2015 | Pugh et al. |
| 2015/0145155 A1 | 5/2015 | Pugh et al. |
| 2015/0146162 A1 | 5/2015 | Pugh et al. |
| 2015/0147474 A1 | 5/2015 | Batchvarova et al. |
| 2015/0170788 A1 | 6/2015 | Miller et al. |
| 2015/0174253 A1 | 6/2015 | Sun et al. |
| 2015/0174254 A1 | 6/2015 | Sun et al. |
| 2015/0182473 A1 | 7/2015 | Bosnyak et al. |
| 2015/0185180 A1 | 7/2015 | Ruhl et al. |
| 2015/0196579 A1 | 7/2015 | Ferrante et al. |
| 2015/0202351 A1 | 7/2015 | Kaplan et al. |
| 2015/0212339 A1 | 7/2015 | Pugh et al. |
| 2015/0217219 A1 | 8/2015 | Sinsabaugh et al. |
| 2015/0218210 A1 | 8/2015 | Stetson et al. |

(56) References Cited

U.S. PATENT DOCUMENTS

| | | |
|---|---|---|
| 2015/0221474 A1 | 8/2015 | Bedworth |
| 2015/0231557 A1 | 8/2015 | Miller et al. |
| 2015/0231577 A1 | 8/2015 | Nair et al. |
| 2015/0247178 A1 | 9/2015 | Mountcastle et al. |
| 2015/0258254 A1 | 9/2015 | Simon et al. |
| 2015/0258498 A1 | 9/2015 | Simon et al. |
| 2015/0258502 A1 | 9/2015 | Turowski |
| 2015/0258503 A1 | 9/2015 | Sinton et al. |
| 2015/0258506 A1* | 9/2015 | Mi .................. C01B 31/043 156/273.1 |
| 2015/0258525 A1 | 9/2015 | Westman et al. |
| 2015/0268150 A1 | 9/2015 | Newkirk et al. |
| 2015/0272834 A1 | 10/2015 | Sun et al. |
| 2015/0272896 A1 | 10/2015 | Sun et al. |
| 2015/0273401 A1 | 10/2015 | Miller et al. |
| 2015/0309337 A1 | 10/2015 | Flitsch et al. |
| 2015/0321147 A1 | 11/2015 | Fleming et al. |
| 2015/0321149 A1 | 11/2015 | McGinnis |
| 2015/0323811 A1 | 11/2015 | Flitsch et al. |
| 2015/0336202 A1 | 11/2015 | Bedworth et al. |
| 2015/0342900 A1 | 12/2015 | Putnins |
| 2015/0346382 A1 | 12/2015 | Bliven et al. |
| 2015/0351887 A1 | 12/2015 | Peters |
| 2015/0359742 A1 | 12/2015 | Fassih et al. |
| 2015/0376448 A1 | 12/2015 | Urs |
| 2015/0378176 A1 | 12/2015 | Flitsch et al. |
| 2016/0009049 A1 | 1/2016 | Stoltenberg et al. |
| 2016/0038885 A1 | 2/2016 | Hogen-Esch et al. |
| 2016/0043384 A1 | 2/2016 | Zhamu et al. |
| 2016/0058932 A1 | 3/2016 | Stetson et al. |
| 2016/0059190 A1 | 3/2016 | Yoo et al. |
| 2016/0067390 A1 | 3/2016 | Simon et al. |
| 2016/0074814 A1 | 3/2016 | Park et al. |
| 2016/0074815 A1 | 3/2016 | Sinton et al. |
| 2016/0084008 A1 | 3/2016 | Faircloth et al. |
| 2016/0084981 A1 | 3/2016 | Kayano et al. |
| 2016/0116237 A1 | 4/2016 | Alsadah et al. |
| 2016/0256805 A1 | 9/2016 | Grein et al. |
| 2016/0272499 A1 | 9/2016 | Zurutuza Elorza et al. |
| 2016/0282326 A1 | 9/2016 | Waduge et al. |
| 2016/0284811 A1 | 9/2016 | Yu et al. |
| 2016/0339160 A1 | 11/2016 | Bedworth et al. |
| 2017/0000937 A1 | 1/2017 | Gottschalk |
| 2017/0032962 A1 | 2/2017 | Zurutuza Elorza et al. |
| 2017/0035943 A1 | 2/2017 | Simon et al. |
| 2017/0036916 A1 | 2/2017 | Bedworth et al. |
| 2017/0037356 A1 | 2/2017 | Simon et al. |
| 2017/0057812 A1 | 3/2017 | Zurutuza Elorza et al. |
| 2017/0065939 A1 | 3/2017 | Kim et al. |
| 2017/0144107 A1 | 5/2017 | Garaj et al. |
| 2017/0202885 A1 | 7/2017 | Agulnick |
| 2017/0216923 A1 | 8/2017 | Babenko et al. |
| 2017/0217777 A1 | 8/2017 | Hong et al. |
| 2017/0239623 A1 | 8/2017 | Stoltenberg et al. |
| 2017/0296706 A1 | 10/2017 | Simon et al. |
| 2017/0296972 A1 | 10/2017 | Sinton et al. |
| 2017/0296976 A1 | 10/2017 | Liu et al. |
| 2017/0296979 A1 | 10/2017 | Swett et al. |
| 2018/0147542 A1 | 5/2018 | Jhon et al. |
| 2018/0207591 A1 | 7/2018 | Yu et al. |

FOREIGN PATENT DOCUMENTS

| | | |
|---|---|---|
| CN | 1128501 A | 8/1996 |
| CN | 101108194 A | 1/2008 |
| CN | 101243544 | 8/2008 |
| CN | 101428198 A | 5/2009 |
| CN | 101489653 A | 7/2009 |
| CN | 101996853 A | 3/2011 |
| CN | 102242062 A | 11/2011 |
| CN | 102344132 | 2/2012 |
| CN | 102423272 | 4/2012 |
| CN | 102592720 A | 7/2012 |
| CN | 101996853 B | 8/2012 |
| CN | 102637584 A | 8/2012 |
| CN | 103153441 | 6/2013 |
| CN | 103182249 A | 7/2013 |
| CN | 203235358 | 10/2013 |
| CN | 103480281 | 1/2014 |
| CN | 103585891 | 2/2014 |
| CN | 103603706 A | 2/2014 |
| DE | 19536560 | 3/1997 |
| DE | 10 2005 049 388 A1 | 4/2007 |
| EP | 0 364 628 A1 | 4/1990 |
| EP | 1 034 251 | 1/2004 |
| EP | 1 777 250 A1 | 4/2007 |
| EP | 1 872 812 | 1/2008 |
| EP | 2 060 286 | 5/2009 |
| EP | 2 107 120 A1 | 10/2009 |
| EP | 2 230 511 A1 | 9/2010 |
| EP | 1 603 609 | 5/2011 |
| EP | 2 354 272 | 8/2011 |
| EP | 2 450 096 | 5/2012 |
| EP | 2 489 520 | 8/2012 |
| EP | 2 511 002 | 10/2012 |
| EP | 2 586 473 | 5/2013 |
| EP | 2 679 540 | 1/2014 |
| EP | 2 937 313 | 10/2015 |
| EP | 3 070 053 | 9/2016 |
| EP | 3 084 398 | 10/2016 |
| EP | 1 538 2430.5 | 3/2017 |
| EP | 3 135 631 | 3/2017 |
| JP | 59-102111 | 7/1984 |
| JP | 10-510471 | 5/1995 |
| JP | 7504120 | 5/1995 |
| JP | 2001-232158 | 8/2001 |
| JP | 2002-126510 | 5/2002 |
| JP | 2004-179014 | 6/2004 |
| JP | 2005-126966 | 5/2005 |
| JP | 2006-188393 | 7/2006 |
| JP | 2009-291777 | 12/2009 |
| JP | 2011-168448 A | 9/2011 |
| JP | 2011-241479 | 12/2011 |
| JP | 2012-500708 | 1/2012 |
| JP | 2004-202480 | 7/2014 |
| JP | 2015-503405 | 2/2015 |
| JP | 2016-175828 | 10/2016 |
| KR | 1020110084110 | 7/2011 |
| KR | 10-2012-0022164 A | 3/2012 |
| KR | 1020120022164 A | 3/2012 |
| KR | 1020140002570 | 1/2014 |
| WO | WO-93/33901 | 3/1993 |
| WO | WO-93/12859 | 8/1993 |
| WO | WO-95/00231 | 1/1995 |
| WO | WO-97/12664 A1 | 4/1997 |
| WO | WO-98/30501 A2 | 7/1998 |
| WO | WO-00/70012 | 11/2000 |
| WO | WO-02/055539 A1 | 7/2002 |
| WO | WO-2013/115762 | 8/2003 |
| WO | WO-2004/009840 A1 | 1/2004 |
| WO | WO-2004/082733 | 9/2004 |
| WO | WO-2005/047857 A2 | 5/2005 |
| WO | WO-2007/103411 A2 | 9/2007 |
| WO | WO-2007/140252 A1 | 12/2007 |
| WO | WO-2008/008533 | 1/2008 |
| WO | WO-2009/129984 A1 | 10/2009 |
| WO | WO-2010/006080 | 1/2010 |
| WO | WO-2010/115904 A1 | 10/2010 |
| WO | WO-2011/019686 A1 | 2/2011 |
| WO | WO-2011/046706 A1 | 4/2011 |
| WO | WO-2011/001674 | 6/2011 |
| WO | WO-2011/063458 A1 | 6/2011 |
| WO | WO-2011/075158 | 6/2011 |
| WO | WO-2011/094204 A2 | 8/2011 |
| WO | WO-2011/100458 A2 | 8/2011 |
| WO | WO-2011/138689 A2 | 11/2011 |
| WO | WO-2012/006657 A1 | 1/2012 |
| WO | WO-2012/021801 A2 | 2/2012 |
| WO | WO-2012/027148 A1 | 3/2012 |
| WO | WO-2012/028695 | 3/2012 |
| WO | WO-2012/030368 A1 | 3/2012 |
| WO | WO-2012/125770 | 9/2012 |
| WO | WO-2012/138671 A2 | 10/2012 |

(56) References Cited

FOREIGN PATENT DOCUMENTS

| WO | WO-2012/142852 A1 | 10/2012 |
|---|---|---|
| WO | WO-2013/016445 A1 | 1/2013 |
| WO | WO-2013/048063 A1 | 4/2013 |
| WO | WO-2013/138137 A1 | 9/2013 |
| WO | WO-2013/138698 A1 | 9/2013 |
| WO | WO-2013/151799 | 10/2013 |
| WO | WO-2013/152179 A1 | 10/2013 |
| WO | WO-2014/084856 | 6/2014 |
| WO | WO-2014/084861 A1 | 6/2014 |
| WO | WO-2014/168629 A1 | 10/2014 |
| WO | WO-2015/030698 A1 | 3/2015 |
| WO | WO-2015/110277 | 7/2015 |
| WO | WO-2015/138736 A1 | 9/2015 |
| WO | WO-2015/138752 A1 | 9/2015 |
| WO | WO-2015/1138771 A1 | 9/2015 |
| WO | WO-2015/197217 | 12/2015 |
| WO | WO-2016/102003 | 6/2016 |

OTHER PUBLICATIONS

Nair et al. "Unimpeded permeation of water through helium-leak-tight graphene-based membranes". Science, Jan. 27, 2012, vol. 335. p. 442-444 (Year: 2012).*
Notice of Allowance for U.S. Appl. No. 14/819,273 dated Oct. 28, 2016.
U.S. Office Action for U.S. Appl. No. 14/193,007 dated Oct. 21, 2016.
U.S. Office Action for U.S. Appl. No. 14/193,007 dated Dec. 21, 2015.
U.S. Office Action for U.S. Appl. No. 14/193,007 dated Jul. 1, 2016.
Chen et al., "Hierarchically porous graphene-based hybrid electrodes with excellent electrochemical performance", Journal of Materials Chemistry A: Materials for Energy and Sustainability, vol. 1, No. 33, Jan. 1, 2013, pp. 9409-9413.
Chinese Office Action in Application No. 201580006829.5 dated Jan. 23, 2018 (with English translation) (13 pages)
European Extended Search Report in Application No. 15786691.4 dated Dec. 1, 2017 (10 pages).
European Extended Search Report in Application No. 15789852.9 dated Dec. 6, 2017 (8 pages).
Japanese Office Action in Application No. 2017-042023 dated Jan. 9, 2018 (with English translation) (9 pages).
Singapore Search Report and Written Opinion in Application No. 11201701654U dated Dec. 6, 2017 (6 pages).
Taiwanese Office Action in Application No. 102146079 dated Dec. 12, 2017 (with English translation) (4 pages).
U.S. Notice of Allowance in U.S. Appl. No. 14/843,944 dated Feb. 9, 2018 (9 pages).
U.S. Office Action for U.S. Appl. No. 15/099,482 dated Feb. 23, 2018 (9 pages).
U.S. Office Action in U.S. Appl. No. 14/609,325 dated Jan. 16, 2018 (11 pages).
U.S. Office Action in U.S. Appl. No. 14/656,190 dated Jan. 10, 2018 (14 pages).
U.S. Office Action in U.S. Appl. No. 14/856,471 dated Jan. 11, 2018 (36 pages).
U.S. Office Action in U.S. Appl. No. 15/099,099 dated Feb. 15, 2018 (13 pages).
U.S. Office Action in U.S. Appl. No. 15/099,588 dated Feb. 1, 2018 (6 pages).
Wang et al., "Preparation of high-surface-area carbon nanoparticle/graphene composites", Carbon, Elsevier, Oxford, GB, vol. 50, No. 10, Apr. 8, 2012, pp. 3845-3853.
AE Search and Examination Report for United Arab Emirates Application No. P186/13 dated Oct. 4, 2016.
Agenor et al., "Renal tubular dysfunction in human visceral leishmaniasis (Kala-azar)," Clinical Nephrology 71(5): 492-500 (May 2009) (available online Mar. 21, 2011).
Albert et al., "Ringer's lactate is compatible with the rapid infusion of AS-3 preserved packed red blood cells," Can. J. Anaesth. 56(5): 352-356 (May 2009) (available online Apr. 2, 2009).
Aluru et al. "Modeling electronics on the nanoscale." Handbook of nanoscience, engineering and technology Goddard W, Brenner D, Lyshevski S, Iafrate GJ (2002): 11-1.
Alvarenga, "Carbon nanotube materials for aerospace wiring" Rochester Institute of Technology, 2010.
AMI Applied Membranes Inc., "Filmtec Nanofiltration Membrane Elements", Retrieved from appliedmembranes.com/nanofiltration_elements.htm, accessed Apr. 28, 2015 (2 Pages).
Aso et al., "Comparison of serum high-molecular weight (HMW) adiponectin with total adiponectin concentrations in type 2 diabetic patients with coronary artery using a novel enzyme-linked immunosorbent assay to detect HMW adiponectin," Diabetes 55(7): 1954-1960 (Jul. 2006).
AU Examination Report for Australian Patent Application No. 2013235234, dated Jan. 13, 2017, 4 pages.
AU Examination Report for Australian Patent Application No. 2013363283, dated Jun. 20, 2017, 4 pages.
AU Notice of Acceptance for Australian Application No. 2011293742 dated Jan. 13, 2016.
Axelsson et al., "Acute hyperglycemia induces rapid, reversible increases in glomerular permeability in nondiabetic rats," Am. J. Physiol. Renal Physiol. 298(6): F1306-F1312 (Jun. 2010) (available online Mar. 17, 2010).
Bains et al., "Novel lectins from rhizomes of two *Acorus* species with mitogenic activity and inhibitory potential towards murine cancer cell lines," Int'l Immunopharmacol. 5(9): 1470-1478 (Aug. 2005) (available online May 12, 2005).
Baker, "Membrane Technology and Applications", Membrane Technology and Applications; Apr. 14, 2004; pp. 92-94.
Barreiro et al. "Transport properties of graphene in the high-current limit." Physical review letters 103.7 (2009): 076601.
Bazargani et al. "Low molecular weight heparin improves peritoneal ultrafiltration and blocks complement and coagulation," Peritoneal Dialysis Int'l 25(4): 394-404 (Jul. 2005-Aug. 2005).
Bazargani, "Acute inflammation in peritoneal dialysis: experimental studies in rats. Characterization of regulatory mechanisms," Swedish Dental J. Supp. 171: 1-57, i (2005).
Beppu et al., "Antidiabetic effects of dietary administration of Aloe arborescens Miller components on multiple low-dose streptozotocin-induced diabetes in mice: investigation on hypoglycemic action and systemic absorption dynamics of aloe components," J. Ethnopharmacol. 103(3): 468-77 (Feb. 20, 2006) (available online Jan. 6, 2006).
Bieri et al. "Two-dimensional Polymer Formation on Surfaces: Insight into the Roles of Precursor Mobility and Reactivity" JACS, 2010, vol. 132, pp. 16669-16676.
Bruin et al., "Maturation and function of human embryonic stem cell-derived pancreatic progenitors in macroencapsulation devices following transplant into mice", Diabetologia (2013), vol. 56: 1987-1998 (Jun. 16, 2013).
Chu Ju, et al. "Modern Biotechnology" East China University of Technology Press, (Sep. 2007), vol. 1; pp. 306-307, ISBN 978-7-5628-2116-8.
Clochard, "Track-Etched Polymer Membranes," Laboratory of Irradiated Solids, Ecole Polytechnique, retrieved from http://www.lsi.polytechnique.fr/home/research/physics-and-chemistry-of-nano-objects/trac . . . , Accessed Jul. 30, 2015 (2 pages).
CN Notification of Grant for Chinese Application No. 201180049184.5 dated Jun. 6, 2016.
CN Office Action for Chinese Application No. 201380014845.X dated Jul. 8, 2016.
CN Office Action for Chinese Application No. 201380014845.X dated Sep. 2, 2015.
CN Office Action for Chinese Application No. 201380019165.5 dated Aug. 25, 2015.
CN Office Action for Chinese Application No. 201380073141.X dated Jun. 8, 2016.
CN Office Action for Chinese Application No. 201380073141.X dated Mar. 21, 2017.
CN Office Action for Chinese Application No. 201480015372.X dated Aug. 2, 2016.

(56) References Cited

OTHER PUBLICATIONS

CN Office Action for Chinese Application No. 20118004918.5 dated Jun. 15, 2015.
CN Office Action for Chinese Application No. 201180049184.5 dated Jul. 30, 2014.
CN Office Action for Chinese Application No. 201180049184.5 dated Mar. 4, 2016.
CN Office Action for Chinese Application No. 201380014845.X dated Dec. 23, 2016.
CN Office Action for Chinese Application No. 201380017644.5 dated Feb. 7, 2017.
CN Office Action for Chinese Application No. 201380017644.5 dated May 26, 2016.
CN Office Action for Chinese Application No. 201380017644.5 dated Sep. 29, 2015.
CN Office Action in Chinese Application No. 201380013988.9 dated Oct. 27, 2015.
Daniel et al. "Implantable Diagnostic Device for Cancer Monitoring." Biosens Bioelectricon. 24(11): 3252-3257 (Jul. 15, 2009).
Database WPI, Week 201238, Thomson Scientific, London, GB; AN 2012-D49442.
De Lannoy et al., "Aquatic Biofouling Prevention by Electrically Charged Nanocomposite Polymer Thin Film Membranes", 2013 American Water Work Association membrane Technology Conference; Environmental science & technology 47.6 (2013): 2760-2768.
Deng et al., "Renal protection in chronic kidney disease: hypoxia-inducible factor activation vs. angiotensin II blockade," Am. J. Physiol. Renal Physiol. 299(6): F1365-F1373 (Dec. 2010) (available online Sep. 29, 2010).
Edwards, "Large Sheets of Graphene Film Produced for Transparent Electrodes (w/ Video)"; (Jun. 21, 2010), PhysOrg.com, retrieved on May 15, 2017 from https://phys.org/news/2010-06-large-sheets-graphene-transparentelectrodes.html (2 pages).
EP Office Action for European Application No. 13715529.7 dated Jun. 24, 2016.
Fayerman, "Canadian scientists use stem cells to reverse diabetes in mice", The Telegraph-Journal (New Brunswick), 1-2 (Jun. 29, 2012).
Fayerman, "Diabetes reversed in mice; University of B.C. scientists use embryonic stem cells to deal with Type 1 disease", The Vancouver Sun (British Columbia), 1-2 (Jun. 28, 2012).
Fejes et al. "A review of the properties and CVD synthesis of coiled carbon nanotubes." Materials 3.4 (2010): 2618-2642.
Franzen, C. "MIT Setting Up Industrial-Scale Graphene Printing Press" Sep. 23, 2011, retrieved from http://talkingpointsmemo.com/idealab/mit-setting-up-industrial-scale-graphene-printing-press (2 pages).
Freedman et al., "Genetic basis of nondiabetic end-stage renal disease," Semin. Nephrol. 30(2): 101-110 (Mar. 2010).
Garcia-Lopez et al., "Determination of high and low molecular weight molecules of icodextrin in plasma and dialysate, using gel filtration chromatography, in peritoneal dialysis patients," Peritoneal Dialysis Int'l 25(2): 181-191 (Mar. 2005-Apr. 2005).
Georgakilas et al., "Functionalization of Graphene: Covalent and Non-Covalent Approaches, Derivatives and Applications," Chem. Rev., (2012) 112(11), pp. 6156-6214.
Gnudi "Molecular mechanisms of proteinuria in diabetes," Biochem. Soc. Trans. 36(5): 946-949 (Oct. 2008).
Gotloib et al., "Peritoneal dialysis in refractory end-stage congestive heart failure: a challenge facing a no-win situation," Nephrol. Dialysis. Transplant. 20(Supp. 7): vii32-vii36 (Jul. 2005).
Harvey "Carbon as conductor: a pragmatic view." Proceedings of the 61st IWCS Conference, http://www. iwcs. org/archives/56333-iwcs-2012b-1.1584632. vol. 1. 2012.
Hashimoto et al. "Direct evidence for atomic defects in graphene layers." Nature 430.7002 (2004): 870-873.
He, et al. "The attachment of $Fe_3O_4$ nanoparticles to graphene oxide by covalent bonding." Carbon 48.11 (2010): 3139-3144.
Hone et al. "Graphene has record-breaking strength" Physicsworld.com, Jul. 17, 2008.

Huang et al., "Gene expression profile in circulating mononuclear cells afterexposure to ultrafine carbon particles," Inhalation Toxicol. 22(10): 835-846 (Aug. 2010).
Humplik, et al. "Nanostructured materials for water desalination." Nanotechnology 22.29 (2011): 292001.
International Search Report and Written Opinion dated Jan. 5, 2012 for related International Application No. PCT/US11/47800.
International Search Report and Written Opinion dated Jul. 5, 2017 from related PCT application PCT/US2017/024147.
International Search Report and Written Opinion dated Mar. 12, 2014 for International Application No. PCT/US2013/074942.
International Search Report and Written Opinion for International Application No. PCT/US2011/047800 dated Jan. 5, 2012.
International Search Report and Written Opinion for PCT Application No. PCT/US2014/023027 dated Jun. 26, 2014.
International Search Report and Written Opinion in International Application No. PCT/US2013/030344 dated Jun. 19, 2013.
International Search Report and Written Opinion in International Application No. PCT/US2013/033035 dated Jun. 28, 2013.
International Search Report and Written Opinion in International Application No. PCT/US2013/033400, dated Jun. 28, 2013.
International Search Report and Written Opinion in International Application No. PCT/US2013/033403 dated Jun. 28, 2013.
International Search Report and Written Opinion in PCT/US2014/041766, dated Sep. 30, 2014.
International Search Report and Written Opinion dated Jun. 5, 2014 in International Application No. PCT/US2014/021677.
International Search Report and Written Opinion dated Jun. 6, 2014 in International Application No. PCT/US2014/023043.
International Search Report and Written Opinion dated Dec. 16, 2014, for International Application No. PCT/US2014/051011.
International Search Report and Written Opinion dated Jun. 19, 2015, in International Application No. PCT/US2015/020287.
Inui et al. "Molecular dynamics simulations of nanopore processing in a graphene sheet by using gas cluster ion beam." Applied Physics A: Materials Science & Processing 98.4 (2010): 787-794.
Israelachvili, "Intermolecular and Surface Forces," 3rd ed., Chap. 7.1, Sizes of Atoms, Molecules, and Ions, 2011, 1 page.
Jiao et al., "Castration differentially alters basal and leucine-stimulated tissue protein synthesis in skeletal muscle and adipose tissue," Am. J. Physiol. Endocrinol. Metab. 297(5): E1222-1232 (Nov. 2009) (available online Sep. 15, 2009).
JP Office Action in Japanese Application No. 2015-501729 dated Dec. 9, 2016 (English translation).
JP Office Action in Japanese Application No. 2015-501729 dated Jun. 20, 2017 (English translation).
JP Office Action in Japanese Application No. 2015-501867 dated Oct. 11, 2016 (English translation).
JP Office Action in Japanese Application No. 2015-503405 dated Nov. 14, 2016 (English translation).
JP Office Action in Japanese Application No. 2015-503406 dated Dec. 6, 2016(English translation).
Kang et al., "Effect of eplerenone, enalapril and their combination treatment on diabetic nephropathy in type II diabetic rats," Nephrol. Dialysis Transplant. 24(1): 73-84 (Jan. 2009).
Kang et al., "Efficient Transfer of Large-Area Graphene Films onto Rigid Substrates by Hot Pressing," American Chemical Society Nano, 6(6): 5360-5365(May 28, 2012).
Kar et al., "Effect of glycation of hemoglobin on its interaction with trifluoperazine," Protein J. 25(3): 202-211 (Apr. 2006) (available online Jun. 6, 2006).
Kawamoto et al., "Serum high molecular weight adiponectin is associated with mild renal dysfunction in Japanese adults," J. Atherosclerosis Thrombosis 17(11): 1141-1148 (Nov. 27, 2011).
Khun et al. "From Microporous Regular Frameworks to Mesoporous Materials with Ultrahigh Surface Area: Dynamic reorganization of Porous Polymer Networks" JACS, 2008; vol. 130; pp. 13333-13337.
Krupka et al., "Measurements of the Sheet Resistance and Conductivity of Thin Epitaxial Graphene and SiC Films" Applied Physics Letters 96, 082101-I; Feb. 23, 2010.

(56) References Cited

OTHER PUBLICATIONS

Kumar et al., "Modulation of alpha-crystallin chaperone activity in diabetic rat lens by curcumin," Molecular Vision 11: 561-568 (Jul. 26, 2005).
Lathuiliere et al., "Encapsulated Cellular Implants for Recombinant Protein Delivery and Therapeutic Modulation of the Immune System," Journal of Applied Physics, Int. J. Mol. Sci., 16: 10578-10600 (May 8, 2015).
Lee, et al. "Measurement of the elastic properties and intrinsic strength of monolayer graphene." science 321.5887 (2008): 385-388.
Lucchese et al. "Quantifying ion-induced defects and Raman relaxation length in graphene." Carbon 48.5 (2010): 1592-1597.
MacLeod et al. "Supramolecular Orderinng in Oligothiophene-Fullerene Monolayers" JACS, 2009, vol. 131, pp. 16844-16850.
Mattevi et al. "A review of chemical vapour deposition of graphene on copper." Journal of Materials Chemistry 21.10 (2011): 3324-3334.
Miao et al. "Chemical vapor deposition of grapheme" INTECH Open Access Publisher, 2011.
MIT/MTL Center for Graphene Devices and 2D Systems, retrieved from: http://www-mtl.mit.edu/wpmu/graphene/ [retrieved from Aug. 21, 2014 archive] (3 pages).
MIT/MTL Center for Graphene Devices and 2D Systems, retrieved from: http://www-mtl.mit.edu/wpmu/graphene/ [retrieved from Mar. 4, 2015 archive] (3 pages).
Nafea, et al. "Immunoisolating semi-permeable membranes for cell encapsulation: focus on hydrogels." J Control Release. 154(2): 110-122 (Sep. 5, 2011).
Nezlin, "Circulating non-immune IgG complexes in health and disease," Immunol. Lett. 122(2); 141-144 (Feb. 21, 2009) (available online Feb. 2, 2009).
Norata et al., "Plasma adiponectin levels in chronic kidney disease patients: relation with molecular inflammatory profile and metabolic status," Nutr. Metab. Cardiovasc. Dis. 20(1): 56-63 (Jan. 2010) (available online Apr. 9, 2009).
Ogawa et al., "Exosome-like vesicles in Gloydius blomhoffii blomhoffii venom," Toxicon 51(6): 984-993 (May 2008) (available online Feb. 19, 2008).
Ohgawara et al. "Assessment of pore size of semipermeable membrane for immunoisolation on xenoimplatntation of pancreatic B cells using a diffusion chamber." Transplant Proc. (6): 3319-3320. 1995.
Oki et al., "Combined acromegaly and subclinical Cushing disease related to high-molecular-weight adrenocorticotropic hormone," J. Neurosurg. 110(2): 369-73 (Feb. 2009).
Osorio et al., "Effect of treatment with losartan on salt sensitivity and SGLT2 expression in hypertensive diabetic rats," Diabetes Res. Clin. Pract. 86(3): e46-e49 (Dec. 2009) (available online Oct. 2, 2009).
Osorio et al., "Effect of phlorizin on SGLT2 expression in the kidney of diabetic rats," J. Nephrol. 23(5): 541-546 (Sep.-Oct. 2010).
Padidela et al., "Elevated basal and post-feed glucagon-like peptide 1 (GLP-1) concentrations in the neonatal period," Eur. J. Endocrinol. 160(1): 53-58 (Jan. 2009) (available online Oct. 24, 2008).
Pall Corporation, "Pall Water Processing Disc-Tube Filter Technology", Retrieved on Feb. 10, 2015, Retrieved from http://www.pall.com /pdfs/Fuels-and-Chemicals/Disc-Tube_Filter_Technoloqy-DT100b.pdF (15 Pages).
Plant et al. "Size-dependent propagation of Au nanoclusters through few-layer grapheme," The Royal Society of Chemistry 2013, Nanoscale.
Pollard, "Growing Graphene via Chemical Vapor" Department of Physics, Pomona College; May 2, 2011.
Rafael et al. "Cell Transplantation and Immunoisolation: Studies on a macroencapsultaion device." From the Departments of Transplantation Pathology: Stockholm, Sweden (1999).
Rezania et al., "Enrichment of Human Embryonic Stem Cell-Derived NKX6.1-Expressing Pancreatic Progenitor Cells Accelerates the Maturation of Insulin-Secreting Cells In Vivo", Stem Cells Regenerative Medicine, vol. 31: 2432-2442 (Jul. 29, 2013).
Rezania et al., "Maturation of Human Embryonic Stem Cell-Derived Pancreatic Progenitors Into Functional Islets Capable of Treating Pre-existing Diabetes in Mice", Diabetes Journal, vol. 61: 2016-2029 (Aug. 1, 2012).
Ribeiro et al., "Binary Mutual Diffusion Coefficients of Aqueous Solutions of Sucrose, Lactose, Glucose, and Fructose in the Temperature Range from (298.15 to 328.15) K," J. Chem. Eng. Data 51(5): 1836-1840 (Sep. 2006) (available online Jul. 20, 2006).
Rippe et al., "Size and charge selectivity of the glomerular filter in early experimental diabetes in rats," Am. J. Physiol. Renal Physiol. 293(5): F1533-F1538 (Nov. 2007)(available online Aug. 15, 2007).
SA Final Rejection for Saudi Arabia Application No. 113340400 dated Jan. 28, 2016.
SA First Examination Report for Saudi Arabia Application No. 113340401 dated Apr. 28, 2015.
SA First Examination Report for Saudi Arabia Application No. 113340424 dated May 10, 2015.
SA First Examination Report for Saudi Arabia Application No. 113340426 dated May 12, 2015.
SA First Examination Report in Saudi Arabia Application No. 113340400 dated Apr. 13, 2015.
SA Second Examination Report for Saudi Arabia Application No. 113340400 dated Aug. 11, 2015.
Sanchez, et al. "Biological Interactions of Graphene-Family Nanomaterials—An Interdisciplinary Review." Chem Res Toxicol. 25(1): 15-34 (Jan. 13, 2012).
Sethna et al., "Serum adiponectin levels and ambulatory blood pressure monitoring in pediatric renal transplant recipients," Transplantation 88(8): 1030-1037 (Oct. 27, 2009).
Sullivan et al., "Microarray analysis reveals novel gene expression changes associated with erectile dysfunction in diabetic rats," Physiol. Genom. 23(2): 192-205 (Oct. 17, 2005) (available online Aug. 23, 2005).
Swett et al, "Imagining and Sculpting Graphene on the atomic scale" Oak Ridge National Laboratory's (ORNL) Center for Nanophase Materials Sciences (CNMS) Biannual Review. 1 page.
Swett et al, "Supersonic Nanoparticle Interaction with Suspended CVD Graphene", Microsc. Microanal. 22 (Suppl 3): 1670-1671 (Jul. 25, 2016).
Takata et al., "Hyperresistinemia is associated with coexistence of hypertension and type 2 diabetes," Hypertension 51. 2 (Feb 2008): 534-9.
Tamborlane et al., "Continuous Glucose Monitoring and Intensive Treatment of Type 1 Diabetes" N. Engl J Med 359;14: 1464-1476 (Oct. 2, 2008).
Tanugi et al., "Nanoporous Graphene Could Outperform Best Commercial Water Desalination Techniques," ; ACS 2012; Jun. 25, 2012; Weftec 2012; Sep. 29-Oct. 3.
Totani et al. "Gluten binds cytotoxic compounds generated in heated frying oil." Journal of oleo science 57.12 (2008): 683-690.
Tsukamoto et al. "Purification, characterization and biological activities of a garlic oliqosaccharide," Journal of UOEH 30. 2 (Jun. 1, 2008): 147-57.
TW Office Action in Taiwanese Application No. 102146079 dated Apr. 14, 2017. 9 Pages.(English translation).
TW Search Report in Taiwanese Application No. 102146079 dated Apr. 14, 2017. 1 page.
UMEA Universitet "Graphene nanoscrolls are formed by decoration of magnetic nanoparticles." ScienceDaily. Aug. 15, 2013. https://www.sciencedaily.com/releases/2013/08/130815084402.htm (3 pages).
U.S. Corrected Notice of Allowance in U.S. Appl. No. 14/819,273 dated Apr. 12, 2017.
U.S. Notice of Allowance for U.S. Appl. No. 12/868,150 dated Sep. 25, 2012.
U.S. Notice of Allowance for U.S. Appl. No. 13/548,539 dated Aug. 18, 2015.
U.S. Notice of Allowance for U.S. Appl. No. 13/548,539 dated Jul. 23, 2015.
U.S. Notice of Allowance for U.S. Appl. No. 13/719,579 dated May 20, 2016.

(56) References Cited

OTHER PUBLICATIONS

U.S. Notice of Allowance for U.S. Appl. No. 13/795,276 dated Oct. 7, 2016.
U.S. Notice of Allowance for U.S. Appl. No. 13/802,896 dated Apr. 1, 2015.
U.S. Notice of Allowance for U.S. Appl. No. 13/803,958 dated Aug. 29, 2016.
U.S. Notice of Allowance for U.S. Appl. No. 13/803,958 dated Jun. 2, 2016.
U.S. Notice of Allowance for U.S. Appl. No. 13/803,958 dated Sep. 12, 2016.
U.S. Notice of Allowance for U.S. Appl. No. 13/804,085 dated Jan. 15, 2015.
U.S. Notice of Allowance for U.S. Appl. No. 13/804,085 dated Mar. 12, 2015.
U.S. Notice of Allowance for U.S. Appl. No. 13/923,503 dated Oct. 14, 2016.
U.S. Notice of Allowance for Application No. 13/923,503 dated Oct. 5, 2016.
U.S. Notice of Allowance for U.S. Appl. No. 14/200,195 dated Jul. 5, 2016.
U.S. Notice of Allowance for U.S. Appl. No. 14/200,530 dated Aug. 1, 2016.
U.S. Notice of Allowance for U.S. Appl. No. 14/203,655 dated Dec. 9, 2016.
U.S. Notice of Allowance in U.S. Appl. No. 12/868,150 dated Sep. 25, 2012.
U.S. Notice of Allowance in U.S. Appl. No. 13/795,276 dated Jan. 19, 2017.
U.S. Notice of Allowance in U.S. Appl. No. 13/803,958 dated Aug. 29, 2016.
U.S. Notice of Allowance in U.S. Appl. No. 13/803,958 dated Sep. 12, 2016.
U.S. Notice of Allowance in U.S. Appl. No. 14/610,770 dated May 5, 2017.
U.S. Notice of Allowance in U.S. Appl. No. 14/656,580 dated May 8, 2017.
U.S. Notice of Allowance in U.S. Appl. No. 14/819,273 dated Jun. 9, 2017.
U.S. Notice of Allowance in U.S. Appl. No. 15/099,464 dated Jun. 16, 2017.
U.S. Office Action for U.S. Appl. No. 13/548,539 dated Feb. 6, 2015.
U.S. Office Action for U.S. Appl. No. 13/719,579 dated Jul. 8, 2015.
U.S. Office Action for U.S. Appl. No. 13/719,579 dated May 4, 2016.
U.S. Office Action for U.S. Appl. No. 13/795,276 dated Apr. 22, 2016.
U.S. Office Action for U.S. Appl. No. 13/795,276 dated Oct. 6, 2015.
U.S. Office Action for U.S. Appl. No. 13/802,896 dated Sep. 24, 2014.
U.S. Office Action for U.S. Appl. No. 13/803,958 dated Aug. 11, 2014.
U.S. Office Action for U.S. Appl. No. 13/803,958 dated May 28, 2015.
U.S. Office Action for U.S. Appl. No. 13/803,958 dated Nov. 18, 2015.
U.S. Office Action for U.S. Appl. No. 13/923,503 dated Mar. 22, 2016.
U.S. Office Action for U.S. Appl. No. 14/031,300 dated Jan. 20, 2016.
U.S. Office Action for U.S. Appl. No. 14/031,300 dated Jul. 7, 2015.
U.S. Office Action for U.S. Appl. No. 14/200,195 dated Mar. 21, 2016.
U.S. Office Action for U.S. Appl. No. 14/200,195 dated Nov. 4, 2015.
U.S. Office Action for U.S. Appl. No. 14/200,530 dated Feb. 29, 2016.
U.S. Office Action for U.S. Appl. No. 14/203,655 dated Aug. 10, 2016.
U.S. Office Action for U.S. Appl. No. 14/656,190 dated May 18, 2017.
U.S. Office Action for U.S. Appl. No. 14/656,657 dated Jul. 7, 2017.
U.S. Office Action for U.S. Appl. No. 14/686,452 dated Jun. 9, 2017.
U.S. Office Action for U.S. Appl. No. 14/843,944 dated Jun. 23, 2017.
U.S. Office Action for U.S. Appl. No. 14/856,471 dated May 31, 2017.
U.S. Office Action for U.S. Appl. No. 14/858,741 dated Dec. 1, 2016.
U.S. Office Action for U.S. Appl. No. 15/289,944 dated Feb. 9, 2017.
U.S. Office Action for U.S. Appl. No. 15/336,545 dated Dec. 19, 2016.
U.S. Office Action for U.S. Appl. No. 15/453,441 dated Jun. 5, 2017.
U.S. Office Action in U.S. Appl. No. 14/193,007 dated Apr. 24, 2017.
U.S. Office Action in U.S. Appl. No. 14/656,617 dated Apr. 4, 2017.
U.S. Office Action on U.S. Appl. No. 14/656,335 dated Apr. 25, 2017.
U.S. Office Action on U.S. Appl. No. 15/332,982 dated Jan. 30, 2017.
U.S. Supplemental Notice of Allowance for U.S. Appl. No. 13/795,276 dated Nov. 29, 2016.
Vallon,"Micropuncturing the nephron," Pflugers Archiv : European journal of physiology 458. 1 (May 2009): 189-201.
Van Der Zande et al. "Large-scale arrays of single-layer graphene resonators." Nano letters 10.12 (2010): 4869-4873.
Verdonck, P., "Plasma Etching", in Oficina de Microfabricao: Projeto e Construcao de CI's MOS, Swart, J.W., Ed., Campinas (Sao Paulo, Brazil): UNICAMP, 2006, ch. 10, p. 9.
Vlassiouk et al. "Large scale atmospheric pressure chemical vapor deposition of graphene." Carbon 54 (2013): 58-67.
Vriens et al. "Methodological considerations in quantification of oncological FDG PET studies." European journal of nuclear medicine and molecular imaging 37.7 (2010): 1408-1425.
Wang et al., "Direct Observation of a Long-Lived Single-Atom Catalyst Chiseling Atomic Structures in Graphene," Nano Lett., 2014, pp. A-F.
Wang et al., "Porous Nanocarbons: Molecular Filtration and Electronics," Advances in Graphene Science, Edited by Mahmood Aliofkhazraei, (2013) ISBN 978-953-51-1182-5, Publisher: InTech; Chapter 6, pp. 119-160.
Wang et al.,"What is the role of the second "structural "NADP+-binding site in human glucose 6-phosphate dehydrogenase?," Protein science a publication of the Protein Society 17. 8 (Aug. 2008): 1403-11.
Wei et al., "Synthesis of N-doped graphene by chemical vapor deposition and its electrical properties", Nano Lett. 2009 9 1752-58.
Xiaogan Liang et al., Formation of Bandgap and Subbands in Graphene Nanomeshes with Sub-10nm Ribbon Width Fabricated via Nanoimprint Lithography., Nano Letters, Jun. 11, 2010, pp. 2454-2460.
Xie et al., "Fractionation and characterization of biologically-active polysaccharides from Artemisia tripartite," Phytochemistry 69. 6 (Apr. 2008): 1359-71.
Xie, et al. "Controlled fabrication of high-quality carbon nanoscrolls from monolayer graphene." Nano letters 9.7 (2009): 2565-2570.
Yagil et al. "Nonproteinuric diabetes-associated nephropathy in the Cohen rat model of type 2 diabetes" Diabetes 54. 5 (May 2005): 1487-96.
Zan et al. "Interaction of Metals with Suspended Graphene Observed by Transmission Electron Microscopy", J. Phys. Chem. Lett., Mar. 8, 2012, 3, 953-958.
Zhang et al. "Effect of Chemical Oxidation on the Structure of Single-Walled Carbon Nanotubes", J. Phys. Chem., Feb. 12, 2003, B 107 3712-8.

(56) References Cited

OTHER PUBLICATIONS

Zhang et al. "Method for anisotropic etching of graphite or graphene" Institute of Physics, Chinese Academy of Sciences; Peop. Rep. China; Mar. 30, 2011.
Zhang et al. "Production of Graphene Sheets by Direct Dispersion with Aromatic Healing Agents", Small, May 6, 2010, vol. 6, No. 10, 1100-1107.
Zhang et al. "Isolation and activity of an alpha-amylase inhibitor from white kidney beans," Yao xue xue bao =Acta pharmaceutica Sinica 42. 12 (Dec. 2007): 1282-7.
Zhao, et al. "Efficient preparation of large-area graphene oxide sheets for transparent conductive films." ACS nano 4.9 (2010): 5245-5252.
Zhou, K., et al., "One-pot preparation of graphene/ Fe304 composites by a solvothermal reaction," New J. Chem., 2010, 34, 2950.
Zhu et al. "Carbon Nanotubes in Biomedicine and Biosensing", Carbon Nanotubes—Growth and Applications, InTech, (Aug. 9, 2011) Chapter 6: pp. 135-162. Available from: https://www.intechopen.com/books/carbon-nanotubes-growth-and-applications/carbon-nanotubes-in-biomedicine-and-biosensing.
Ziegelmeier et al. "Adipokines influencing metabolic and cardiovascular disease are differentially regulated in maintenance hemodialysis," Metabolism: clinical and experimental 57. 10 (Oct. 2008): 1414-21.
Zirk et al. "A refractometry-based glucose analysis of body fluids," Medical engineering & physics 29. 4 (May 2007): 449-58.
Zyga "Nanoporous Graphene Could Outperform Best Commercial Water Desalination Techniques," Phys.org., Jun. 22, 2012, Retrieved from http://www.phys.org/pdf259579929.pdf [Last Accessed Dec. 3, 2014] (3 pages).
EPO Extended Search Report for European Application No. 171684883.5 dated Jul. 25, 2017 (8 pages).
EPO Supplementary Search Report for European Application No. 15762019.6 dated Aug. 9, 2017 (16 pages).
U.S. Notice of Allowance in U.S. Appl. No. 14/610,770 dated Sep. 26, 2017. (12 pages).
U.S. Notice of Allowance in U.S. Appl. No. 15/332,982 dated Sep. 21, 2017. (5 pages).
U.S. Office Action in U.S. Appl. No. 15/099,099 dated Oct. 5, 2017 (11 pages).
U.S. Office Action in U.S. Appl. No. 15/099,447 dated Oct. 3, 2017 (21 pages).
Weisen, et al., "Fabrication of nanopores in a graphene sheet with heavy ions: A molecular dynamics study", Journal of Applied Physics 114, 234304 (2013), pp. 234304-1 to 234304-6.
Adiga et al., "Nanoporous Materials for Biomedical Devices," JOM 60: 26-32 (Mar. 25, 2008).
AMI Applied Membranes Inc. (undated). FilmTec Nanofiltration Membrane Elements. Retrieved Jun. 1, 2016, from http://www.appliedmembranes.com/filmtec-nanofiltration-membrane-elements.html.
Apel, "Track etching technique in membrane technology," Radiation Measurements 34(1-6): 559-566 (Jun. 2001).
Bae et al., "Roll-to-roll production of 30-inch graphene films for transparent electrodes," Nature Nanotechnology 5: 574-578 (Jun. 20, 2010).
Bai et al., "Graphene nanomesh," Nature Nanotechnology 5: 190-194 (Feb. 14, 2010).
Baker. (2004). "Track-etch Membranes." In Membrane Technology and Applications (2nd ed., pp. 92-94). West Sussex, England: John Wiley & Sons.
Butler et al. "Progress, Challenges, and Opportunities in Two-Dimensional Materials Beyond Graphene", Materials Review 7(4): 2898-2926 (Mar. 6, 2013).
Chhowalla et al., "The chemistry of two-dimensional layered transition metal dichalcogenide nanosheets," Nature Chemistry 5: 263-275 (Mar. 20, 2013).
Childres et al., "Effect of oxygen plasma etching on graphene studied using Raman spectroscopy and electronic transport measurements," New Journal of Physics 13 (Feb. 10, 2011).
Clochard. (undated). Radiografted track-etched polymer membranes for research and application [Scholarly project]. In Laboratoire Des Solides Irradiés. Retrieved Jun. 2, 2016, from http://iramis.cea.fr/radiolyse/5juin2015/Clochard.pdf.
Cohen-Tanugi et al, "Water Desalination across Nanoporous Graphene," ACS Nano Letters 12(7): 3602-3608 (Jun. 5, 2012).
Cohen-Tanugi, "Nanoporous graphene as a water desalination membrane," Thesis: Ph.D., Massachusetts Institute of Technology, Department of Materials Science and Engineering (Jun. 2015).
Colton, "Implantable biohybrid artificial organs," Cell Transplantation 4(4): 415-436 (Jul.-Aug. 1995).
Desai et al., "Nanoporous microsystems for islet cell replacement," Advanced Drug Delivery Reviews 56: 1661-1673 (Jul. 23, 2004).
Fischbein et al., "Electron beam nanosculpting of suspended graphene sheets," Applied Physics Letters 93(113107): 1-3, (Sep. 16, 2008).
Fissell et al., "High-Performance Silicon Nanopore Hemofiltration Membranes," NIH-PA Author Manuscript, PMC, (Jan. 5, 2010), also published in J. Memb. Sci. 326(1): 58-63 (Jan. 5, 2009).
Gimi et al., "A Nanoporous, Transparent Microcontainer for Encapsulated Islet Therapy," J. Diabetes Sci. Tech. 3(2): 1-7 (Mar. 2009).
International Search Report dated Dec. 4, 2015, in related international application PCT/US2015/048205.
International Search Report dated Jun. 10, 2015, from related international application PCT/US15/20201.
Jiang et al., "Porous Graphene as the Ultimate Membrane for Gas Separation," Nano Letters 9(12): 4019-4024 (Sep. 23, 2009).
Joshi et al., "Precise and ultrafast molecular sieving through graphene oxide membranes", Science 343(6172): 752-754 (Feb. 14, 2014).
Kanani et al., "Permeability-Selectivity Analysis for Ultrafiltration: Effect of Pore Geometry," NIH-PA Author Manuscript, PMC, (Mar. 1, 2011), also published in J. Memb. Sci. 349(1-2): 405 (Mar. 1, 2010).
Karan et al., "Ultrafast Viscous Permeation of Organic Solvents Through Diamond-Like Carbon Nanosheets," Science 335: 444-447 (Jan. 27, 2012).
Kim et al., "Fabrication and Characterization of Large Area, Semi-conducting Nanoperforated Graphene Materials," Nano Letters 10(4): 1125-1131 (Mar. 1, 2010).
Kim et al., "The structural and electrical evolution of graphene by oxygen plasma-induced disorder," Nanotechnology IOP 20(375703): 1-8 (Aug. 26, 2009).
Koski and Cui, "The New Skinny in Two-Dimensional Nanomaterials", ACS Nano 7(5): 3739-3743 (May 16, 2013).
Liu et al., "Atomically Thin Molybdenum Disulfide Nanopores with High Sensitivity for DNA Translocation," ACS Nano 8(3): 2504-2511 (Feb. 18, 2014).
Liu et al., "Graphene Oxidation: Thickness-Dependent Etching and Strong Chemical Doping," Nano Letters 8(7): 1965-1970 (Jun. 19, 2008).
Mishra et al., "Functionalized Graphene Sheets for Arsenic Removal and Desalination of Sea Water," Desalination 282: 39-45 (Nov. 1, 2011).
Morse, "Scalable Synthesis of Semiconducting Nanopatterned Graphene Materials," InterNano Resources for Nanomanufacturing (undated). Retrieved Jun. 2, 2016 from: http://www.internano.org/node/345.
Nair et al., "Unimpeded Permeation of Water Through Helium-Leak-tight Graphene-Based Membranes," Science 335: 442-444 (Jan. 27, 2012).
O'Hern et al. "Selective Molecular Transport through Intrinsic Defects in a Single Layer of CVD Graphene," ACS Nano, 6(11): 10130-10138 (Oct. 2, 2012).
O'Hern et al., "Selective Ionic Transport through Tunable Subnanometer Pores in Single-Layer Graphene Membranes," Nano Letters 14(3): 1234-1241 (Feb. 3, 2014).
Paul, "Creating New Types of Carbon-Based Membranes," Science 335: 413-414 (Jan. 27, 2012).
Schweicher et al., "Membranes to achieve immunoprotection of transplanted islets," NIH-PA Author Manuscript, PMC, (Nov. 13, 2014), also published in Frontiers in Bioscience (Landmark Ed) 19: 49-76 (Jan. 1, 2014).
Sint et al., "Selective Ion Passage through Functionalized Graphene Nanopores," JACS 130: 16448-16449 (Nov. 14, 2008).

(56) References Cited

OTHER PUBLICATIONS

Suk et al., "Water Transport Through Ultrathin Graphene," Journal of Physical Chemistry Letters 1(10): 1590-1594 (Apr. 30, 2010).
Tan et al., "Beta-cell regeneration and differentiation: how close are we to the 'holy grail'?" J. Mol. Encodrinol. 53(3): R119-R129 (Dec. 1, 2014).
Vlassiouk et al., "Versatile ultrathin nanoporous silicon nitride membranes," Proc. Natl. Acad. Sci. USA 106(50): 21039-21044 (Dec. 15, 2009).
Wadvalla, "Boosting agriculture through seawater," Nature Middle East (Jul. 2, 2012). Retrieved Jun. 1, 2016 from: natureasia.com/en/nmiddleeast/article/10.1038/nmiddleeast.2012.92?WT.mc_id=FBK NatureMEast].
Wikipedia, "Ion track." Jun. 1, 2016. Retrieved Jun. 1, 2016 from: en.wikipedia.org/wiki/ion_track.
Xu et al., "Graphene-like Two-Dimensional Materials", Chemical Reviews 113: 3766-3798 (Jan. 3, 2013).
Zan et al., "Graphene Reknits Its Holes," Nano Lett. 12(8): 3936-3940 (Jul. 5, 2012).
Zhao et al. "Two-Dimensional Material Membranes: An Emerging Platform for Controllable Mass Transport Applications," Small 10(22): 4521-4542 (Sep. 10, 2014).
U.S. Notice of Allowance in U.S. Appl. No. 14/610,770 dated Jan. 23, 2017.
U.S. Notice of Allowance in U.S. Appl. No. 14/856,198 dated Feb. 10, 2017.
U.S. Notice of Allowance in U.S. Appl. No. 14/856,198 dated Mar. 1, 2017.
U.S. Office Action in U.S. Appl. No. 14/609,325 dated Feb. 16, 2017.
U.S. Office Action in U.S. Appl. No. 14/193,007 dated Mar. 23, 2017.
U.S. Office Action in U.S. Appl. No. 14/656,580 dated Feb. 9, 2017.
U.S. Office Action in U.S. Appl. No. 14/843,944 dated Jan. 6, 2017.
U.S. Office Action in U.S. Appl. No. 15/099,464 dated Mar. 10, 2017.
Australian Office Action in Application No. 2013235234 dated Dec. 19, 2017 (5 pages).
Japanese Office Action in Application No. 2017-002652 dated Nov. 24, 2017 (with English translation) (7 pages).
Chu, L., et al., "Porous graphene sandwich/poly(vinylidene fluoride) composites with high dielectric properties," Composites Science and Technology, 86, (2013), pp. 70-75.
European Extended Search Report in Application No. 15743307.9 dated Nov. 15, 2017 (14 pages).
European Extended Search Report in Application No. 15755350.4 dated Oct. 30, 2017 (9 pages).
European Extended Search Report in Application No. 15762019.6 dated Nov. 20, 2017 (12 pages).
European Extended Search Report in Application No. 15762213.5 dated Oct. 10, 2017 (8 pages).
Gu et al., "One-step synthesis of porous graphene-based hydrogels containing oil droplets for drug delivery", Royal Society of Chemistry (RSC), vol. 4, No. 7, Jan. 1, 2014, pp. 3211-3218.
Japanese Office Action in Application No. 2015-549508 dated Nov. 7, 2017 (with English translation) (2 pages).
Kim et al., "Selective Gas Transport Through Few-Layered Graphene and Graphene Oxide Membranes", Science, vol. 342, Oct. 4, 2013, pp. 91-95 (6 total pages).
Singapore Search Report and Written Opinion in Application No. 11201609272T dated Oct. 5, 2017 (11 pages).
U.S. Notice of Allowance in U.S. Appl. No. 15/099,464 dated Nov. 16, 2017 (5 pages).
U.S. Notice of Allowance in U.S. Appl. No. 15/332,982 dated Nov. 1, 2017 (9 pages).
U.S. Office Action in U.S. Appl. No. 14/707,808 dated Nov. 6, 2017 (27 pages).
U.S. Office Action in U.S. Appl. No. 15/099,193 dated Dec. 28, 2017 (25 pages).

U.S. Office Action in U.S. Appl. No. 15/099,304 dated Nov. 24, 2017 (23 pages).
Wang, M., et al., "Interleaved Porous Laminate Composed of Reduced Graphene Oxide Sheets and Carbon Black Spacers by In-Situ Electrophoretic Deposition," The Royal Society of Chemistry (2014), pp. 1-3.
Wimalasiri, Y., et al., "Carbon nanotube/graphene composite for enhanced capacitive deionization performance," Carbon 59 (2013), pp. 464-471.
Office Action for Indian Appl. Ser. No. 1566/DELNP/2013 dated Feb. 2, 2018 (7 pages).
Office Action for Japanese Appl. Ser. No. 2016-521448 dated Mar. 16, 2018 (5 pages).
Skrzypek et al., "Pancreatic islet macroencapsulation using microwell porous membranes", Scientific Reports, 7: 9186 | DOI:10.1038/s41598-017-09647-7, Aug. 23, 2017 (12 pages).
U.S. Notice of Allowance for U.S. Appl. No. 15/099,464 dated Feb. 28, 2018 (5 pages).
U.S. Office Action for U.S. Appl. No. 15/099,276 dated Mar. 22, 2018 (13 pages).
U.S. Office Action for U.S. Appl. No. 15/453,441 dated Mar. 22, 2018 (7 pages).
CN Office Action in Chinese Application No. 201580006829.5 dated Aug. 1, 2017. (English translation) (8 pages).
EP Office Action for European Application No. 15743307.9 dated Aug. 8, 2017. (17 pages).
European Search Report dated Aug. 28, 2017 from related EP application 15743750.0. (7 pages).
International Search Report and Written Opinion dated Aug. 14, 2017 from related PCT application PCT/US2017/031537. (12 pages).
Jiang, L. et al., Design of advanced porous grapheme materials: from grapheme nanomesh to 3D architectures. Nanoscale, Oct. 16, 2013, vol. 6, pp. 1922-1945.
JP Office Action in Japanese Application No. 2015-503405 dated Jun. 28, 2017. (English translation) (6 pages).
JP Office Action in Japanese Application No. 2015-549508 dated Jun. 27, 2017. (English translation) (7 pages).
Li, R.H. "Materials for immunoisolated cell transplantation". Adv. Drug Deliv. Rev. 33, 87-109 (1998). (23 pages).
Schweitzer, Handbook of Separation Techniques for Chemical Engineers, 1979, McGraw-Hill Book Company, pp. 2-5 to 2-8.
Search Report and Written Opinion dated Aug. 14, 2017 for Singapore Application No. 11201606287V. (10 pages).
Search Report and Written Opinion dated Aug. 22, 2017 for Singapore Application No. 11201607584P. (7 pages).
Sears et al., "Recent Developments in Carbon Nanotube Membranes for Water Purification and Gas Separation" Materials, vol. 3 (Jan. 4, 2010), pp. 127-149.
U.S. Notice of Allowance in U.S. Appl. No. 14/193,007 dated Sep. 6, 2017. (9 pages).
U.S. Notice of Allowance in U.S. Appl. No. 14/656,580 dated Sep. 5, 2017. (8 pages).
U.S. Office Action for U.S. Appl. No. 14/609,325 dated Aug. 25, 2017. (7 pages).
U.S. Office Action for U.S. Appl. No. 15/099,193 dated Jul. 19, 2017. (13 pages).
U.S. Office Action for U.S. Appl. No. 15/289,944 dated Jul. 13, 2017. (18 pages).
U.S. Office Action for U.S. Appl. No. 15/332,982 dated Aug. 18, 2017. (9 pages).
Barreiro et al. "Understanding the catalyst-free transformation of amorphous carbon into graphene by current-induced annealing," Scientific Reports, 3 (Article 1115): 1-6 (Jan. 2013).
Botari et al., "Graphene healing mechanisms: A theoretical investigation," Carbon, 99: 302-309 (Apr. 2016) (published online Dec. 2015).
Chen et al., "Defect Scattering in Graphene," Physical Review Letters, 102: 236805-1-236805-4 (Jun. 2009).
Chen et al., "Self-healing of defected graphene," Applied Physics Letters, 102(10): 103107-1-103107-5 (Mar. 2013).
Cheng et al., "Ion Transport in Complex Layered Graphene-Based Membranes with Tuneable Interlayer Spacing," Science Advances, 2(2): e1501272 (9 pages) (Feb. 2016).

(56) References Cited

OTHER PUBLICATIONS

Crock et al., "Polymer Nanocomposites with Graphene-Based Hierarchical Fillers as Materials for Multifunctional Water Treatment Membranes," Water Research, 47(12): 3984-3996 (Aug. 2013) (published online Mar. 2013).
Han et al., "Ultrathin Graphene Nanofiltration Membrane for Water Purification," Advanced Functional Materials, 23(29): 3693-3700 (Aug. 2013).
International Search Report and Written Opinion in PCT/US2016/027583 dated Jan. 13, 2017.
Written Opinion in PCT/US2016/027590 dated Jan. 6, 2017.
International Search Report and Written Opinion in PCT/US2016/027594 dated Jan. 13, 2017.
International Search Report and Written Opinion in PCT/US2016/027628 dated Jan. 9, 2017.
International Search Report and Written Opinion in PCT/US2016/027631 dated Jan. 13, 2017.
International Search Report and Written Opinion in PCT/US2016/027632 dated Jan. 9, 2017.
Written Opinion in PCT/US2016/052010 dated Dec. 20, 2016.
International Search Report in PCT/US2016/027629 dated Dec. 8, 2016.
International Search Report in PCT/US2016/052007 dated Dec. 27, 2016.
Kjeldsen, T., "Yeast secretory expression of insulin precursors," Appl Microbiol Biotechnol, 54: 277-286 (May 2000).
Lin et al., "A Direct and Polymer-Free Method for Transferring Graphene Grown by Chemical Vapor Deposition to Any Substrate," ACSNANO, 8(2): 1784-1791 (Jan. 2014).
Liu et al. "Synthesis of high-quality monolayer and bilayer graphene on copper using chemical vapor deposition," Carbon, 49(13): 4122-4130 (Nov. 2011) (published online May 2011).
O'Hern et al., "Nanofiltration across defect-sealed nanoporous monolayer graphene," Nano Letters, 15(5): 3254-3260 (Apr. 2015).
U.S. Corrected Notice of Allowance in U.S. Appl. No. 13/480,569 dated May 26, 2015.
U.S. Notice of Allowance for U.S. Appl. No. 14/610,770 dated Apr. 25, 2016.
U.S. Notice of Allowance in U.S. Appl. No. 14/819,273 dated Dec. 14, 2016.
U.S. Notice of Allowance in U.S. Appl. No. 13/480,569 dated Feb. 27, 2015.
U.S. Office Action in U.S. Appl. No. 13/480,569 dated Jul. 30, 2014.
U.S. Office Action in U.S. Appl. No. 14/856,471 dated Dec. 1, 2016.
U.S. Restriction Requirement in U.S. Appl. No. 14/193,007 dated Jul. 17, 2015.
Wang et al., "Graphene Oxide Membranes with Tunable Permeability due to Embedded Carbon Dots," Chemical Communications, 50(86): 13089-13092 (Nov. 2014) (published online Sep. 2014).
Xu et al., "Graphene Oxide-TiO$_2$ Composite Filtration Membranes and their Potential Application for Water Purification," Carbon, 62: 465-471 (Oct. 2013) (published online Jun. 2013).
Zhao et al., "A glucose-responsive controlled release of insulin system based on enzyme multilayers-coated mesoporous silica particles," Chem. Commun., 47: 9459-9461 (Jun. 2011).
Allen et al., "Craters on silicon surfaces created by gas cluster ion impacts," Journal of Applied Physics, 92(7): 3671-3678 (Oct. 2002).
Atmeh et al., "Albumin Aggregates: Hydrodynamic Shape and Physico-Chemical Properties," Jordan Journal of Chemistry, 2(2): 169-182 (2007).
Chen et al., "Mechanically Strong, Electrically Conductive, and Biocompatible Graphene Paper," Adv. Mater., 20(18): 3557-3561 (Sep. 2008) (available online Jul. 2008).
CN Office Action in Chinese Application No. 201380013988.9 dated Aug. 18, 2016 (English translation not readily available).
Fuertes, "Carbon composite membranes from Matrimid® and Kapton® polyimides for gas separation," Microporous and Mesoporous Materials, 33: 115-125 (1991).

Galashev, "Computer study of the removal of Cu from the graphene surface using Ar clusters," Computational Materials Science, 98: 123-128 (Feb. 2015) (available online Nov. 2014).
International Search Report and Written Opinion in PCT/US2015/013599 dated Jul. 20, 2015.
International Search Report and Written Opinion in PCT/US2015/013805 dated Apr. 30, 2015.
International Search Report and Written Opinion in PCT/US2015/018114 dated Jun. 3, 2015.
International Search Report and Written Opinion in PCT/US2015/020246 dated Jun. 10, 2015.
International Search Report and Written Opinion in PCT/US2015/020296 dated Jun. 17, 2015.
International Search Report and Written Opinion in PCT/US2015/028948 dated Jul. 16, 2015.
International Search Report and Written Opinion in PCT/US2015/029932 dated Oct. 6, 2015.
Inui et al., "Molecular dynamics simulations of nanopore processing in a graphene sheet by using gas cluster ion beam," Appl. Phys. A, 98: 787-794 (Mar. 2010) (available online Dec. 2009).
Koh et al., "Sensitive NMR Sensors Detect Antibodies to Influenza," NIH PA Author Manuscript PMC (Apr. 2009), also published in Angew. Chem. Int'l Engl, 47(22): 4119-4121 (May 2008) (available online Apr. 2008).
Lehtinen et al., "Cutting and controlled modification of graphene with ion beams," Nanotechnology, 22: 175306 (8 pages) (Mar. 2011).
Matteucci et al., "Transport of gases and Vapors in Glass and Rubbery Polymers," in Materials Science of Membranes for Gas and Vapor Separation. (Yampolskii et al., eds. 2006) (available online Jun. 2006).
O'Hern et al., "Development of process to transfer large areas of LPCVD graphene from copper foil to a porous support substrate," 1-62 (M.S. Thesis, Massachusetts Institute of Technology, Thesis) (Sep. 2011).
Plant et al. "Size-dependent propagation of Au nanoclusters through few-layer graphene," Nanoscale, 6: 1258-1263 (2014) (available online Oct. 2013).
Popok. "Cluster Ion Implantation in Graphite and Diamond: Radiation Damage and Stopping of Cluster Constituents," Reviews on Advanced Materials Science, 38(1): 7-16 (2014).
Russo et al., "Atom-by-atom nucleation and growth of graphene nanopores," PNAS 109(16): 5953-5957 (Apr. 2012).
U.S. Notice of Allowance in U.S. Appl. No. 14/610,770 dated Aug. 12, 2016.
U.S. Office Action in U.S. Appl. No. 14/656,190 dated Aug. 29, 2016.
U.S. Office Action for U.S. Appl. No. 14/656,580 dated Jun. 2, 2016.
U.S. Office Action in U.S. Appl. No. 14/819,273 dated Jul. 6, 2016.
U.S. Office Action for U.S. Appl. No. 14/856,198 dated Jun. 3, 2016.
Yoon, "Simulations show how to turn graphene's defects into assets," ScienceDaily (Oct. 4, 2016), www.sciencedaily.com/releases/2016/10/161004120428.htm.
Zabihi et al., "Formation of nanopore in a suspended graphene sheet with argon cluster bombardment: A molecular dynamics simulation study," Nuclear Instruments and Methods in Physics Research B, 343: 48-51: (Jan. 2015) (available online Nov. 2014).
Zhang et al. Modern Thin-Film Technology 284-285 (Metallurgical Industry Press, 1st ed. 2009) (English translation not readily available).
Zhao et al. (2012), "Effect of SiO2 substrate on the irradiation-assisted manipulation of supported graphene: a molecular dynamics study," Nanotechnology 23(28): 285703 (Jul. 2012) (available online Jun. 2012).
Zhao et al. (May 2012), "Drilling Nanopores in Graphene with Clusters: A Molecular Dynamics Study," J. Phys. Chem. C, 116(21): 11776-11178 (2012) (available online May 2012).
Dong et al., "Growth of large-sized graphene thin-films by liquid precursor-based chemical vapor deposition under atmospheric pressure," Carbon 49(11): 3672-3678 (May 2011).

(56) References Cited

OTHER PUBLICATIONS

Hong et al., "Graphene multilayers as gates for multi-week sequential release of proteins from surfaces," NIH-PA Author Manuscript PMC (Jun. 1, 2014), also published in ACS Nano, Jan. 24, 2012; 6(1): 81-88 (first published online Dec. 29, 2011).
Hu et al., "Enabling graphene oxide nanosheets as water separation membranes," Environmental Science & Technology, 47(8): 3715-3723 (Mar. 14, 2013).
International Search Report and Written Opinion of the International Searching Authority dated Jul. 22, 2016, from related international patent application PCT/US2016/027607.
International Search Report and Written Opinion of the International Searching Authority dated Jul. 22, 2016, from related international patent application PCT/US2016/027616.
International Search Report and Written Opinion of the International Searching Authority dated Jul. 22, 2016, from related PCT application PCT/US2016/027596.
International Search Report and Written Opinion of the International Searching Authority dated Jul. 22, 2016, from related PCT application PCT/US2016/027603.
International Search Report and Written Opinion of the International Searching Authority dated Jul. 22, 2016, from related PCT application PCT/US2016/027610.
International Search Report and Written Opinion of the International Searching Authority dated Jul. 22, 2016, from related PCT application PCT/US2016/027612.
International Search Report and Written Opinion of the International Searching Authority dated Jun. 22, 2016, from related PCT application PCT/US2016/027637.
Kurapati et al., "Graphene oxide based multilayer capsules with unique permeability properties: facile encapsulation of multiple drugs," Chemical Communication 48: 6013-6015 (Apr. 25, 2012).
Li et al., "3D graphene oxide-polymer hydrogel: near-infrared light-triggered active scaffold for reversible cell capture and on-demand release," Advanced Materials 25: 6737-6743 (Oct. 7, 2013).
Marquardt et al., "Hybrid materials of platinum nanoparticles and thiol-functionalized graphene derivatives," Carbon 66: 285-294 (Jan. 2014; first published online Sep. 12, 2013).
Nam et al., "Monodispersed PtCo nanoparticles on hexadecyltrimethylammonium bromide treated graphene as an effective oxygen reduction reaction catalyst for proton exchange membrane fuel cells," Carbon 50: 3739-3747 (Aug. 2012; first published online Apr. 5, 2012).
Nandamuri et al., "Chemical vapor deposition of graphene films," Nanotechnology 21(14): 1-4 (Mar. 10, 2010).
Nayini et al., "Synthesis and characterization of functionalized carbon nanotubes with different wetting behaviors and their influence on the wetting properties of carbon nanotubes/polymethylmethacrylate coatings," Progress in Organic Coatings 77(6): 1007-1014 (Mar. 2014).
Sun et al., "Growth of graphene from solid carbon sources," Nature 468(7323): 549-552 (Nov. 25, 2010; including corrigendum in Nature 471(7336): 124 (Mar. 2011).
Tang et al., "Highly wrinkled cross-linked graphene oxide membranes for biological and charge-storage applications," Small 8(3): 423-431 (Feb. 6, 2012; first published online Dec. 13, 2011).
European Extended Search Report in Application No. 15837617.8 dated Mar. 22, 2018 (9 pages).
Singapore Written Opinion for Appl. Ser. No. 11201607584P dated Jun. 8, 2018 (7 pages).
U.S. Non-Final Office Action for U.S. Appl. No. 15/099,410 dated Jun. 13, 2018 (15 pages).
U.S. Notice of Allowance for U.S. Appl. No. 15/453,441 dated Jun. 12, 2018 (8 pages).
U.S. Office Action for U.S. Appl. No. 15/099,056 dated May 29, 2018 (33 pages).
Bose et al.,"Microfabricated immune-isolating devices for transplanting therapeutic cells in vivo", Koch Institute of Integrative Cancer Research, Massachusetts Institute of Technology, Undated (1 page).
Indian Office Action for Appl. Ser. No. 7731/DELNP/2014 dated Jul. 26, 2018 (6 pages).
Japanese Office Action for Appl. Ser. No. 2017-002652 dated Jul. 3, 2018 (8 pages).
Linnert, "Welding Metallurgy—Carbon and Alloy Steels", vol. I—Fundamentals (4th Edition), Chapter 2—The Structure of Metals, GML Publications, American Welding Society (AWS), Year: 1994, pp. 17-74. Retrieved from app.knovel.com/hotlink/pdf/id:kt0095RCL3/welding-metallurgy-carbon/structure-metals.
U.S. Final Office Action for U.S. Appl. No. 14/707,808 dated Jun. 27, 2018 (28 pages).
U.S. Final Office Action for U.S. Appl. No. 15/099,482 dated Aug. 27, 2018 (10 pages).
U.S. Non-Final Office Action for U.S. Appl. No. 15/099,239 dated Jul. 12, 2018 (31 pages).
U.S. Non-Final Office Action for U.S. Appl. No. 15/099,304 dated Aug. 27, 2018 (22 pages).
U.S. Notice of Allowance for U.S. Appl. No. 15/099,420 dated Aug. 8, 2018 (8 pages).
Vatanpour et al., "Fabrication and characterization of novel anti-fouling nanofiltration membrane prepared from oxidized multiwalled carbon nanotube/polyethersulfone nanocomposite", Journal of Membrane Science, vol. 375, Elsevier, Apr. 6, 2011, pp. 284-294.
Zhang et al., "Synergetic effects of oxidized carbon nanotubes and graphene oxide on fouling control and anti-fouling mechanism of polyvinylidene fluoride ultrafiltration membranes", Journal of Membrane Science, vol. 448, Elsevier, Aug. 7, 2013, pp. 81-92.
U.S. Final Office Action for U.S. Appl. No. 14/609,325 dated Sep. 12, 2018 (8 pages).
U.S. Non-Final Office Action for U.S. Appl. No. 14/656,657 dated Oct. 10, 2018 (6 pages).
U.S. Non-Final Office Action for U.S. Appl. No. 14/707,808 dated Nov. 15, 2018 (34 pages).
U.S. Non-Final Office Action for U.S. Appl. No. 15/099,099 dated Sep. 27, 2018 (13 pages).
U.S. Non-Final Office Action for U.S. Appl. No. 15/099,269 dated Oct. 5, 2018 (11 pages).
U.S. Non-Final Office Action for U.S. Appl. No. 15/099,276 dated Nov. 1, 2018 (13 pages).
U.S. Notice of Allowance for U.S. Appl. No. 15/099,056 dated Nov. 16, 2018 (8 pages).
U.S. Appl. No. 15/099,420, filed Apr. 14, 2016.
U.S. Appl. No. 15/099,447, filed Apr. 14, 2016.
U.S. Appl. No. 15/099,269, filed Apr. 14, 2016.
U.S. Appl. No. 15/099,239, filed Apr. 14, 2016.
U.S. Appl. No. 15/099,464, filed Apr. 14, 2016.
U.S. Appl. No. 15/099,276, filed Apr. 14, 2016.
U.S. Appl. No. 15/099,482, filed Apr. 14, 2016.
U.S. Appl. No. 15/099,056, filed Apr. 14, 2016.
U.S. Appl. No. 15/099,099, filed Apr. 14, 2016.
U.S. Appl. No. 14/656,190, filed Mar. 12, 2015.
U.S. Appl. No. 15/099,304, filed Apr. 14, 2016.
U.S. Appl. No. 15/099,588, filed Apr. 14, 2016.
U.S. Appl. No. 14/610,770, filed Jan. 30, 2015.
U.S. Appl. No. 14/656,657, filed Mar. 12, 2015.
U.S. Appl. No. 14/609,325, filed Jan. 29, 2015.
U.S. Appl. No. 14/656,580, filed Mar. 12, 2015.
U.S. Appl. No. 13/480,569, filed May 25, 2012.
U.S. Appl. No. 14/707,808, filed May 8, 2015.
U.S. Appl. No. 14/856,109, filed Sep. 16, 2015.
U.S. Appl. No. 14/819,273, filed Aug. 5, 2015.
U.S. Appl. No. 14/754,531, filed Jun. 29, 2015.
PCT/US2015/018114, Feb. 27, 2015.
U.S. Appl. No. 14/843,944, filed Sep. 2, 2016.
U.S. Appl. No. 15/099,193, filed Apr. 14, 2016.
PCT/US2015/028948, May 1, 2015.
U.S. Appl. No. 14/858,741, filed Sep. 18, 2015.
U.S. Appl. No. 14/193,007, filed Feb. 28, 2014.
U.S. Appl. No. 14/856,471, filed Sep. 16, 2015.
U.S. Appl. No. 15/099,295, filed Apr. 14, 2016.
U.S. Appl. No. 15/099,410, filed Apr. 14, 2016.
U.S. Appl. No. 15/099,289, filed Apr. 14, 2016.
U.S. Appl. No. 15/308,351, filed Nov. 1, 2016.

(56) References Cited

OTHER PUBLICATIONS

U.S. Appl. No. 14/843,944, filed Sep. 2, 2015.
U.S. Appl. No. 15/336,545, filed Oct. 27, 2016.
U.S. Appl. No. 15/289,944, filed Oct. 10, 2016.
U.S. Pat. No. 9,193,587, Nov. 24, 2015, U.S. Appl. No. 13/548,539, filed Jul. 13, 2012.
U.S. Appl. No. 13/422,753, filed Mar. 16, 2012.
U.S. Pat. No. 8,361,321, Jan. 29, 2013, U.S. Appl. No. 12/868,150, filed Aug. 25, 2010.
U.S. Pat. No. 9,475,709, Oct. 25, 2016, U.S. Appl. No. 13/719,579, filed Dec. 19, 2012.
U.S. Pat. No. 9,028,663, May 12, 2015, U.S. Appl. No. 13/804,085, filed Mar. 14, 2013.
U.S. Appl. No. 14/686,452, filed Apr. 14, 2015.
U.S. Pat. No. 9,463,421, Oct. 11, 2016, U.S. Appl. No. 13/803,958, filed Mar. 14, 2013.
U.S. Pat. No. 9,095,823, Aug. 4, 2015, U.S. Appl. No. 13/802,896, filed Mar. 14, 2013.
U.S. Pat. No. 9,592,475, Mar. 14, 2017, U.S. Appl. No. 14/203,655, filed Mar. 11, 2014.
U.S. Pat. No. 9,480,952, Nov. 1, 2016, U.S. Appl. No. 14/200,195, filed Mar. 7, 2014.
U.S. Pat. No. 9,567,224, Feb. 14, 2017, U.S. Appl. No. 13/795,276, filed Mar. 12, 2013.
U.S. Appl. No. 14/031,300, filed Sep. 19, 2013.
U.S. Pat. No. 9,505,192, Nov. 29, 2016, U.S. Appl. No. 14/200,530, filed Mar. 7, 2014.
U.S. Pat. No. 9,572,918, Feb. 21, 2017, U.S. Appl. No. 13/923,503, filed Jun. 21, 2013.
U.S. Appl. No. 13/779,963, filed Feb. 28, 2013.
U.S. Pat. No. 9,610,546, Apr. 4, 2017, U.S. Appl. No. 14/856,198, filed Sep. 16, 2015.
U.S. Appl. No. 14/656,335, filed Mar. 12, 2015.
U.S. Appl. No. 14/656,617, filed Mar. 12, 2015.
U.S. Pat. No. 9,242,865, Jan. 26, 2016, U.S. Appl. No. 14/192,796, filed Feb. 27, 2014.
U.S. Appl. No. 15/589,135, filed May 8, 2017.
U.S. Appl. No. 15/332,982, filed Oct. 24, 2016.
U.S. Appl. No. 15/410,457, filed Jan. 19, 2017.
U.S. Appl. No. 15/453,441, filed Mar. 8, 2017.
U.S. Appl. No. 14/971,922, filed Dec. 16, 2015.
U.S. Pat. No. 9,169,575, Oct. 27, 2015, U.S. Appl. No. 14/195,802, filed Mar. 3, 2014.
US Final Office Action for U.S. Appl. No. 14/686,452 dated Dec. 13, 2018 (6 pages).
US Final Office Action for U.S. Appl. No. 15/099,099 dated Jan. 2, 2019 (13 pages).
US Non-Final Office Action for U.S. Appl. No. 14/609,325 dated Jan. 14, 2019 (7 pages).
US Notice of Allowance for U.S. Appl. No. 15/099,410 dated Jan. 3, 2019 (9 pages).

\* cited by examiner

MEMBRANES WITH TUNABLE SELECTIVITY

BACKGROUND

Membranes are used in a variety of separation-based applications, including in desalination and water softening, in bioreactors for wastewater treatment, in biomedical and pharmaceutical materials separation, and in other chemical engineering applications. Most membranes are fabricated with polymers (e.g., cellulose, polyamides, polymethyl, methacrylate, etc.), though polymeric membrane utility is limited by poor chemical and thermal stability of the membranes. Further limiting membrane utility is the static selectivity of membranes produced with current materials and methods. That is, membranes that allow permeability of a compound based on one set of characteristics (e.g., based on size, charge, hydrophobicity, etc.) cannot easily be altered to select for compounds with a different set of characteristics. Thus, selecting for multiple compounds with differential respective characteristics typically requires the use of multiple membranes, which increases separation costs and decreases utilization efficiency.

SUMMARY

Some embodiments comprise membranes comprising (a) a first layer comprising a porous graphene-based material, (b) a second layer comprising a porous graphene-based material, (c) channel positioned between the first layer and the second layer, wherein the channel has a tunable channel diameter, and (d) at least one spacer substance positioned in the channel, wherein the spacer substance is responsive to an environmental stimulus.

In some embodiments, the spacer substance expands and/or contracts in response to the environmental stimulus. In some embodiments, the spacer substance reversibly expands and/or reversibly contracts in response to the environmental stimulus. In some embodiments, the spacer substances has an effective diameter that increases or decreases by from about 0.3 to about 50 nm in response to the environmental stimulus. In some embodiments, the spacer substance density such that the spacer substances cover up to about 50% of the surface area of the center of the channel. In some embodiments, the spacer substance is covalently bonded to at least one graphene-based material layer.

In some embodiments, the spacer substance is selected from the group consisting of a polymer, a fiber, a hydrogel, a molecule, a nanostructure, a nanoparticle, a self-assembled monolayer, a magnetic particle, an allotrope, and combinations thereof. In some embodiments, the spacer substance is selected from the group consisting of a hygroscopic polymer, a thin polymer, an amorphous polymer, electrospun fibers, oxide nanoparticles, octadecyltrichlorosilane nanoparticles, carbon nanotubes, fullerene, collagen, keratin, aromatic amino acids, polyethylene glycol, lithium niobate particles, nanocrystals of 4-dimethylamino-N-methyl-4-stilbazolium tosylate, crystalline polytetrafluoroethylene, and combinations thereof.

In some embodiments, the channel diameter increases and/or decreases in response to the environmental stimulus. In some embodiments, the channel diameter is tuned via expansion and/or contraction of the spacer substance. In some embodiments, the channel has a maximum diameter that increases and/or decreases in response to the environmental stimulus. In some embodiments, the channel has a diameter of from about 20 nm to about 50 nm. In some embodiments, the channel diameter increases and/or decreases by from about 0.5 nm to about 50 nm in response to the environmental stimulus. In some embodiments, the channel is in a closed position before and/or after exposure to the environmental stimulus.

In some embodiments, the environmental stimulus is selected from the group consisting of variations in temperature, pressure, pH, ionic concentration, solute concentration, tonicity, light, voltage, electric fields, magnetic fields, pi-bonding availability, and combinations thereof.

In some embodiments, membrane permeability is responsive to the environmental stimulus. In some embodiments, the membrane (e.g., graphene based layers+spacers substances) is from about 5 nm to about 20 nm thick.

In some embodiments, the first layer and second layer contain pores with a diameter of from about 0.1 nm to about 200 nm. In some embodiments, the average pore diameter in the first layer is different from the average pore diameter in the second layer. In some embodiments, the spacer substance has an effective diameter that is larger than the average pore diameter in the first and second layers.

In some embodiments, at least one functional group is attached to at least a portion of the pores in the first layer and/or the second layer. In some embodiments, the functional group is selected from the group consisting of a negatively-charged group, a positively-charged group, an adsorptive substance, a catalytic substance, a specific binding site, and combinations thereof.

In some embodiments, the porous graphene-based material in the first layer is structurally different from the porous graphene-based material in the second layer. In some embodiments, the porous graphene-based material in the first layer comprises a different number of graphene sheets than the porous graphene-based material in the second layer.

In some embodiments, the membrane comprises more than two layers comprising a porous graphene-based material. In some embodiments, the membrane comprises more than one channel.

In some embodiments, the graphene-based material is graphene.

Some embodiments comprise methods of altering membrane permeability by exposing a membrane to an environmental stimulus to thereby alter membrane permeability. In some embodiments, the membrane comprises a first layer with a porous graphene-based material, a second layer with a porous graphene-based material, and a channel between the first layer and the second layer, and the channel has a diameter that is altered upon exposing the membrane to the environmental stimulus. In some embodiments, the environmental stimulus is selected from the group consisting of variations in temperature, pressure, pH, ionic concentration, solute concentration, tonicity, light, voltage, electric fields, magnetic fields, pi-bonding availability, and combinations thereof. In some embodiments, the membrane permeability is altered by a change in the maximum diameter of a channel between the first layer and the second layer. In some embodiments, the membrane comprises at least one spacer substance positioned between the first layer and the second layer, wherein the spacer is responsive to the environmental stimulus. In some embodiments, the spacer substance expands and/or contracts in response to the environmental stimulus.

Some embodiments comprise methods of water filtration, water desalination, water purification, immune-isolation, timed drug release, hemodialysis, or hemofiltration. In some embodiments, the methods comprise exposing a membrane to an environmental stimulus, wherein the membrane comprises a first layer with a porous graphene-based material, a second layer with a porous graphene-based material, and a channel between the first layer and the second layer, and wherein the channel has a diameter that is altered upon exposing the membrane to the environmental stimulus. In some embodiments, the environmental stimulus is selected from the group consisting of variations in temperature, pressure, pH, ionic concentration, solute concentration, tonicity, light, voltage, electric fields, magnetic fields, pi-bonding availability, and combinations thereof. In some embodiments, the membrane comprises at least one spacer substance positioned between the first layer and the second layer, wherein the spacer is responsive to the environmental stimulus.

Some embodiments comprise methods of making a membrane that comprises a first layer with a porous graphene-based material, a second layer with a porous graphene-based material, and a spacer substance that is responsive to an environmental stimulus. In some embodiments, the methods comprise combining a spacer substance with a graphene-based material layer in solution, and then inducing bonding between the spacer substance and the graphene-based material layer. In some embodiments, the bonding is induced by ion-beam, electron beam, heating, chemical reactions, or combinations thereof. Some embodiments further comprise adding a second graphene-based material layer to the solution.

Some embodiments comprise membranes comprising a first layer comprising a porous graphene-based material; (b) a second layer comprising a porous graphene-based material; (c) a channel positioned between the first layer and the second layer, wherein the channel has a tunable channel diameter; and (d) a means for increasing and/or decreasing the diameter of the channel in response to an environmental stimulus. In some embodiments, the means for increasing and/or decreasing the diameter of the channel comprises a spacer substance positioned between the first layer and the second layer, wherein the spacer substance is responsive to the environmental stimulus. In some embodiments, the environmental stimulus is selected from the group consisting of variations in temperature, pressure, pH, ionic concentration, solute concentration, tonicity, magnetic fields, light, voltage, electric fields, pi-bonding availability, and combinations thereof.

BRIEF DESCRIPTION OF THE DRAWINGS

FIG. 5A shows contamination-based substances formed into a single line. FIG. 5B shows contamination-based substances patterned into a star. FIG. 5C and FIG. 5D show contamination-based spacer substances formed into a dot array (FIG. 5D provides a photograph with increased magnification as compared to FIG. 5C).

DETAILED DESCRIPTION

Figure 1:
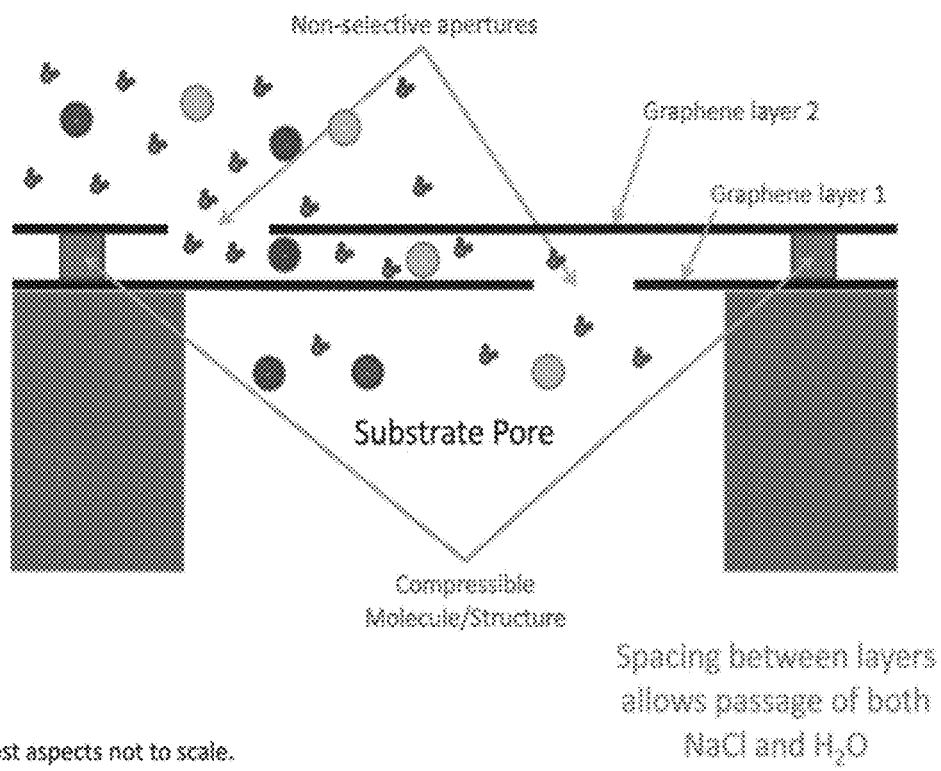
FIG. 1 illustrates some embodiments having a membrane with two porous graphene-based material layers, where the membrane allows passage of both water and salt ions.

Some embodiments include membranes, and methods of making membranes, with tunable selectivity, e.g., where the membrane can adapt to environmental conditions. In some embodiments, the membrane can be tuned as a result of being adjusted to alter selectivity. Some other embodiments include methods of altering membrane permeability and methods of using membranes with tunable selectivity.

Tunable Membranes

Membranes of some embodiments are formed with multiple layers of porous graphene-based material, where the layers are positioned or stacked such that a space between the layers can function as a channel or conduit. In some embodiments, the membrane comprises at least two layers of porous graphene-based material, such as from about 2 to about 10 layers, or from about 2 to about 5 layers of porous graphene-based material. In some embodiments, the membrane comprises 2, 3, 4, 5, 6, 7, 8, 9, or 10 layers of porous graphene-based material. The number of channels in the membrane depends in part on the number of graphene-based material layers in the membrane. Thus, two graphene-based material layers can form one channel; three graphene-based material layers can form two channels. In some embodiments, the walls of the channel comprise the graphene-based material layers.

In some embodiments, a graphene-based material layer comprises a single sheet of graphene-based material. In some other embodiments, a graphene-based material layer comprises multiple sheets of graphene-based material, such as from about 2 to about 5 sheets of graphene-based material. When a layer comprises multiple sheets of graphene-based material, the sheets of can be combined in the layer via, e.g., covalent bonding and/or van der Waals forces. Graphene-based materials are discussed in greater detail later in this application.

The porous graphene-based material layers in the membrane can be structurally similar, structurally identical, or structurally different from other porous graphene-based material layers in the membrane. For instance, in some embodiments, all graphene-based material layers have the same number of graphene sheets. In some embodiments, the number of graphene sheets in a layer is different from the number of graphene sheets in a different layer. The porous graphene-based material layers in the membrane can be chemically similar, chemically identical, or chemically different from other porous graphene-based material layers in the membrane. In some embodiments, graphene-based material layers can be functionalized with similar, identical, or different functional groups from other graphene-based material layers.

The thickness of the membrane depends in part on the number of layers present in the membrane and/or on the number of graphene-based material sheets in the membrane. In some embodiments, the membrane is at least 5 nm thick, such as from about 5 nm to about 250 nm thick, from about 5 to about 20 nm thick, or from about 20 to about 50 nm thick.

Membranes of some of the embodiments provide a means for increasing and/or decreasing the diameter of the channel. For example, at least one spacer substance can be positioned in the channel between the graphene-based material layers. In some embodiments, the spacer substance is responsive to an environmental stimulus. Exemplary environmental stimuli include changes in temperature, pressure, pH, ionic concentration, solute concentration, tonicity, light, voltage, electric fields, magnetic fields, pi-bonding availability, and combinations thereof. In some embodiments, the spacer substance is responsive to a single environmental stimulus. In some embodiments, the spacer substance is responsive to two or more environmental stimuli.

Figure 2:
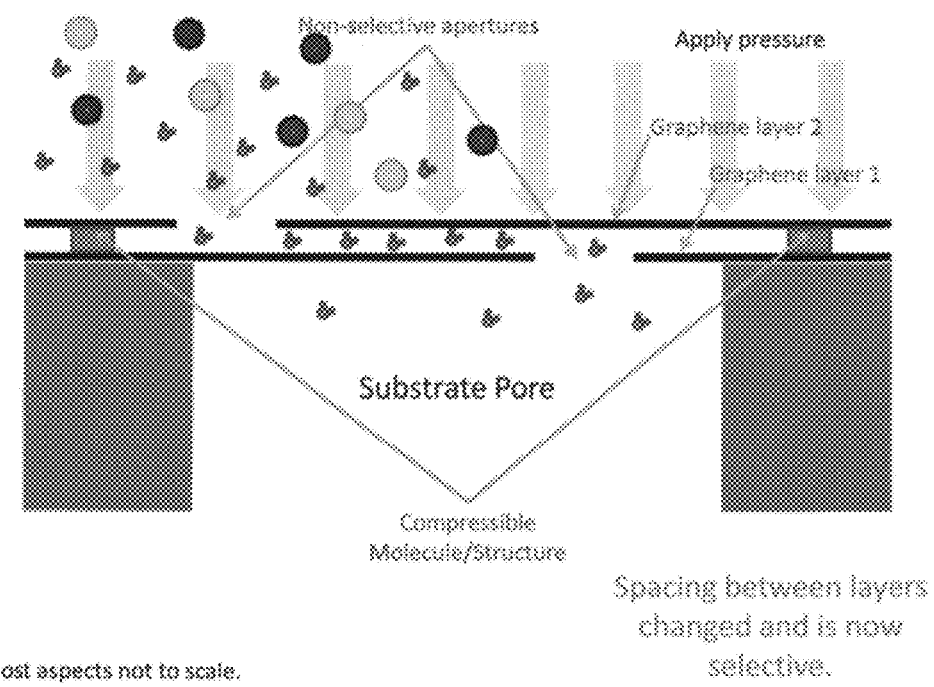
FIG. 2 illustrates some embodiments having a membrane with two porous graphene-based material layers, where applied pressure on the membrane excludes passage of salt ions.
Figure 3:
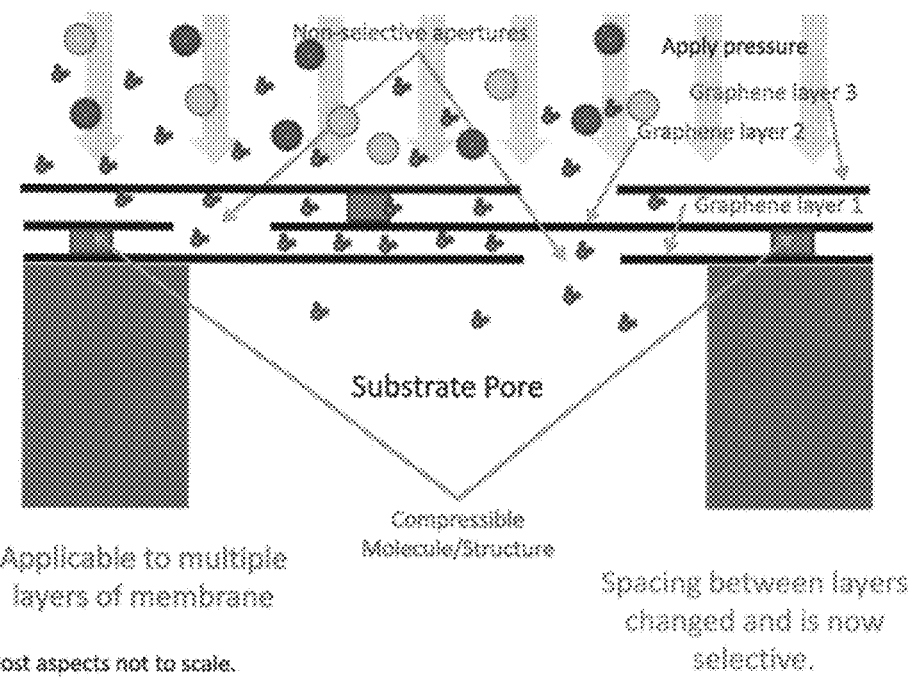
FIG. 3 illustrates some embodiments having a membrane with three porous graphene-based material layers, where applied pressure on the membrane excludes passage of salt ions.

The properties of the responsive spacer substances can be altered upon exposure to an environmental stimulus. For instance, in some embodiments the spacer substance can expand and/or contract in response to an environmental stimulus. By way of example, the effective diameter of the spacer substance can be reduced in response to an increase in applied pressure. This is demonstrated in FIGS. 1-3, which shows a membrane channel with altered selectivity following application of pressure (initially, both water and ions, electrolytes, and/or salts in solution can traverse the membrane—FIG. 1; increased pressure compresses the spacer substance and prevents the salt from traversing the membrane—FIG. 2; FIG. 3 demonstrates that pressure can be used to compress a spacer substance in a membrane with three graphene layers). The term "effective diameter" as it relates to spacer substances refers to the distance between two points on the spacer substance, where the points interact with different graphene-based material layers that form a channel of the membrane (i.e., the height of the spacer substance in the membrane). In this way, the effective diameter of the spacer substance influences the diameter of the channel. An initial effective diameter of the spacer substances can be determined prior to incorporating the spacer substance into the membrane, for instance via transmission electron microscopy (TEM) tomography. For some spacer substances, such as nanoparticles and other particle-based spacer substances, the effective diameter can be determined via scanning electron microscopy (SEM).

In some embodiments, the effective diameter of the spacer substance can be increased upon removal of or reduction in applied pressure. In some embodiments, the effective diameter of the spacer substance increases upon hydration and/or decreases upon dehydration. In some embodiments, the spacer substance is capable of undergoing a physical and/or chemical transformation in the membrane based on an interaction with an activating substance, such as an affinity-based interaction or a chemical reduction. In some embodiments, the environmental stimulus induces a conformational change in the spacer substance that alters the effective diameter of the spacer substance. For instance, conformational changes between trans and cis forms of a spacer substance can alter the effective diameter of the spacer substance (by way of example, a spacer substance could be a polymer with an embedded diazo dye, where exposure to the appropriately colored light alters the volume of the dye based on cis-/trans-conformational changes). In some embodiments, the spacer substance undergoes a physical and/or chemical transformation that is pH-modulated or optically modulated. In some embodiments, the environmental stimulus degrades the spacer substance to alter the effective diameter of the spacer substance.

Figure 4:
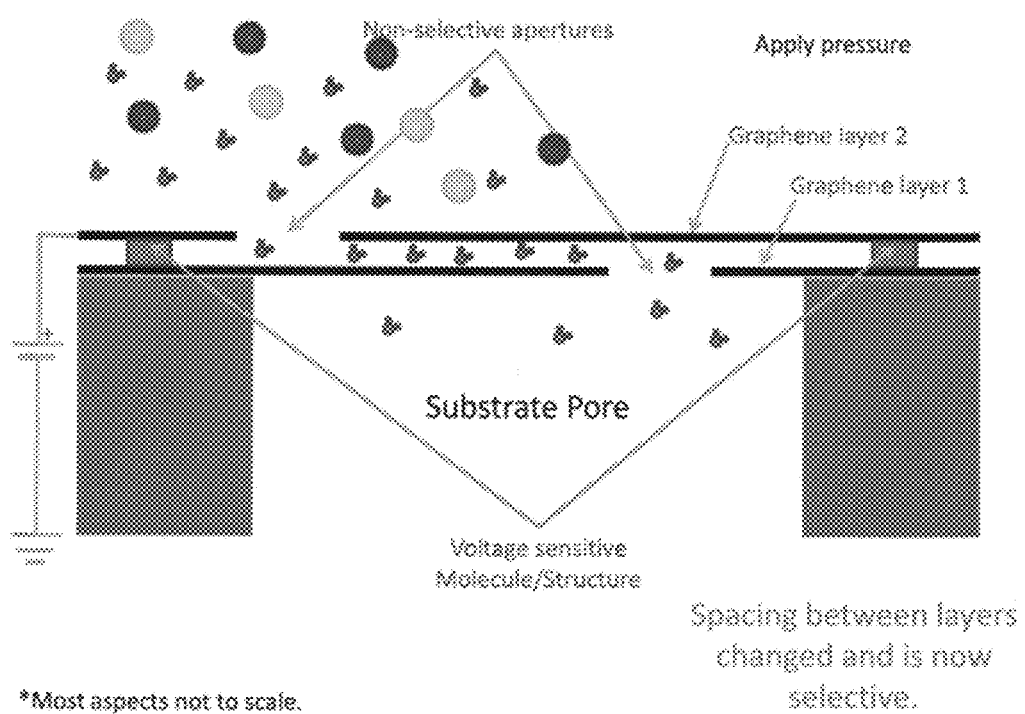
FIG. 4 illustrates some embodiments having a membrane with two porous graphene-based material layers, where applied voltage across the membrane excludes passage of salt ions.
Figure 5A:
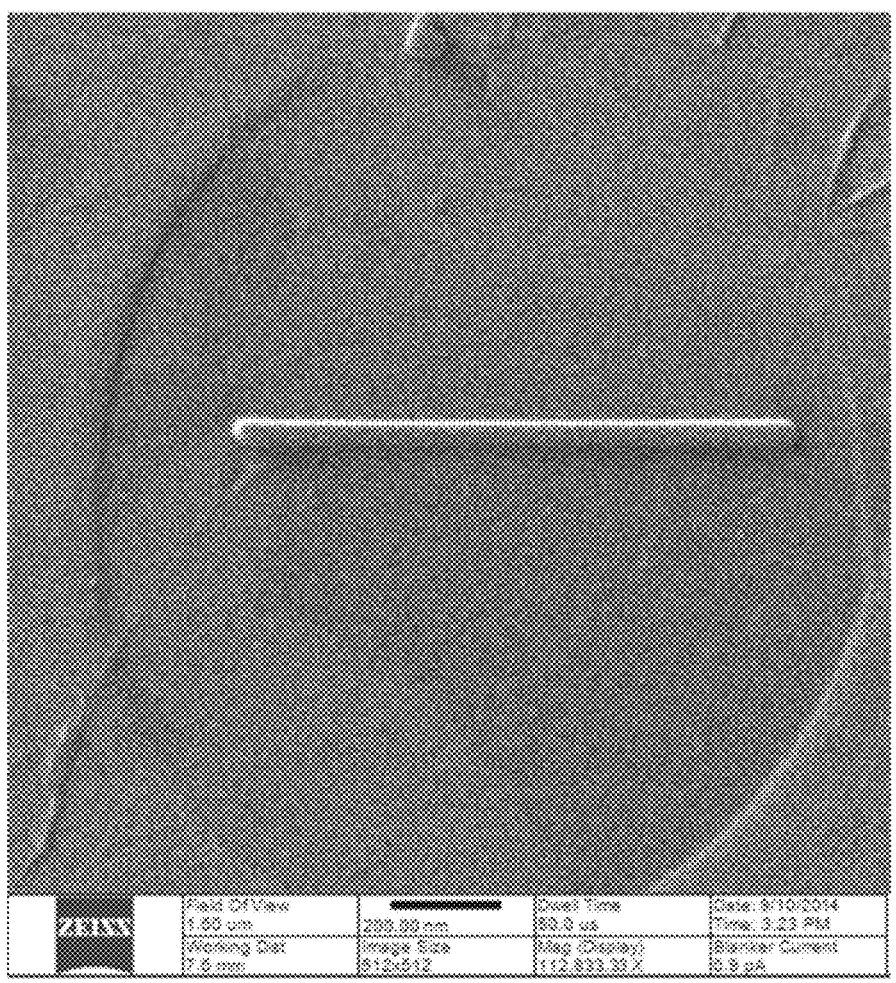
FIG. 5A-D show photographs of some embodiments of contamination-based spacer substances formed into various shapes or patterns.
Figure 5B:
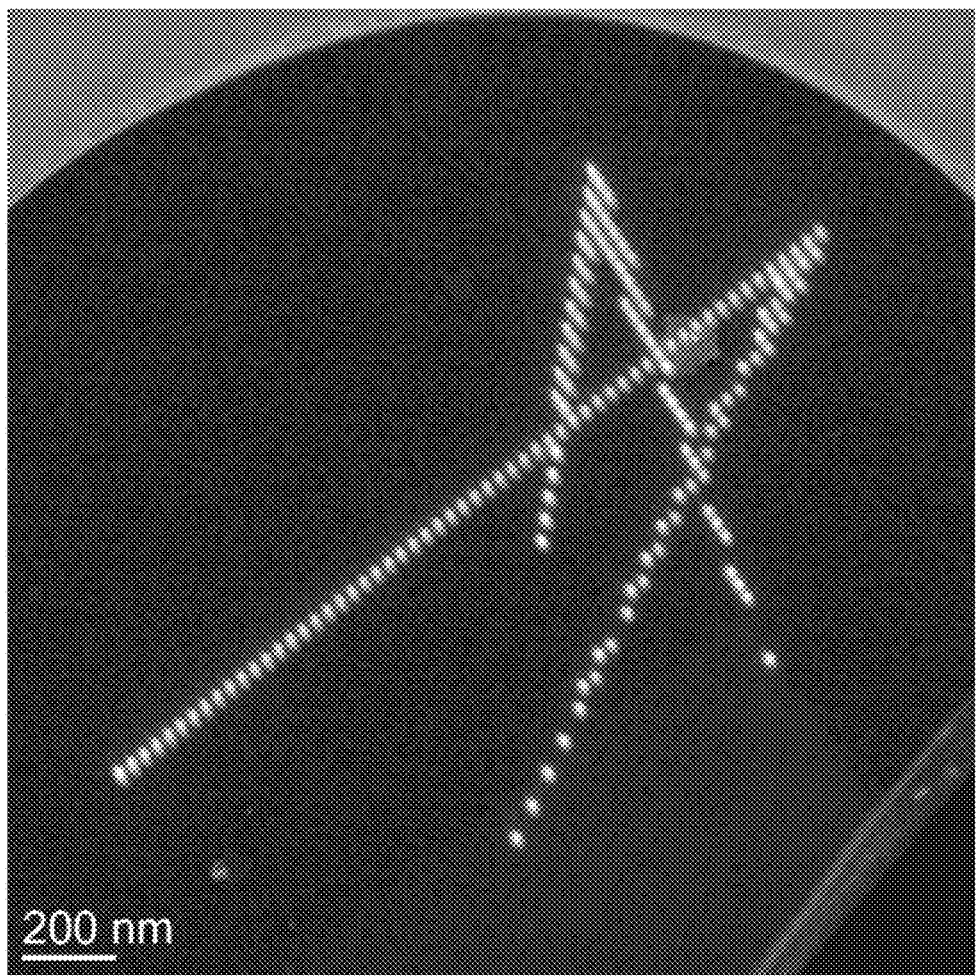
Figure 5C:
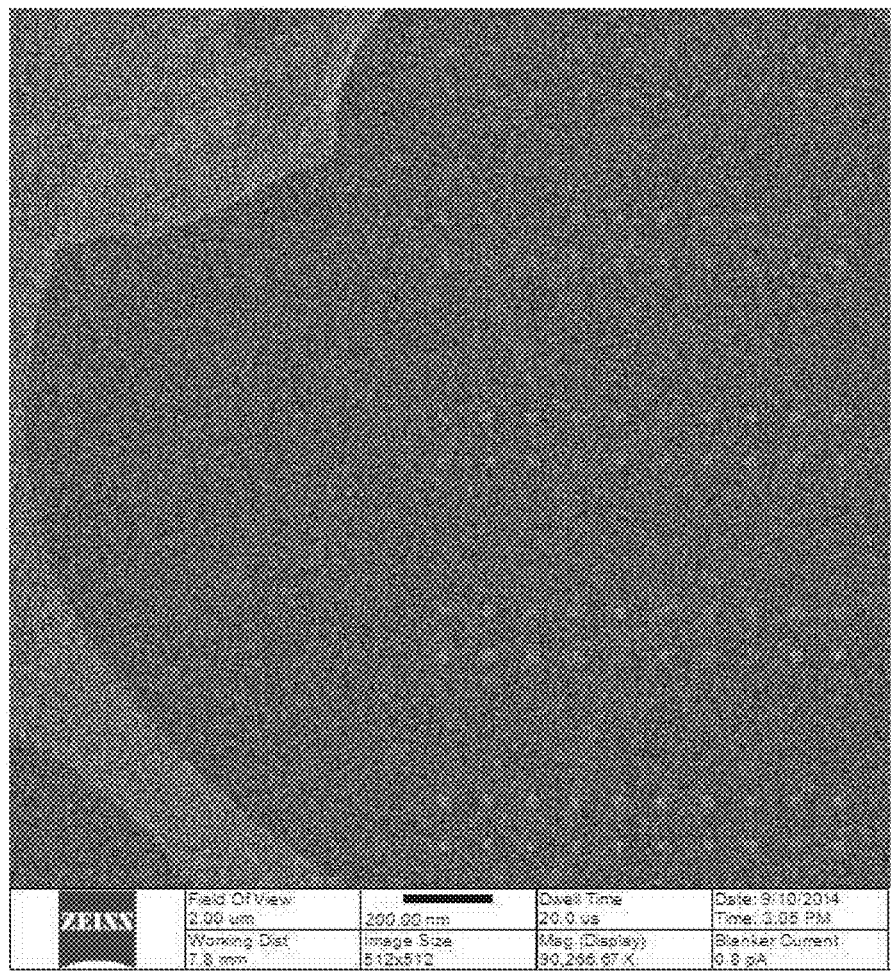
Figure 5D:
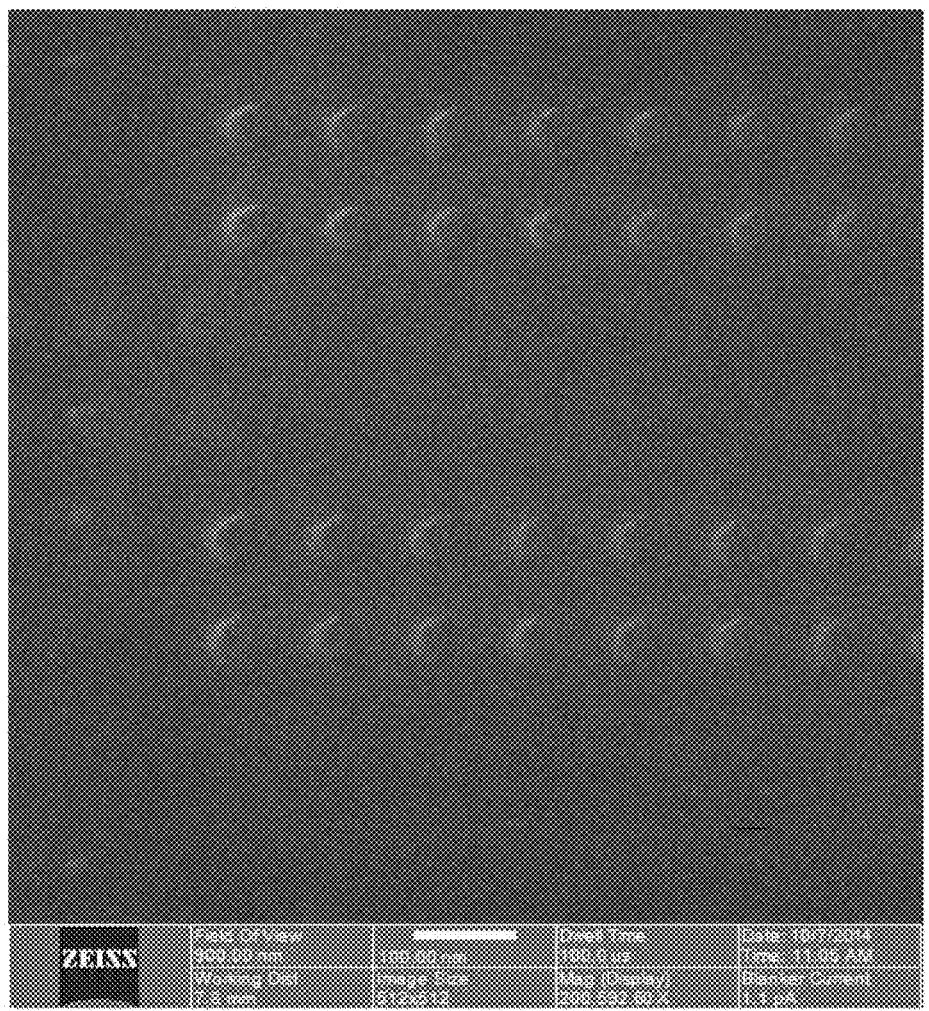

In some embodiments, the effective diameter of the spacer substance can be altered by applying a voltage to the membrane or via electrowetting. See, for instance, FIG. 4, showing that the spacing between layers can be altered via voltage-sensitive spacer substances. In some embodiments, a voltage or field source is applied across the membrane. In some embodiments, the voltage assists in moving the permeant across the membrane. In some embodiments, the voltage is applied across the membrane using a power source, such as a battery, a wall outlet, or an applied RF field (or other beam). In some embodiments, a voltage of about 1 mV to about 900 mV is applied across the membrane. In some embodiments, the voltage is applied to a graphene-based material layer in-plane. In some embodiments, the graphene can be biased, for instance with the use of an insulating material. In some embodiments, the voltage applied across the membrane is low enough that the graphene does not delaminate and/or low enough that the voltage does not induce electrolysis.

The responsive change in spacer substance properties can be reversible or irreversible. In some embodiments, the spacer substances reversibly expands and/or reversibly contracts in response to the environmental stimulus. Therefore, in some embodiments, the size of the spacer substance can be repeatedly increased and then decreased in succession. In some embodiments, the size of spacer substance can be increased or decreased, but not both. In some embodiments, the size of the spacer substance can be increased or decreased irreversibly.

Spacer substances can include polymers, fibers, hydrogels, molecules, nanostructures, nanoparticles, self-assembled monolayers, and allotropes that are responsive to an environmental stimulus. In some embodiments, the spacer substance is a smart polymer, such as a hygroscopic polymer; a thin polymer that expands when hydrated; or an amorphous polymer, such as a porous amorphous polymer. In some embodiments, the spacer substance comprises electrospun fibers that can be swelled upon exposure to a solvent. In some embodiments the spacer substance comprises materials with a high thermal expansion coefficient, which expand or contract in response to a temperature stimulus. In some embodiments, the spacer substance is deliquescent. In some embodiments, the spacers are substantially inert. In some embodiments, the spacers are not inert (i.e., they can be reactive).

Exemplary spacer substance includes particle substances such as metal nanoparticles (e.g., silver nanoparticles), oxide nanoparticles, octadecyltrichlorosilane nanoparticles, carbon nanotubes, and fullerenes. In some embodiments, the spacer substance includes nanorods, nano-dots (including decorated nano-dots), nanowires, nanostrands, and lacey carbon materials.

Exemplary spacer substances also include structural proteins, collagen, keratin, aromatic amino acids, and polyethylene glycol. Such spacer substances can be responsive to changes in tonicity of the environment surrounding the spacer substance, pi-bonding availability, and/or other environmental stimuli.

In some embodiments, the spacer substance is a piezoelectric, electrostrictive, or ferroelectric magnetic particle. In some embodiments, the magnetic particle comprises a molecular crystal with a dipole associated with the unit cell. In some embodiments, the magnetic particles can be oriented based on an external magnetic field. Exemplary magnetic particles include lithium niobate, nanocrystals of 4-dimethylamino-N-methyl-4-stilbazolium tosylate (DAST)), crystalline polytetrafluoroethylene (PTFE), electrospun PTFE, and combinations thereof.

In some embodiments, the spacer substance heats up faster or slower than its surroundings. Without being bound by theory, it is believed that such embodiments will allow the rate of passage of permeants, or a subset of permeants, across the membrane to be increased and/or decreased.

In some embodiments, spacer substances respond to electrochemical stimuli. For instance, a spacer substance can be an electrochemical material (e.g., lithium ferrophosphate), where a change in oxidation state of the spacer substance (e.g., from $2^-$ to $3^-$) alters permeability of the membrane. In some embodiments, changing the oxidation state of the spacer substances alters the interaction between the spacer substance and potential permeants. In some embodiments, the change in oxidation state results from a redox-type reaction. In some embodiments, the change in oxidation state results from a voltage applied to the membrane.

In some embodiments, the spacer substance comprises contamination structures formed by utilizing a focused ion beam, e.g., to modify heavy levels of contamination on graphene-based material into more rigid structures. For instance, in some embodiments, mobilization and migration of contamination on the surface of the graphene-based material occurs—coupled in some embodiments with some slight beam induced deposition—followed by modification and induced bonding where the beam is applied. In some embodiments, combining contamination structures allows the geometry, thickness, rigidity, and composition of the spacer substance to be tuned to respond to an environmental stimulus (e.g., pressure). Exemplary contamination-based spacer substances are shown in FIGS. 5A-D.

In some embodiments, spacer substances have an affinity for graphene. In some embodiments, spacer substances have a higher affinity for graphene than for substances or solutions that can permeate the membrane.

In some embodiments, the spacer substance is chemically modified to have a functional group or a desired physiochemical property. For example, in some embodiments the spacer substance is modified to be hydrophobic. In some embodiments, the spacer substance is modified to be hydrophilic. In some embodiments, the spacer substance is modified by addition of hydroxyl groups. In some embodiments, the spacer substance is attached to antibody receptors. In some embodiments, the spacer substance is attached to proteins, enzymes, and/or catalysts. For example, in some embodiments a metallic, organometallic, and/or zeolite-based functional group can act as a catalyst for precursors that enter the membrane. In some embodiments, spacer substances are functionalized to preferentially orient a permeant (e.g., water or a solvent). In some embodiments, a permeant that is in the preferential orientation can traverses the membrane in that preferential orientation, whereas a permeant that is not the preferential orientation does not.

In some embodiments, membranes include a plurality of a single type of spacer substance (e.g., a plurality of nanoparticles). In some embodiments, membranes include a multiple types of spacer substances (e.g., nanoparticles and polymers). In some embodiments, the spacer substance is a porous layer, such as a porous amorphous polymer layer. In some embodiments, the spacer substance is a self-assembled co-polymer that leaves channels between graphene-based material layers (e.g., the channels can be a sub-nm in diameter to about 40 nm in diameter). In some embodiments, the spacer substance or substances between two graphene-based material layers can be the same as or different from the spacer substance or substances between two other graphene-based material layers. That is, the spacer substance or substances in one membrane channel can be the same as or different from the spacer substance or substances in a different membrane channel.

The diameter of the channel can be tailored based on the density and/or size of the spacer substance incorporated into the membrane. For instance, without being bound by theory, an increase in spacer substance density is believed to be associated with an increase in channel diameter as compared to a channel comprising the same spacer substance, but at a lower density. Indeed, an increased distance between spacer substances (i.e., a low density) allows flexible graphene-based material layers to attain stable configurations in which portions of different layers are in close proximity, thereby lowering the diameter of the channel.

In some embodiments, the spacer substances are incorporated at a sufficiently low density to allow inter-layer interactions (e.g., interactions between graphene in different layers). In some embodiments, the spacer substances are incorporated at a sufficiently high density to allow chemical interactions (e.g., covalent or van der Waals interactions) between the layers and the spacer substances, but to prevent inter-layer chemical interactions. In some embodiments, both layer-spacer substance and inter-layer chemical interactions are present in the membrane.

In some embodiments, the spacer substances are positioned in the channel with an average distance between spacer substances of from 10 nm to about 150 nm. In some embodiments, the spacer density is such that spacer substances cover up to about 50% of the surface area of center of the channel—i.e., in a 2D-plane along the center of the channel, spacer substances cover up to about 50% of the area of that plane. In some embodiments, the spacer density is such that the spacer substances cover up to about 40%, up to about 30%, up to about 20%, or up to about 10% of the surface area of the center of the channel. Spacer density can be calculated, for instance, based on the amount of spacer substance used, the dimensions of the membrane, and the dimensions of the spacer.

As mentioned above, the size of the spacer substances can also impact properties of the membrane. For instance, spacer substances with a relatively large effective diameter can be used to prepare channels with a relatively high maximum diameter. The term "maximum diameter" as it relates to channel width is defined by the diameter of the channel at a point of interaction between a layer and the spacer substance in the channel with the largest effective diameter. Notably, because of the flexibility/conformity of graphene-based materials, the diameter of a channel at any given location can be higher or lower than the maximum diameter. In some embodiments, spacer substances with relatively small effective diameter can be used to prepare channels with a relatively low maximum diameter. In some embodiments, the spacer substances have an effective diameter of from about 0.3 nm to about 100 nm, such from about 0.3 nm to about 0.5 nm, from about 0.5 nm to about 2 nm, or from about 20 nm to about 50 nm.

In some embodiments, the spacer substance is restricted from traversing the graphene-based material layers. For example, in some embodiments, the spacer substance is larger than the size of the pores in the graphene-based material layers, or larger than a portion of the pores in the graphene-based material layers. In some embodiments the spacer substance is larger in one dimension than the size of the pores, or a portion thereof, in the graphene-based material layers. In some embodiments, the spacer substance interacts with the graphene-based material layer (e.g., via covalent bonding or van der Waals interactions). In some embodiments, the interactions between the spacer substance and the graphene-based material layer is stronger than an interaction between the spacer substance and permeants that pass through the membrane.

The effective diameter of the spacer substance can be tunable, i.e., it can be altered upon exposure to an environmental stimulus. In this regard, the effective diameter of spacer substances can be altered, upon exposure to an environmental stimulus, by about 0.3 nm to about 50 nm, such as from about 0.3 nm to about 0.5 nm, from about 0.5 nm to about 2 nm, from about 10 nm to about 20 nm, or from about 20 nm to about 50 nm. In some embodiments, the effective diameter of the spacer substance can be reduced by about 0.3 nm to about 50 nm, such as from about 0.3 nm to about 0.5 nm, from about 0.5 nm to about 2 nm, from about 10 nm to about 20 nm, or from about 20 nm to about 50 nm. In some embodiments, the effective diameter of the spacer substance can be increased by about 0.3 nm to about 50 nm, such as from about 0.3 nm to about 0.5 nm, from about 0.5 nm to about 2 nm, from about 10 nm to about 20 nm, or from about 20 nm to about 50 nm.

In some embodiments, the membrane comprises one or more channels that are impermeable (i.e., the channel diameter is about 0, and the channel is referred to as being in a closed position) before and/or after exposure to an environmental stimulus. In some embodiments, the diameter of the channel is from about 0.3 nm to about 100 nm, such from about 0.3 nm to about 0.5 nm, from about 0.5 nm to about 2 nm, or from about 20 nm to about 50 nm. In some embodiments the channel diameter is about 0.5 nm, about 1 nm, about 2 nm, about 5 nm, about 10 nm, about 15, nm, about 20 nm, about 25 nm, about 30 nm, about 35 nm, about 40 nm, about 45 nm, or about 50 nm. In some embodiments, the channel diameter is smaller than the diameter of pores, or a portion of pores, in the graphene-based material layers. The phrases "channel diameter" and "diameter of the channel" are defined by the diameter of substances that can traverse the membrane. For example, substances with a diameter of more than 10 nm are inhibited from traversing a membrane with a channel diameter of 10 nm or less; substances with a diameter of 50 nm or more are inhibited from traversing a membrane with a channel diameter of 50 nm or less. Channel diameter can be assessed, for example, using a flow test to determine the size cutoff for substances that can traverse the membrane. In some embodiments, particles smaller than the diameter of the channel are also inhibited from traversing the channel, for instance due to interactions with the graphene-based material layer or due to a solvation shell around the particle.

The channel diameter can be the larger than, about the same as, or smaller than the diameter of pores on the graphene-based material layer. In some embodiments, the channel diameter is smaller than the average diameter of pores in the graphene-based material layer, such as about 5% smaller, about 10% smaller, about 20% smaller, or about 50% smaller. In some embodiments, the channel diameter is about the same as the average diameter of pores in the graphene-based material layer. In some embodiments, the channel diameter is larger than the average diameter of pores in the graphene-based material layer, and the channel is functionalized; in such embodiments, the channel diameter can be estimated based on the diameter of the spacer substances.

In some embodiments, the channel diameter is tunable, i.e., it can be altered upon exposure to an environmental stimulus, by from about 0.3 nm to about 50 nm, such as from about 0.3 nm to about 0.5 nm, from about 0.5 nm to about 2 nm, or from about 20 nm to about 50 nm. In some embodiments, the channel diameter can be reduced by about 0.3 nm to about 50 nm, such as from about 0.3 nm to about 0.5 nm, from about 0.5 nm to about 2 nm, or from about 20 nm to about 50 nm. In some embodiments, the channel diameter can be increased by about 0.3 nm to about 50 nm, such as from about 0.3 nm to about 0.5 nm, from about 0.5 nm to about 2 nm, or from about 20 nm to about 50 nm. By altering the properties of the spacer substances with an environmental stimulus, permeability and/or selectivity of the membrane (e.g., as measured by a flow test) can also be altered. Thus, membranes of some of the embodiments are responsive to one or more environmental stimuli. For instance, channels located between membrane layers can be increased or decreased in diameter as a result of changes in the size of the spacer substances. In exemplary embodiments, a membrane that allows passage of water but excludes salt ions (e.g. $Na^+$ and $Cl^-$) can be tuned to allow passage of both water and salt ions. In other exemplary embodiments, the membrane can be tuned to allow passage of biological compounds such as insulin, proteins and/or other biological material (e.g., RNA, DNA, and/or nucleic acids), but to exclude passage of other larger biological compounds such as antibodies. In some embodiments, the membrane can be tuned to be permeable to oxygen and nutrients, but to exclude passage of cells (such as immune cells), viruses, bacteria, antibodies, and/or complements of the immune system. In some embodiments, the membrane can be tuned from one that allows passage of antibodies to one that inhibits passage of antibodies.

Tunable membranes have broad application, including in water filtration, immune-isolation (i.e., protecting substances from an immune reaction), timed drug release (e.g., sustained or delayed release), hemodialysis, and hemofiltration. Some embodiments described herein comprise a method of water filtration, water desalination, water purification, immune-isolation, timed drug release, hemodialysis, or hemofiltration, where the method comprises exposing a membrane to an environmental stimulus, and wherein the membrane comprises a first layer with a porous graphene-based material and a second layer with a porous graphene-based material.

Some embodiments include methods of filtering water comprising passing water through a membrane. Some embodiments include desalinating or purifying water comprising passing water through a membrane. The water can be passed through the membrane by any known means, such as by diffusion or gravity filtration, or with applied pressure (e.g. applied with a pump or via osmotic pressure).

Some embodiments include methods of selectively separating or isolating substances in a biological environment, wherein the membrane separates or isolates biological substances based on characteristics of the substance, such as size. Such methods can be useful in the context of disease treatment, such as in the treatment of diabetes. In some embodiments, biological substances below a certain size threshold can migrate across the membrane. In some embodiments, even biological substances below the size threshold are excluded from migrating across the membrane due to functionalization of membrane pores and/or channels.

In some embodiments, the pores, or at least a portion thereof, are functionalized. In some embodiments, the channels, or at least a portion thereof, are functionalized, for instance by attaching or embedding a functional group. In some embodiments, the functionalization moieties are trapped between two graphene-based material layers, but are not restricted to a single position in the channel (i.e., they are mobile within the channel, but are inhibited from traversing the two-dimensional material layers, e.g., based the size of the pores in the graphene-based material layers). In some embodiments, functionalization comprises surface charges (e.g., sulfonates) attached to the pores and/or channels. Without being bound by theory, it is believed that surface charges can impact which molecules and/or ions can traverse the membrane. In some embodiments, functionalization comprises specific binding sites attached to the pores and/or channels. In some embodiments, functionalization comprises proteins or peptides attached to the pores and/or the channel. In some embodiments, functionalization comprises antibodies and/or antigens (e.g., IgG-binding antigens) attached to the pores and/or channels. In some embodiments, functionalization comprises adsorptive substances attached to the pores and/or channels. In some embodiments, functionalization involves catalytic and/or regenerative substances or groups. In some embodiments, functionalization comprises a negatively or partially negatively charged group (e.g., oxygen) attached to the pores and/or channels. In some embodiments, functionalization comprises a positively or partially positively charged group attached to the pores and/or channels.

In some embodiments, functionalizing the pores and/or channels functions to: restrict contaminants from traversing the membrane; act as a disposable filter, capture, or diagnostic tool; increase biocompatibility (e.g., when polyethylene glycol is used for functionalization); increase filtration efficiency; position the spacer substances in the channels (e.g., spacers can be positioned near the pores via affinity-based functionalization in the pores; additional spacers can be positioned in interlaminar areas); increase selectivity at or near the pores or in asymmetric membranes; and/or protect spacer substances (e.g., from the external environment or from a particular vulnerability such as degradation).

Substrate Layer

In some embodiments, a substrate layer is disposed on one or both surfaces of the membrane. Without being bound by theory, it is believed that the substrate layer can improve biocompatibility of membranes, for instance by reducing biofouling, preventing protein adsorption-related problems, and/or enhancing vascularization. In some embodiments, the substrate layer can increase vascularization and/or tissue ingrowth near the membrane, thus prompting the formation of blood vessels and/or tissue ingrowth in close proximity to the membrane.

In some embodiments, the substrate layer has a thickness of about 1 mm or less, about 1 μm or less, or about 100 nm or less. In some embodiments, a thickness of the substrate layer can range from about 100 nm to about 100 μm, or about 1 μm to about 50 μm, or about 10 μm to about 20 μm, or about 15 μm to about 25 μm. In some embodiments, the substrate layer has a thickness about 10 μm or greater, or about 15 μm or greater. In some embodiments, the substrate layer has a thickness of less than 1 μm. In some embodiments, the substrate layer has a thickness of about 10 nm to about 100 nm, or about 20 nm to about 50 nm.

In some embodiments, the enclosure can be supported by one or more support structures. In some embodiments, the support structure can itself have a porous structure wherein the pores are larger than those of the two-dimensional material. In some embodiments, the support structure is formed as a frame at a perimeter of a two-dimensional material. In some embodiments, the support structure is positioned, at least in part, interior to a perimeter of a two-dimensional material. In some embodiments, the substrate layer can convey a desired degree of structural support (e.g., to prevent tearing and/or buckling) to the two-dimensional material layer.

In some embodiments, two or more substrate layers are positioned on the same side of the membrane (e.g., two or more substrate layers can be positioned on the outside of an enclosure comprising the membrane). In some embodiments, the substrate is disposed directly on (or affixed directly to) a graphene-based material layer. In some embodiments, the substrate is disposed on or affixed to the graphene-based material layer with high conformance (e.g., by disposing a slightly wet substrate on the graphene-based material layer). In some embodiments, the substrate is disclosed with low conformance. In some embodiments, the substrate is disposed indirectly on (or affixed indirectly to) the graphene-based material; for instance, an intermediate layer can be positioned between the substrate layer and the graphene-based material layer. In some embodiments, the substrate layer is disposed or directly or indirectly on (or affixed directly or indirectly to) another substrate layer. In some embodiments, the graphene-based material layer is suspended on a substrate layer. In some embodiments, the substrate layer is affixed to the graphene-based material layer.

In some embodiments, the substrate layer can increase vascularization near the membrane, thus prompting the formation of blood vessels and/or tissue ingrowth in close proximity to the membrane. In some embodiments, the increased vascularization contributes to decreasing the effective distance between the blood stream and substances being eluted through the membrane. In some embodiments, the increased vascularization contributes to viability of substances, such as cells, enclosed within an enclosure comprising the membrane.

The substrate layer can be porous and/or nonporous. In some embodiments, the substrate layer contains porous and nonporous sections. In some embodiments the substrate layer comprises a porous or permeable fibrous layer. Porous substrates include, for example, one or more of ceramics and thin film polymers. Exemplary ceramics include nanoporous silica (silicon dioxide), silicon, SiN, and combinations thereof. In some embodiments, the substrate layer comprises track-etched polymers, expanded polymers, patterned polymers, woven polymers, and/or non-woven polymers. In some embodiments, the substrate layer comprises a plurality of polymer filaments. In some embodiments, the polymer filaments can comprise a thermopolymer, thermoplastic polymer, or melt polymer, e.g., that can be molded or set in an optional annealing step. In some embodiments, the polymer filaments are hydrophobic. In some embodiments, the polymer filaments are hydrophilic. In some embodiments, the substrate layer comprises a polymer selected from the group consisting of polysulfones, polyurethane, polymethylmethacrylate (PMMA), polyglycolid acid (PGA), polylactic acid (PLA), polyethylene glycol (PEG), polylactic-co-glycolic acid (PLGA), polyamides (such as nylon-6,6, supramid and nylamid), polyimides, polypropylene, polyethersulfones (PES), polyvinylidine fluoride (PVDF), cellulose acetate, polyethylene, polypropylene, polycarbonate, polytetrafluoroethylene (PTFE) (such as Teflon), polyvinylchloride (PVC), polyether ether ketone (PEEK), mixtures and block co-polymers of any of these, and combinations and/or mixtures thereof. In some embodiments, the polymers are biocompatible, bioinert and/or medical grade materials.

In some embodiments, the substrate layer comprises a biodegradable polymer. In some embodiments, a substrate layer forms a shell around an enclosure comprising the membrane (e.g., it completely engulfs the enclosure). In some embodiments, the substrate layer shell can be dissolved or degraded, e.g., in vitro. In some embodiments, the shell can be loaded with additives, including additives that protect substances inside the enclosure from air or prevent the need for a stabilizing agent.

Suitable techniques for depositing or forming a porous or permeable polymer on the graphene-based material layer include casting or depositing a polymer solution onto the graphene-based material layer or intermediate layer using a method such as spin-coating, spray coating, curtain coating, doctor-blading, immersion coating, electrospinning, or other similar techniques. Electrospinning techniques are described, e.g., in US 2009/0020921 and/or U.S. application Ser. No. 14/609,325, both of which are hereby incorporated by reference in their entirety.

In some embodiments, the process for forming a substrate layer includes an electrospinning process in which a plurality of polymer filaments are laid down to form a porous mat, e.g., on the graphene-based material layer. In some embodiments, the mat has pores or voids located between deposited filaments of the fibrous layer. FIG. 5 shows an illustrative SEM micrograph of a graphene or graphene-based film deposited upon a plurality of electrospun PVDF fibers. In some embodiments, the electrospinning process comprises a melt electrospinning process or a solution electrospinning process, such as a wet electrospinning process or a dry electrospinning process. (See, e.g., Sinha-Ray et al. *J. Membrane Sci.* 485, 1 Jul. 2015, 132-150.) In some embodiments, the polymer can be present in a spin dope at a concentration of 2 wt. % to 15 wt. %, or 5 wt. % to 10 wt. %, or about 7 wt. %. Suitable solvents for the spin dope include any solvent that dissolves the polymer to be deposited and which rapidly evaporates, such as m-cresol, formic acid, dimethyl sulfoxide (DMSO), ethanol, acetone, dimethylacetamide (DMAC), dimethylformamide (DMF), water, and combinations thereof. In some embodiments, the spin dope solvent is biocompatible and/or bioinert. In some embodiments, the amount of solvent used can influence the morphology of the substrate layer. In dry electrospinning processes, the spun fibers of the fibrous layer can remain as essentially discrete entities once deposited. In some embodiments, wet electrospinning processes deposit the spun fibers such that they are at least partially fused together when deposited. In some embodiments, the size and morphology of the deposited fiber mat (e.g., degree of porosity, effective pore size, thickness of fibrous layer, gradient porosity) can be tailored based on the electrospinning process used.

The porosity of the fibrous layer can include effective void space values (e.g. measured via imagery) up to about 95% (i.e., the layer is 95% open), about 90%, about 80%, or about 60%, with a broad range of void space sizes. In some embodiments, a single spinneret can be moved to lay down a mat of the fibrous layer. In some embodiments, multiple spinnerets can be used for this purpose. In some embodiments, the spun fibers in an electrospun fibrous layer can have a fiber diameter ranging from about 1 nm to about 100 µm, or about 10 nm to about 1 µm, or about 10 nm to about 500 nm, or about 100 nm to about 200 nm, or about 50 nm to about 120 nm, or about 1 µm to about 5 µm, or about 1 µm to about 6 µm, or about 5 µm to about 10 µm. In some embodiments, the fiber diameter is directly correlated with a depth (Z-axis) of a pore abutting the graphene-based material layer (disposed in the X-Y plane), and large diameter fibers can lead to large unsupported spans of material.

In some embodiments, the substrate layer can have pores (e.g., void spaces) with an effective pore size of from about 1 nm to about 100 µm, or about 10 nm to about 1 µm, or about 10 nm to about 500 nm, or about 100 nm to about 200 nm, or about 50 nm to about 120 nm, or about 1 µm to about 5 µm, or about 1 µm to about 6 µm, or about 5 µm to about 10 µm. Pore diameters in the substrate layer can be measured, for example, via porometry methods (e.g., capillary flow porometry) or extrapolated via imagery.

In some embodiments, the substrate layer can have an average pore size gradient throughout its thickness. "Pore size gradient" describes a layer with a plurality of pores, where the average diameter of the pores increases or decreases based on the proximity of the pore to the graphene-based material layer. For example, a fibrous layer can have an average pore size gradient that decreases nearer the surface of a graphene-based material. In some embodiments, an average pore size of the fibrous layer is smaller nearer the surface of the graphene-based material than at an opposite surface of the fibrous layer. For example, the fibrous layer can have effective pore diameters of less than about 200 nm close to the intermediate layer or the graphene-based material layer which can increase to greater than 100 µm at the maximum distance away from the intermediate layer or graphene-based material layer.

In some embodiments, the fibrous layer can have a "porosity gradient" throughout its thickness, which can be measured for instance using imagery. "Porosity gradient" describes a change, along a dimension of the fibrous layer, in the porosity or total pore volume as a function of distance from the graphene-based material layer. For example, throughout the thickness of the porous fibrous layer, the porosity can change in a regular or irregular manner. A porosity gradient can decrease from one face of the fibrous layer to the other. For example, the lowest porosity in the fibrous layer can be located spatially closest to the graphene-based material layer, and the highest porosity can be located farther away (e.g., spatially closer to an external environment). A porosity gradient of this type can be achieved by electrospinning fibers onto a graphene-based material layer such that a fiber mat is denser near the surface of the graphene-based material layer and less dense further from the surface of the graphene-based material layer. In some embodiments, a substrate layer can have a relatively low porosity close to the graphene-based material layer, a higher porosity at a mid-point of the fibrous layer thickness (which can, for example, contain a supporting mesh for reinforcement or other particles), and return to a relatively low porosity at an external surface distal to the graphene-based material layer.

In some embodiments, the substrate layer can have a "permeability gradient" throughout its thickness. "Permeability gradient," as used herein, describes a change, along a dimension of the fibrous layer, in the "permeability" or rate of flow of a liquid or gas through a porous material. For example, throughout the thickness of the fibrous layer, the permeability can change in a regular or irregular manner. A permeability gradient can decrease from one face of the fibrous layer to the other. For example, the lowest permeability in the fibrous layer can be located spatially closest to the graphene-based material layer, and the highest permeability can be located farther away. Those of skill in the art will understand that permeability of a layer can increase or decrease without pore diameter or porosity changing, e.g., in response to chemical functionalization, applied pressure, voltage, or other factors.

In some embodiments, both the graphene-based material layer and the substrate layer include a plurality of pores therein. In some embodiments, both the graphene-based material layer and the substrate layer contain pores, and the pores in the graphene-based material layer are smaller, on average, than the pores in the substrate layer. In some embodiments, the median pore size in the graphene-based material layer is smaller than the median pore size in the substrate layer. For example, in some embodiments, the substrate layer can contain pores with an average and/or median diameter of about 1 µm or larger and the graphene-based material layer can contain pores with an average and/or median diameter of about 10 nm or smaller. Accordingly, in some embodiments, the average and/or median diameter of pores in the graphene-based material layer is at least about 10-fold smaller than the average and/or median diameter of pores in the substrate layer. In some embodiments, the average and/or median diameter of pores in the graphene-based material layer is at least about 100-fold smaller than are the average and/or media diameter of pores in the substrate layer.

In some embodiments, the substrate layer can provide a scaffold for tissue growth, cell growth and/or vascularization. In some embodiments, the substrate layer or wall comprises additives, such as pharmaceuticals, cells, growth factors (e.g., VEGF), signaling molecules, cytokines, clotting factors, blood thinners, immunosuppressants, antimicrobial agents, hormones, antibodies, minerals, nutrients or combinations thereof. In some embodiments, additives such as pharmaceuticals, cells, growth factors, clotting factors, blood thinners, immunosuppressants, antimicrobial agents, hormones, antibodies, antigens (e.g., IgG-binding antigens) or an antibody-binding fragment thereof, minerals, nutrients or combinations thereof are positioned on the inside of the disclosure. In some embodiments, the substrate layer or membrane comprises materials toxic to bacteria or cells (without being bound by theory, it is believed that incorporating toxic materials into the wall will prevent passage of potentially dangerous or detrimental cells across the membrane).

In some embodiments, additives beneficially promote cell or tissue viability or growth, reduce or prevent infection, improve vascularization to or near the membrane, improve biocompatibility, reduce biofouling, and/or reduce the risk of adverse reactions. In some embodiments, additives can modulate properties, such as hydrophobicity or hydrophilicity, of the substrate layer. In some embodiments, additives can be used to modulate elution of a substance from a compartment in the enclosure. For instance, additives can confer shell-like properties to a substrate layer, such that degradation or removal of the additives allows substances to traverse the membrane.

In some embodiments, an intermediate layer promotes adhesion between the graphene-based material layer and the substrate layer. Thus, in some embodiments, the enclosure comprises an intermediate layer disposed between the graphene-based material layer and the substrate layer. In some embodiments, the enclosure comprises an intermediate layer positioned between two substrate layers on the same side of the graphene-based material layer.

In some embodiments, the intermediate layer comprises carbon nanotubes, lacey carbon, nanoparticles, lithographically patterned low-dimensional materials, silicon and silicon nitride micromachined material, a fine mesh, such as a transmission electron microscopy grid, or combinations of these. In some embodiments, the intermediate layer can be a thin, smooth, porous polymer layer, such as a track etched polymer. In some embodiments, the intermediate layer has a thickness of from 3 nm to 10 µm, 10 nm to 10 µm, 50 nm to 10 µm, 100 nm to 10 µm, 500 nm to 10 µm, 1 µm to 10 µm, or 2 µm to 6 µm.

Graphene-Based Materials

As discussed above, membranes of some of the embodiments comprise graphene-based materials.

Graphene represents a form of carbon in which the carbon atoms reside within a single atomically thin sheet or a few layered sheets (e.g., about 20 or less) of fused six-membered rings forming an extended $sp^2$-hybridized carbon planar lattice. Graphene-based materials include, but are not limited to, single layer graphene, multilayer graphene or interconnected single or multilayer graphene domains and combinations thereof. In some embodiments, graphene-based materials also include materials which have been formed by stacking single or multilayer graphene sheets. In some embodiments, multilayer graphene includes 2 to 20 layers, 2 to 10 layers or 2 to 5 layers. In some embodiments, layers of multilayered graphene are stacked, but are less ordered in the z direction (perpendicular to the basal plane) than a thin graphite crystal.

In some embodiments, a sheet of graphene-based material may be a sheet of single or multilayer graphene or a sheet comprising a plurality of interconnected single or multilayer graphene domains, which may be observed in any known manner such as using for example small angle electron diffraction, transmission electron microscopy, etc. In some embodiments, the multilayer graphene domains have 2 to 5 layers or 2 to 10 layers. As used herein, a domain refers to a region of a material where atoms are substantially uniformly ordered into a crystal lattice. A domain is uniform within its boundaries, but may be different from a neighboring region. For example, a single crystalline material has a single domain of ordered atoms. In some embodiments, at least some of the graphene domains are nanocrystals, having domain size from 1 to 100 nm or 10-100 nm. In some embodiments, at least some of the graphene domains have a domain size greater than from 100 nm to 1 cm, or from 100 nm to 1 micron, or from 200 nm to 800 nm, or from 300 nm to 500 nm. In some embodiments, a domain of multilayer graphene may overlap a neighboring domain. Grain boundaries formed by crystallographic defects at edges of each domain may differentiate between neighboring crystal lattices. In some embodiments, a first crystal lattice may be rotated relative to a second crystal lattice, by rotation about an axis perpendicular to the plane of a sheet, such that the two lattices differ in crystal lattice orientation.

In some embodiments, the sheet of graphene-based material is a sheet of single or multilayer graphene or a combination thereof. In some other embodiments, the sheet of graphene-based material is a sheet comprising a plurality of interconnected single or multilayer graphene domains. In some embodiments, the interconnected domains are covalently bonded together to form the sheet. When the domains in a sheet differ in crystal lattice orientation, the sheet is polycrystalline.

In some embodiments, the thickness of the sheet of graphene-based material is from 0.3 to 10 nm, 0.34 to 10 nm, from 0.34 to 5 nm, or from 0.34 to 3 nm. In some embodiments, the thickness includes both single layer graphene and the non-graphenic carbon.

In some embodiments, a sheet of graphene-based material comprises intrinsic or native defects. Intrinsic or native defects may result from preparation of the graphene-based material in contrast to perforations which are selectively introduced into a sheet of graphene-based material or a sheet of graphene. Such intrinsic or native defects may include, but are not limited to, lattice anomalies, pores, tears, cracks or wrinkles. Lattice anomalies can include, but are not limited to, carbon rings with other than 6 members (e.g. 5, 7 or 9 membered rings), vacancies, interstitial defects (including incorporation of non-carbon atoms in the lattice), and grain boundaries. Perforations are distinct from openings in the graphene lattice due to intrinsic or native defects or grain boundaries, but testing and characterization of the final membrane such as mean pore size and the like encompasses all openings regardless of origin since they are all present.

In some embodiments, graphene is the dominant material in a graphene-based material. For example, a graphene-based material may comprise at least 20% graphene, 30% graphene, or at least 40% graphene, or at least 50% graphene, or at least 60% graphene, or at least 70% graphene, or at least 80% graphene, or at least 90% graphene, or at least 95% graphene. In some embodiments, a graphene-based material comprises a range of graphene selected from 30% to 95%, or from 40% to 80% from 50% to 70%, from 60% to 95% or from 75% to 100%. The amount of graphene in the graphene-based material is quantified as an atomic percentage utilizing known methods including scanning transmission electron microscope examination, or alternatively if STEM or TEM is ineffective another similar measurement technique.

In some embodiments, a sheet of graphene-based material further comprises non-graphenic carbon-based material located on at least one surface of the sheet of graphene-based material. In some embodiments, the sheet is exemplified by two base surfaces (e.g. top and bottom faces of the sheet, opposing faces) and side faces (e.g. the side faces of the sheet). In some further embodiments, the "bottom" face of the sheet is that face which contacted the substrate during growth of the sheet and the "free" face of the sheet opposite the "bottom" face. In some embodiments, non-graphenic carbon-based material may be located on one or both base surfaces of the sheet (e.g. the substrate side of the sheet and/or the free surface of the sheet). In some further embodiments, the sheet of graphene-based material includes a small amount of one or more other materials on the surface, such as, but not limited to, one or more dust particles or similar contaminants.

In some embodiments, the amount of non-graphenic carbon-based material is less than the amount of graphene. In some further embodiments, the amount of non-graphenic carbon material is three to five times the amount of graphene; this is measured in terms of mass. In some additional embodiments, the non-graphenic carbon material is characterized by a percentage by mass of said graphene-based material selected from the range of 0% to 80%. In some embodiments, the surface coverage of the sheet of non-graphenic carbon-based material is greater than zero and less than 80%, from 5% to 80%, from 10% to 80%, from 5% to 50% or from 10% to 50%. This surface coverage may be measured with transmission electron microscopy, which gives a projection. In some embodiments, the amount of graphene in the graphene-based material is from 60% to 95% or from 75% to 100%. The amount of graphene in the graphene-based material is quantified as an atomic percentage utilizing known methods preferentially using transmission electron microscope examination, or alternatively if STEM is ineffective using an atomic force microscope.

In some embodiments, the non-graphenic carbon-based material does not possess long range order and is classified as amorphous. In some embodiments, the non-graphenic carbon-based material further comprises elements other than carbon and/or hydrocarbons. In some embodiments, non-carbon elements which may be incorporated in the non-graphenic carbon include hydrogen, oxygen, silicon, copper, and iron. In some further embodiments, the non-graphenic carbon-based material comprises hydrocarbons. In some embodiments, carbon is the dominant material in non-graphenic carbon-based material. For example, a non-graphenic carbon-based material in some embodiments comprises at least 30% carbon, or at least 40% carbon, or at least 50% carbon, or at least 60% carbon, or at least 70% carbon, or at least 80% carbon, or at least 90% carbon, or at least 95% carbon. In some embodiments, a non-graphenic carbon-based material comprises a range of carbon selected from 30% to 95%, or from 40% to 80%, or from 50% to 70%. The amount of carbon in the non-graphenic carbon-based material is quantified as an atomic percentage utilizing known methods preferentially using transmission electron microscope examination, or alternatively if STEM is ineffective using atomic force microscope.

Perforation techniques suitable for use in perforating the graphene-based materials may include described herein ion-based perforation methods and UV-oxygen based methods.

Ion-based perforation methods include methods in which the graphene-based material is irradiated with a directional source of ions. In some further embodiments, the ion source is collimated. In some embodiments, the ion source is a broad beam or flood source. A broad field or flood ion source can provide an ion flux which is significantly reduced compared to a focused ion beam. The ion source inducing perforation of the graphene or other two-dimensional material is considered to provide a broad ion field, also commonly referred to as an ion flood source. In some embodiments, the ion flood source does not include focusing lenses. In some embodiments, the ion source is operated at less than atmospheric pressure, such as at $10^{-3}$ to $10^{-5}$ torr or $10^{-4}$ to $10^{-6}$ torr. In some embodiments, the environment also contains background amounts (e.g. on the order of $10^{-5}$ torr) of oxygen ($O_2$), nitrogen ($N_2$) or carbon dioxide ($CO_2$). In some embodiments, the ion beam may be perpendicular to the surface of the layer(s) of the material (incidence angle of 0 degrees) or the incidence angle may be from 0 to 45 degrees, 0 to 20 degrees, 0 to 15 degrees or 0 to 10 degrees. In some further embodiments, exposure to ions does not include exposure to plasma.

In some embodiments, UV-oxygen based perforation methods include methods in which the graphene-based material is simultaneously exposed to ultraviolet (UV) light and an oxygen containing gas Ozone may be generated by exposure of an oxygen containing gas such as oxygen or air to the UV light. Ozone may also be supplied by an ozone generator device. In some embodiments, the UV-oxygen based perforation method further includes exposure of the graphene-based material to atomic oxygen. Suitable wavelengths of UV light include, but are not limited to wavelengths below 300 nm or from 150 nm to 300 nm. In some embodiments, the intensity from 10 to 100 mW/cm$^2$ at 6 mm distance or 100 to 1000 mW/cm$^2$ at 6 mm distance. For example, suitable light is emitted by mercury discharge lamps (e.g. about 185 nm and 254 nm). In some embodiments, UV/oxygen cleaning is performed at room temperature or at a temperature greater than room temperature. In some further embodiments, UV/oxygen cleaning is performed at atmospheric pressure (e.g. 1 atm) or under vacuum.

Perforations are sized as described herein to provide desired selective permeability of a species (atom, molecule, protein, virus, cell, etc.) for a given application. Selective permeability relates to the propensity of a porous material or a perforated two-dimensional material to allow passage (or transport) of one or more species more readily or faster than other species. Selective permeability allows separation of species which exhibit different passage or transport rates. In two-dimensional materials selective permeability correlates to the dimension or size (e.g., diameter) of apertures and the relative effective size of the species. Selective permeability of the perforations in two-dimensional materials such as graphene-based materials can also depend on functionalization of perforations (if any) and the specific species. Separation or passage of two or more species in a mixture includes a change in the ratio(s) (weight or molar ratio) of the two or more species in the mixture during and after passage of the mixture through a perforated two-dimensional material.

In some embodiments, the characteristic size of the perforation is from 0.3 to 10 nm, from 1 to 10 nm, from 5 to 10 nm, from 5 to 20 nm, from 10 nm to 50 nm, from 50 nm to 100 nm, from 50 nm to 150 nm, from 100 nm to 200 nm, or from 100 nm to 500 nm. In some embodiments, the average pore size is within the specified range. In some embodiments, 70% to 99%, 80% to 99%, 85% to 99% or 90 to 99% of the perforations in a sheet or layer fall within a specified range, but other pores fall outside the specified range.

Nanomaterials in which pores are intentionally created may be referred to as perforated graphene, perforated graphene-based materials or perforated two-dimensional materials, and the like. Perforated graphene-based materials include materials in which non-carbon atoms have been incorporated at the edges of the pores. Pore features and other material features may be characterized in a variety of manners including in relation to size, area, domains, periodicity, coefficient of variation, etc. For instance, the size of a pore may be assessed through quantitative image analysis utilizing images preferentially obtained through transmission electron microscopy, and if TEM is ineffective, through atomic force microscopy, and if AFM is ineffective, through scanning electron microscopy, as for example presented in FIGS. 1 and 2. The boundary of the presence and absence of material identifies the contour of a pore. The size of a pore may be determined by shape fitting of an expected species against the imaged pore contour where the size measurement is characterized by smallest dimension unless otherwise specified. For example, in some instances, the shape may be round or oval. The round shape exhibits a constant and smallest dimension equal to its diameter. The width of an oval is its smallest dimension. The diameter and width measurements of the shape fitting in these instances provide the size measurement, unless specified otherwise.

Each pore size of a test sample may be measured to determine a distribution of pore sizes within the test sample. Other parameters may also be measured such as area, domain, periodicity, coefficient of variation, etc. Multiple test samples may be taken of a larger membrane to determine that the consistency of the results properly characterizes the whole membrane. In such instance, the results may be confirmed by testing the performance of the membrane with test species. For example, if measurements indicate that certain sizes of species should be restrained from transport across the membrane, a performance test provides verification with test species. Alternatively, the performance test may be utilized as an indicator that the pore measurements will determine a concordant pore size, area, domains, periodicity, coefficient of variation, etc.

The size distribution of holes may be narrow, e.g., limited to 0.1-0.5 coefficient of variation. In some embodiments, the characteristic dimension of the holes is selected for the application.

In some embodiments involving circular shape fitting the equivalent diameter of each pore is calculated from the equation $A=\pi d^2/4$. Otherwise, the area is a function of the shape fitting. When the pore area is plotted as a function of equivalent pore diameter, a pore size distribution may be obtained. The coefficient of variation of the pore size may be calculated herein as the ratio of the standard deviation of the pore size to the mean of the pore size as measured across the test samples. The average area of perforations is an averaged measured area of pores as measured across the test samples.

In some embodiments, the ratio of the area of the perforations to the ratio of the area of the sheet may be used to characterize the sheet as a density of perforations. The area of a test sample may be taken as the planar area spanned by the test sample. Additional sheet surface area may be excluded due to wrinkles other non-planar features. Characterization may be based on the ratio of the area of the perforations to the test sample area as density of perforations excluding features such as surface debris. Characterization may be based on the ratio of the area of the perforations to the suspended area of the sheet. As with other testing, multiple test samples may be taken to confirm consistency across tests and verification may be obtained by performance testing. The density of perforations may be, for example, 2 per $nm^2$ ($2/nm^2$) to 1 per $\mu m^2$ ($1/\mu m^2$).

In some embodiments, the perforated area comprises 0.1% or greater, 1% or greater or 5% or greater of the sheet area, less than 10% of the sheet area, less than 15% of the sheet area, from 0.1% to 15% of the sheet area, from 1% to 15% of the sheet area, from 5% to 15% of the sheet area or from 1% to 10% of the sheet area. In some further embodiments, the perforations are located over greater than 10% or greater than 15% of said area of said sheet of graphene-based material. A macroscale sheet is macroscopic and observable by the naked eye. In some embodiments, at least one lateral dimension of the sheet is greater than 3 cm, greater than 1 cm, greater than 1 mm or greater than 5 mm. In some further embodiments, the sheet is larger than a graphene flake which would be obtained by exfoliation of graphite in known processes used to make graphene flakes. For example, the sheet has a lateral dimension greater than about 1 micrometer. In an additional embodiment, the lateral dimension of the sheet is less than 10 cm. In some further embodiments, the sheet has a lateral dimension (e.g., perpendicular to the thickness of the sheet) from 10 nm to 10 cm or greater than 1 mm and less than 10 cm.

Chemical vapor deposition growth of graphene-based material typically involves use of a carbon containing precursor material, such as methane and a growth substrate. In some embodiments, the growth substrate is a metal growth substrate. In some embodiments, the metal growth substrate is a substantially continuous layer of metal rather than a grid or mesh. Metal growth substrates compatible with growth of graphene and graphene-based materials include transition metals and their alloys. In some embodiments, the metal growth substrate is copper based or nickel based. In some embodiments, the metal growth substrate is copper or nickel. In some embodiments, the graphene-based material is removed from the growth substrate by dissolution of the growth substrate.

In some embodiments, the sheet of graphene-based material is formed by chemical vapor deposition (CVD) followed by at least one additional conditioning or treatment step. In some embodiments, the conditioning step is selected from thermal treatment, UV-oxygen treatment, ion beam treatment, and combinations thereof. In some embodiments, thermal treatment may include heating to a temperature from 200° C. to 800° C. at a pressure of $10^{-7}$ torr to atmospheric pressure for a time of 2 hours to 8 hours. In some embodiments, UV-oxygen treatment may involve exposure to light from 150 nm to 300 nm and an intensity from 10 to 100 $mW/cm^2$ at 6 mm distance for a time from 60 to 1200 seconds. In some embodiments, UV-oxygen treatment may be performed at room temperature or at a temperature greater than room temperature. In some further embodiments, UV-oxygen treatment may be performed at atmospheric pressure (e.g. 1 atm) or under vacuum. In some embodiments, ion beam treatment may involve exposure of the graphene-based material to ions having an ion energy from 50 eV to 1000 eV (for pretreatment) and the fluence is from $3\times10^{10}$ ions/cm$^2$ to $8\times10^{11}$ ions/cm$^2$ or $3\times10^{10}$ ions/cm$^2$ to $8\times10^{13}$ ions/cm$^2$ (for pretreatment). In some further embodiments, the source of ions may be collimated, such as a broad beam or flood source. In some embodiments, the ions may be noble gas ions such as Xe$^-$. In some embodiments, one or more conditioning steps are performed while the graphene-based material is attached to a substrate, such as a growth substrate.

In some embodiments, the conditioning treatment affects the mobility and/or volatility of the non-graphitic carbon-based material. In some embodiments, the surface mobility of the non-graphenic carbon-based material is such that when irradiated with perforation parameters such as described herein, the non-graphenic carbon-based material, may have a surface mobility such that the perforation process results ultimately in perforation. Without wishing to be bound by any particular belief, hole formation is believed to be related to beam induced carbon removal from the graphene sheet and thermal replenishment of carbon in the hole region by non graphenic carbon. The replenishment process may be dependent upon energy entering the system during perforation and the resulting surface mobility of the non-graphenic carbon based material. To form holes, the rate of graphene removal may be higher than the non-graphenic carbon hole filling rate. These competing rates depend on the non-graphenic carbon flux (e.g., mobility [viscosity and temperature] and quantity) and the graphene removal rate (e.g., particle mass, energy, flux).

In some embodiments, the volatility of the non-graphenic carbon-based material may be less than that which is obtained by heating the sheet of graphene-based material to 500° C. for 4 hours in vacuum or at atmospheric pressure with an inert gas.

In various embodiments, CVD graphene or graphene-based material can be liberated from its growth substrate (e.g., Cu) and transferred to a supporting grid, mesh or other supporting structure. In some embodiments, the supporting structure may be configured so that at least some portions of the sheet of graphene-based material are suspended from the supporting structure. For example, at least some portions of the sheet of graphene-based material may not be in contact with the supporting structure.

In some embodiments, the sheet of graphene-based material following chemical vapor deposition comprises a single layer of graphene having at least two surfaces and non-graphenic carbon based material may be provided on said surfaces of the single layer graphene. In some embodiments, the non-graphenic carbon based material may be located on one of the two surfaces or on both. In some further embodiments, additional graphenic carbon may also present on the surface(s) of the single layer graphene.

Methods of Making Tunable Membranes

Tunable membranes can be made by a variety of methods. For instance, a perforated graphene layer can be combined with spacer substances in solution, such that the spacer substances self-assemble to the perforated graphene layer. Then, the solution can be reduced to induce bonding between the spacer substance and the graphene layer. After that, an additional graphene layer can be added to the solution, which can bond to the graphene layer-spacer substance complex. Attachment of the additional graphene layer can be via van der Waals forces or induced covalent bonding (e.g., as a result of an applied energy such as ion radiation).

In some embodiments, spacer substances are covalently bonded to at least one graphene-based material layer. Without being bound by theory, it is believed that covalent bonding between a spacer substance and a graphene-based material layer can be induced via ion-beam induced bonding, electron-beam induced bonding, heating, chemical reactions (e.g., via reactants on—i.e., attached to—the spacer substance and the graphene-based material layer), and combinations thereof.

In some embodiments, functional moieties are attached to the spacer molecules to facilitate self-assembly on or bonding to the graphene layers. In some embodiments, the functional moieties are removed in the process of making the membrane.

In some embodiments, the spacer substances are trapped between two graphene-based material layers. In some embodiments the spacer substances are trapped between two graphene-based material layers, but are not restricted to a single position in the channel (i.e., they are mobile within the channel).

Unless defined otherwise, all technical and scientific terms used in this description have the same meaning as commonly understood by those skilled in the relevant art.

For convenience, the meaning of certain terms employed in the specification and appended claims are provided below. Other terms and phrases are defined throughout the specification.

The singular forms "a," "an," and "the" include plural reference unless the context clearly dictates otherwise.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Given the disclosure of the present invention, one versed in the art would appreciate that there may be other embodiments and modifications within the scope and spirit of the invention. Accordingly, all modifications attainable by one versed in the art from the present invention within the scope and spirit of the present invention are to be included as further embodiments of the present invention.

What is claimed is:

1. A method of altering membrane permeability comprising:
   exposing a membrane to an environmental stimulus to thereby alter membrane permeability, wherein the membrane comprises a first layer with a porous graphene-based material, a second layer with a porous graphene-based material, and a channel between the first layer and the second layer, and
   wherein the channel has a diameter that is altered upon exposing the membrane to the environmental stimulus.

2. The method of claim 1, wherein the environmental stimulus is selected from the group consisting of variations in temperature, pressure, pH, ionic concentration, solute concentration, tonicity, light, voltage, electric fields, magnetic fields, pi-bonding availability, and combinations thereof.

3. The method of claim 1, wherein the membrane permeability is altered by a change in the maximum diameter of the channel between the first layer and the second layer.

4. The method of claim 1, wherein the membrane comprises at least one spacer substance positioned between the first layer and the second layer, wherein the at least one spacer substance is responsive to the environmental stimulus.

5. The method of claim 1, wherein the at least one spacer substance expands and/or contracts in response to the environmental stimulus.

* * * * *